United States Patent
Goldman et al.

(10) Patent No.: US 10,300,070 B2
(45) Date of Patent: May 28, 2019

(54) METABOLICALLY-ACTIVATED DRUG CONJUGATES TO OVERCOME RESISTANCE IN CANCER THERAPY

(71) Applicant: The Brigham and Women's Hospital, Inc., Boston, MA (US)

(72) Inventors: Aaron Goldman, Somerville, MA (US); Shiladitya Sengupta, Waltham, MA (US); Abhimanyu Paraskar, Belmont, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 15/127,973

(22) PCT Filed: Mar. 27, 2015

(86) PCT No.: PCT/US2015/023135
§ 371 (c)(1),
(2) Date: Sep. 21, 2016

(87) PCT Pub. No.: WO2015/149001
PCT Pub. Date: Oct. 1, 2015

(65) Prior Publication Data
US 2017/0105998 A1  Apr. 20, 2017

Related U.S. Application Data

(60) Provisional application No. 61/971,249, filed on Mar. 27, 2014.

(51) Int. Cl.
| | | |
|---|---|---|
| *A01N 43/04* | (2006.01) | |
| *A61K 31/70* | (2006.01) | |
| *A61K 31/5377* | (2006.01) | |
| *A61K 31/704* | (2006.01) | |
| *A61K 45/06* | (2006.01) | |
| *A61K 31/7068* | (2006.01) | |
| *A61K 47/55* | (2017.01) | |
| *A61K 47/54* | (2017.01) | |

(52) U.S. Cl.
CPC ........ *A61K 31/5377* (2013.01); *A61K 31/704* (2013.01); *A61K 31/7068* (2013.01); *A61K 45/06* (2013.01); *A61K 47/55* (2017.08); *A61K 47/556* (2017.08)

(58) Field of Classification Search
None
See application file for complete search history.

(56) References Cited

U.S. PATENT DOCUMENTS

2009/0274698 A1  11/2009  Bliagwat et al.
2012/0130059 A1  5/2012  Beria et al.

FOREIGN PATENT DOCUMENTS

| WO | WO 2004/064734 | 8/2004 |
| WO | 2013/188727 | 12/2013 |
| WO | WO 2013/188763 | 12/2013 |

OTHER PUBLICATIONS

Citro et al., "Reversal of Adriamycin Resistance by Lonidamine in a Human Breast Cancer Cell Line," British Journal of Cancer, 1991, 64: 534-536.
Li et al., "Mitochondrial targeting drug lonidamine triggered apoptosis in doxorubic n-resistant HepG2 cells," Life Sciences, Oct. 2002, 71: 2729-2740.
Partial Supplementary European Search Report in Application No. 15768447.3, dated Jul. 28, 2017, 15 pages.
Patil et al., "Novel self-assembled lithocholic acid nanoparticles for drug delivery in cancer," RSC Advances, 2013, 3: 19760-19764.
Yi et al., "Inhibition of constitutively activated phosphoinositide 3-kinase/AKT pathway enhances antitumor activity of chemotherapeutic agents in breast cancer susceptibility gene 1-defective breast cancer cells," Molecular Carcinogenesis, Sep. 2013, 52: 667-675.
International Search Report and Written Opinion dated Aug. 12, 2015 in International Application No. PCT/US2015/023135, 13 pgs.
Alexandre et al., "Accumulation of hydrogen peroxide is an early and crucial step for paclitaxel-induced cancer cell death both in vitro and in vivo," Int J Cancer, 2006, 119: 41-48.
Almendro et al., "Cellular heterogeneity and molecular evolution in cancer," Annual Review of Pathology, Jan. 2013, 8: 277-302.
Anastasiou et al., "Inhibition of pyruvate kinase M2 by reactive oxygen species contributes to cellular antioxidant responses," Science, Dec. 2011, 334: 1278-1283.
Bains et al., "A correlation between cytotoxicity and reductase-mediated metabolism in cell lines treated with doxorubicin and daunorubicin," The Journal of Pharmacology and Experimental Thempeutics, Nov. 2013, 347: 375-387.
Bemardini et al., "Comparative activity of doxorubicin and its major metabolite, doxorubicinol, on V79/AP4 fibroblasts: a morphofunctional study," Experimental and Molecular Pathology, Dec. 1991, 55: 238-250.
Bonnet et al., "A mitochondria-K+ channel axis is suppressed in cancer and its normalization promotes apoptosis and inhibits cancer growth," Cancer Cell, Jan. 2007, 11: 37-51.
Brock et al., "Non-genetic heterogeneity—a mutation-independent driving force for the somatic evolution of tumours," Nature Reviews. Genetics, 2009, 10: 336-342.
Cairns et al., "Regulation of cancer cell metabolism," Nat Rev Cancer, Feb. 2011, 11: 85-95.
Cairns, "Mutation selection and the natural history of cancer," Nature, May 1975, 255: 197-200.
Cantor and Sabatini, "Cancer cell metabolism: one hallmark, many faces," Cancer Discovery, Oct. 2012, 2: 881-898.
Chambers et al., "The anti-trypanosomal agent lonidamine inhibits Trypanosoma brucei hexokinase 1," Molecular and Biochemical Parasitology, Apr. 2008, 158: 202-207.
Chandarlapaty, "Negative feedback and adaptive resistance to the targeted therapy of cancer," Cancer Discovery, Apr. 2012, 2: 311-319.

(Continued)

*Primary Examiner* — Patrick T Lewis
(74) *Attorney, Agent, or Firm* — Fish & Richardson P.C.

(57) ABSTRACT

Described are combination therapies and metabolically-activated drug conjugates and their use in treating cancer in subjects.

5 Claims, 22 Drawing Sheets

(56) References Cited

OTHER PUBLICATIONS

Chen et at, "Regulation of glut1 mRNA by hypoxia-inducible factor-I. Interaction between H-ras and hypoxia," J Biol Chem, Mar. 2001, 276: 9519-9525.
Chen et al., "Role of granulocyte macrophage colony-stimulating factor in host defense against pulmonary Cryptococcus neoformans infection during murine allergic bronchopulmonary mycosis," Am J Pathol, Mar. 2007, 170: 1028-1040.
Chia et al., "Novel agents and associated toxicities of inhibitors of the pi3k/Akt/mtor pathway for the treatment of breast cancer," Curr Oncol., Feb. 2015, (1):33-48.
Davis et al., "Deregulation of the EGFR/PI3K/PTEN/Akt/mTORC1 pathway in breast cancer: possibilities for therapeutic intervention," Oncotarget, 2014, 5: 4603-4650.
Decker and Sausville, "Preclinical modeling of combination treatments: fantasy or requirement?," Ann NY Acad Sci, Nov. 2005, 1059: 61-69.
Dikalov, "Cross talk between mitochondria and NADPH oxidases," Free Radic Biol Med., Oct. 2011, 51: 1289-1301.
Dong et al., "Loss of FBP 1 by Snail-mediated repression provides metabolic advantages in basal-like breast cancer," Cancer Cell, Mar. 2013, 23: 316-331.
Dorr et al., "Synthetic lethal metabolic targeting of cellular senescence in cancer therapy," Nature, Sep. 2013, 501: 421-425.
Elstrom et al., "Akt stimulates aerobic glycolysis in cancer cells," Cancer Res, Jun. 2004, 64: 3892-3899.
Gerlinger and Swanton, "How Darwinian models inform therapeutic failure initiated by clonal heterogeneity in cancer medicine," Br .J Cancer, 2010, 103: 1139-1143.
Goldman et al., "Temporally sequenced anticancer drugs overcome adaptive resistance by targeting a vulnerable chemotherapy-induced phenotypic transition," Nature Communications, 2015, 6: 6139.
Gonzalez and McGraw, "The Akt kinases: isoform specificity in metabolism and cancer," Cell Cycle, Aug. 2009, 8: 2502-2508.
Guo et at, "Cross-resistance studies of isogenic drug-resistant breast tumor cell lines support recent clinical evidence suggesting that sensitivity to paclitaxel may be strongly compromised by prior doxorubicin exposure," Breast Cancer Res Treat, 2004, 85: 31-51.
Gupta et al., "Stochastic state transitions give rise to phenotypic equilibrium in populations of cancer cells," Cell, Aug. 2011, 146: 633-644.
Hartmann et al., "Hypoxia-induced up-regulation of angiogenin in human malignant melanoma," Cancer Res, Apr. 1999, 59: 1578-1583.
Heibein et al., "Role of aldo-keto reductases and other doxorubicin pharmacokinetic genes in doxorubicin resistance, DNA binding, and subcellular localization," BMC Cancer, 2012, 12: 381.
Hussein et al., "Glut-1 Expression Correlates with Basal-like Breast Cancer," Translational Oncology, Dec. 2011, 4: 321-327.
International Preliminary Report on Patentability in International Application No. PCT/US2015/023135, dated Sep. 27, 2016, 7 pages.
Jouanguy et al., "IL-12 and IFN-gamma in host defense against mycobacteria and *salmonella* in mice and men," Current Opinion in Immunology, Jun. 1999, 11: 346-351.
Kim et al., "Paclitaxel induces vascular endothelial growth factor expression through reactive oxygen species production," Pharmacology, 2008, 81: 317-324.
Kirk, "Targeted therapies: the maths behind combination therapy," Nat Rev Clin Oncol, Sep. 2013, 10: 488.
Kohn et al., "Expression of a constitutively active Akt Ser/Thr kinase in 3T3-L1 adipocytes stimulates glucose uptake and glucose transporter 4 translocation," J Biol Chem, 1996, 271: 31372-31378.
Kortylewski et al., "Regulation of the IL-23 and IL-12 balance by Stat3 signaling in the tumor microenvironment," Cancer Cell, Feb. 2009, 15:114-123.

Kostrzewa-Nowak, D. et al. "Bioreductive activation of mitoxantrone by NADPH cytochrome P450 reductase. Implications for increasing its ability to inhibit the growth of sensitive and multidrug resistant leukaemia HL60 cells." Cancer Lett 245, 252-262 (2007).
Kreso et al., "Self-renewal as a therapeutic target in human colorectal cancer," Nature Medicine, 2014, 20: 29-36.
Kreso et al., "Variable clonal repopulation dynamics influence chemotherapy response in colorectal cancer," Science, Feb. 2013, 339: 543-548.
Krishnamachary et at, "Hypoxia regulates CD44 and its variant isoforms through HIF-1 alpha in Aug. 2012, 7: e44078.triple negative breast cancer," PLoS One, Aug. 2012, 7: e44078.
Leder et al., "Mathematical modeling of PDGF-driven glioblastoma reveals optimized radiation dosing schedules," Cell, Jan. 2014, 156: 603-616.
Lee et at, "Akt-Dependent Metabolic Reprogramming Regulates Tumor Cell Histone Acetylation," Cell Metabolism, Aug. 2014, 20: 306-319.
Liu et al., "Metabolic regulation of cancer cell side population by glucose through activation of the Akt pathway," Cell Death and Differentiation, 2014, 21: 124-135.
Isakoff, "Triple-negative breast cancer: role of specific chemotherapy agents," Cancer J., 2010, 16: 53-61.
Majumder et al., "Predicting clinical response to anticancer drugs using an ex vivo platform that captures tumour heterogeneity," Nature Communications, 2015, 6:6169.
Martin et al., "The role of the CD44/ezrin complex in cancer metastasis," Critical Reviews in Oncology/Hematology, May 2003, 46: 165-186.
Marusyk et al., "Intra-tumour heterogeneity: a looking glass for cancer?," Nat Rev Cancer, 2012, 12: 323-334.
Meacham and Morrison, "Tumor heterogeneity and cancer cell plasticity," Nature, Sep. 2013, 501: 328-337.
Mehrara et al., "Specific growth rate versus doubling time for quantitative characterization of tumor growth rate," Cancer Res, 2007, 67: 3970-3975.
Miyawaki, "Visualization of the spatial and temporal dynamics of intracellular signaling," Dev Cell, Mar. 2003, 4: 295-305.
Mori et al., "Structural basis for CD44 recognition by ERM proteins," J Biol Chem, Oct. 2008, 283: 29602-29612.
Paggi et al., "The role of mitochondrial hexokinase in neoplastic phenotype and its sensitivity to lonidamine," Ann NY Acad Sci, Dec. 1988, 551: 358-360.
Phan et al., "Cancer metabolic reprogramming: importance, main features, and potentials for precise targeted anti-cancer therapies," Cancer Biology & Medicine, 2014, 11: 1-19.
Polimeni et al., "Modulation of doxorubicin resistance by the glucose-6-phosphate dehydrogenase activity," Biochem J, 2011, 439: 141-149.
Preuss et al., "Identification and characterization of novel human glucose-6-phosphate dehydrogenase inhibitors," Journal of Biomolecular Screening, Mar. 2013, 18: 286-297.
Riganti et at, "The pentose phosphate pathway: an antioxidant defense and a crossroad in tumor cell fate," Free Radic Biol Med., 2012, 53: 421-436.
Saini et al., "Targeting the PI3K/AKT/mTOR and Raf/MEK/ERK pathways in the treatment of breast cancer," Cancer Treat Rev., Dec. 2013, 39:935-46.
Scaife et al., "Nuclear Factor κB Inhibitors Induce Adhesion-dependent Colon Cancer Apoptosis," Cancer Res, 2002, 62: 6870-6878.
Seguin et al. "A β3 integrin-KRAS-RalB complex drives tumor sternness and resistance to EGFR inhibition," Nat Cell Biol, May 2014, 16: 457-468.
Sharma et al., "A chromatin-mediated reversible drug-tolerant state in cancer cell subpopulations," Cell, Apr. 2010,141: 69-80.
Su et al., "Mitochondrial uncoupling protein 2 regulates the effects of paclitaxel on Stat3 activation and cellular survival in lung cancer cells," Carcinogenesis, 2012, 33: 2065-2075.
Takeda et al., "The establishment of two paclitaxel-resistant prostate cancer cell lines and the mechanisms of paclitaxel resistance with two cell lines," The Prostate, 2007, 67: 955-967.

(56) References Cited

OTHER PUBLICATIONS

Takei et al., "Enhanced apoptotic reaction correlates with suppressed tumor glucose utilization after cytotoxic chemotherapy: use of 99mTc-Annexin V, 18F-FDG, and histologic evaluation," Journal of Nuclear Medicine, May 2005, 46: 794-799.
Tamada et al., "Modulation of glucose metabolism by CD44 contributes to antioxidant status and drug resistance in cancer cells," Cancer Res, 2012, 72: 1438-1448.
Tamm et al, "Hypoxia-induced interleukin-6 and interleukin-8 production is mediated by platelet-activating factor and platelet-derived growth factor in primary human lung cells," AmJ Respir Cell Mot Biol, Oct. 1998, 19: 653-661.
Valero and Hortobagyi, "Are anthracycline-taxane regimens the new standard of care in the treatment of metastatic breast cancer?," J Clin Oneal, 2003, 21: 959-962.
Villani et al., "Prevention of doxorubicin-induced cardiomyopathy by reduced glutathione," Cancer Chemother Pharmacol, Sep. 1991, 28: 365-369.
Walburg, "On the origin of cancer cells," Science, Feb. 1956, 123: 309-314.
Westman et al., "Bacterial inactivation of the anticancer drug doxombicin," Chemistry & Biology, Oct. 2012, 19: 1255-1264.
Wieman et al., "Cytokine stimulation promotes glucose uptake via phosphatidylinositol-3 kinase/Akt regulation of Glutl activity and trafficking," Mol Biol Cell, Apr. 2007, 18: 1437-1446.
Yagata et al., "Current strategy for triple-negative breast cancer: appropriate combination of surgery, radiation, and chemotherapy," Breast Cancer, Jul. 2011, 18: 165-173.
Zhao et al., "Targeting cellular metabolism to improve cancer therapeutics," Cell Death & Disease, 2013, 4: e532.
Zou et al., "2-NBDG as a fluorescent indicator for direct glucose uptake measurement," Journal of Biochemical and Biophysical Methods, Sep. 2005, 64: 207-215.
Bender et al., "P13K inhibitors prime neuroblastoma cells for chemotherapy by shifting the balance towards pro-apoptotic Bcl-2 proteins and enhanced mitochondrial apoptosis," Oncogene, Sep. 2010, 30: 494-503.
Del Bufalo and Zupi, "In vitro potentiation of epirubicin activity by lonidamine in a human breast cancer cell line," International Journal of Oncology, 1994, 4: 737-740.
Extended European Search Report in Application No. 15768447.3, dated Nov. 22, 2017, 18 pages.
Popert et al., "Relative cytotoxicities of adriamycin and epirubicin in combination with lonidamine against human bladder cancer cell lines," Urological Research, 1995, 22: 367-372.
Vivi et al., "Comparison of Action of the Anti-Neoplastic Drug Lonidamine on drug-sensitive and Drug-Resistant Human Breast Cancer Cells: 31P and 13C Nuclear Magnetic Resonance Studies", Breast Cancer Research and Treatment, Jan. 1997, 43: 15-25.
Zupi et al., "Adriamycin resistance modulation induced by lonidamine in human breast cancer cells," Anticancer Research, 1995, 15: 2469-2477.

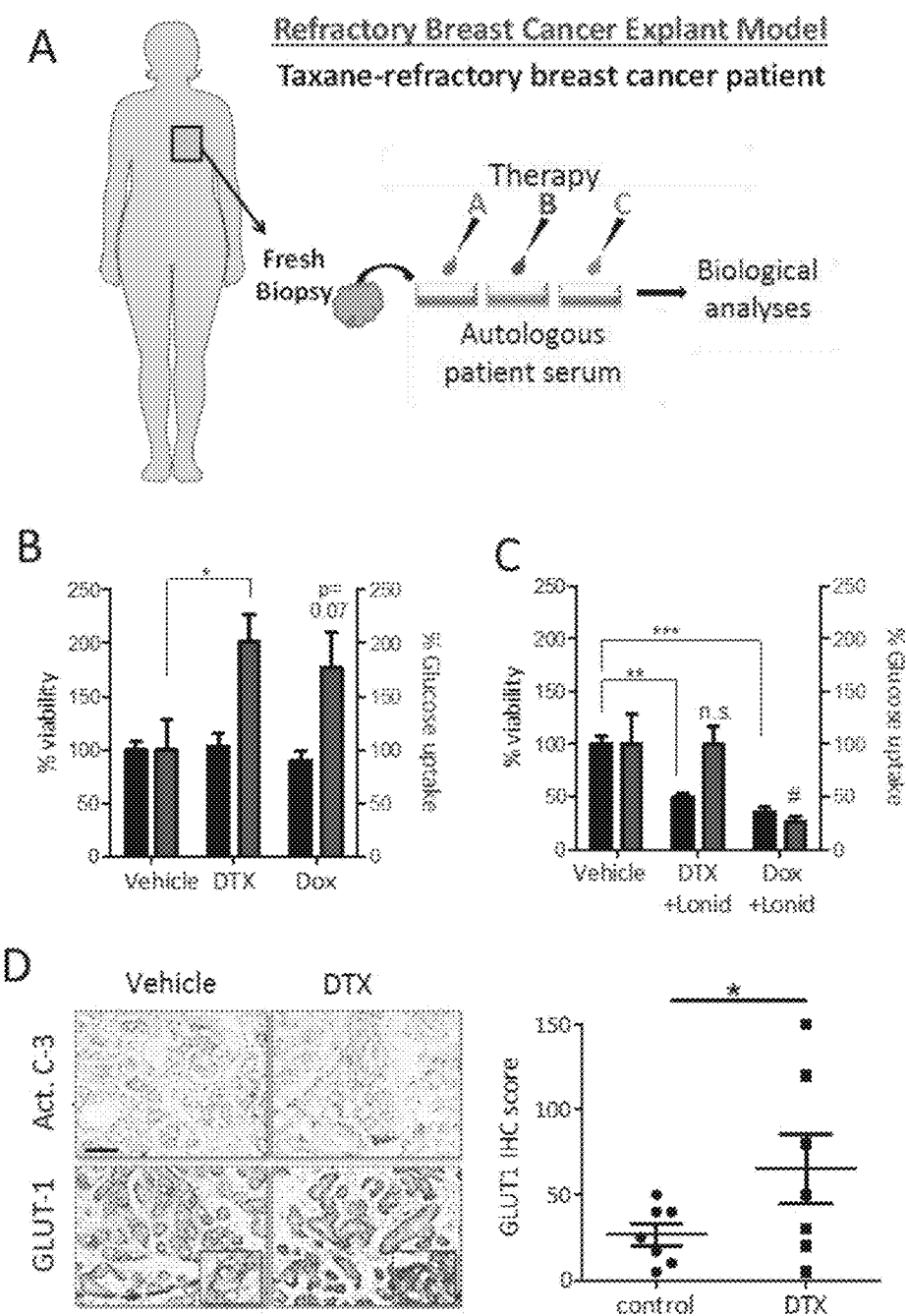
FIGs. 1A-D

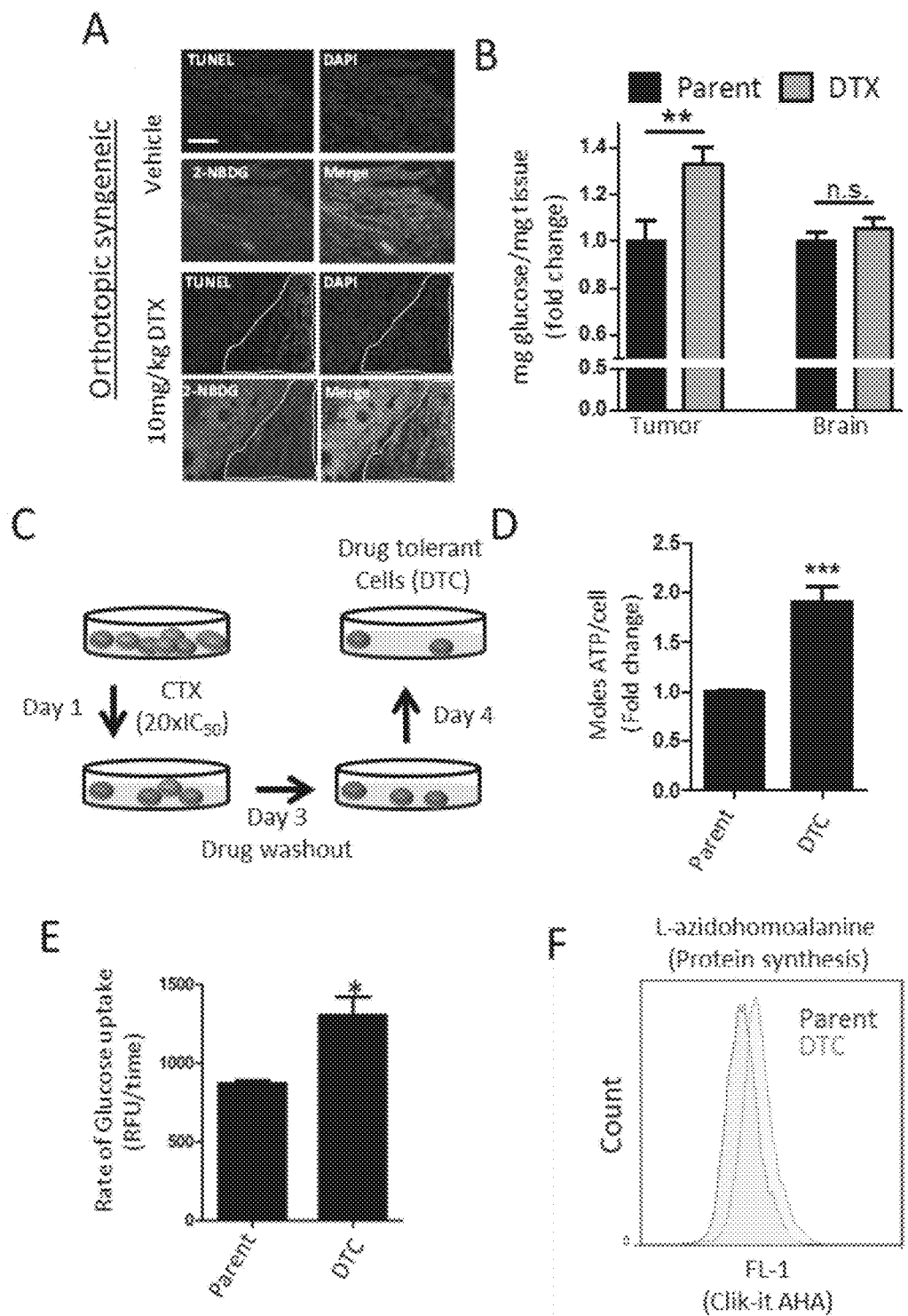
FIGs. 2A-F

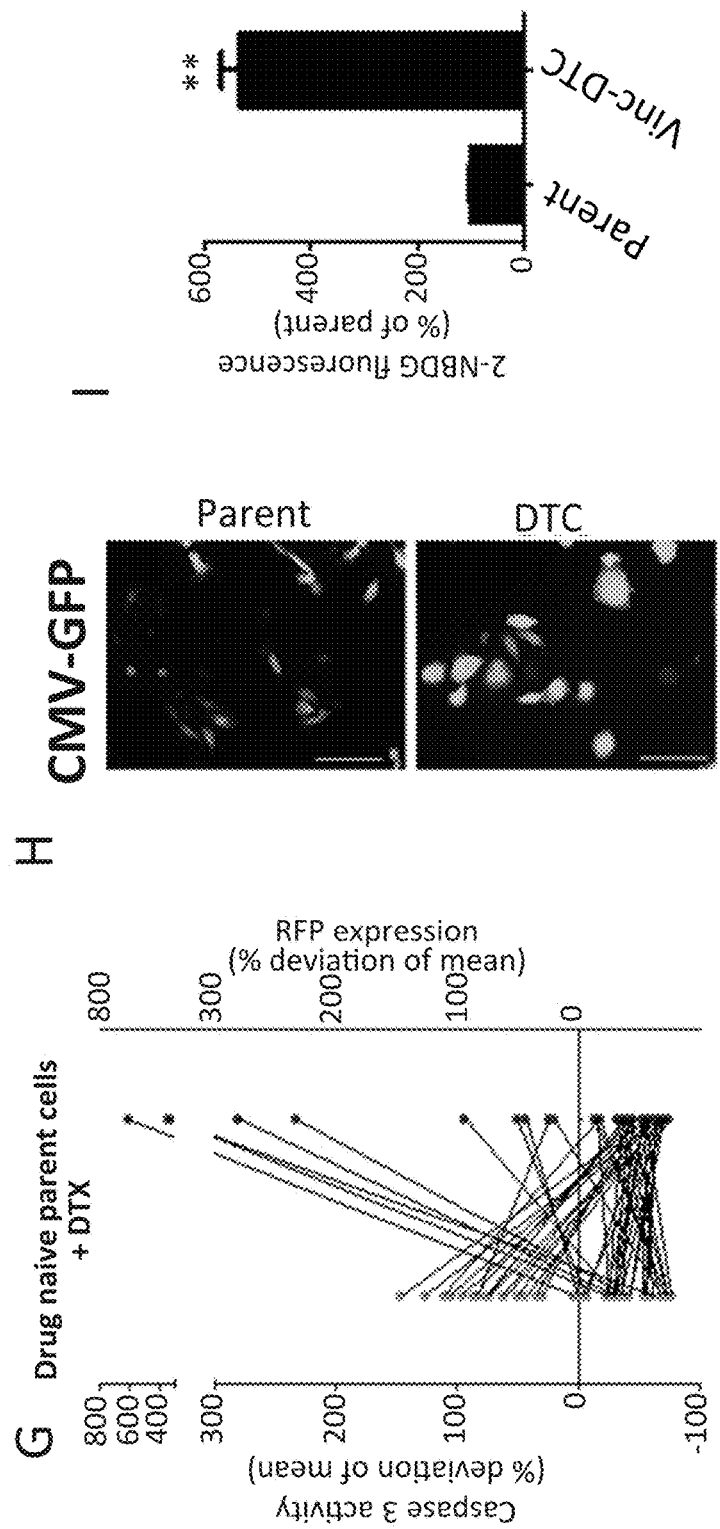
FIGs. 2G-I

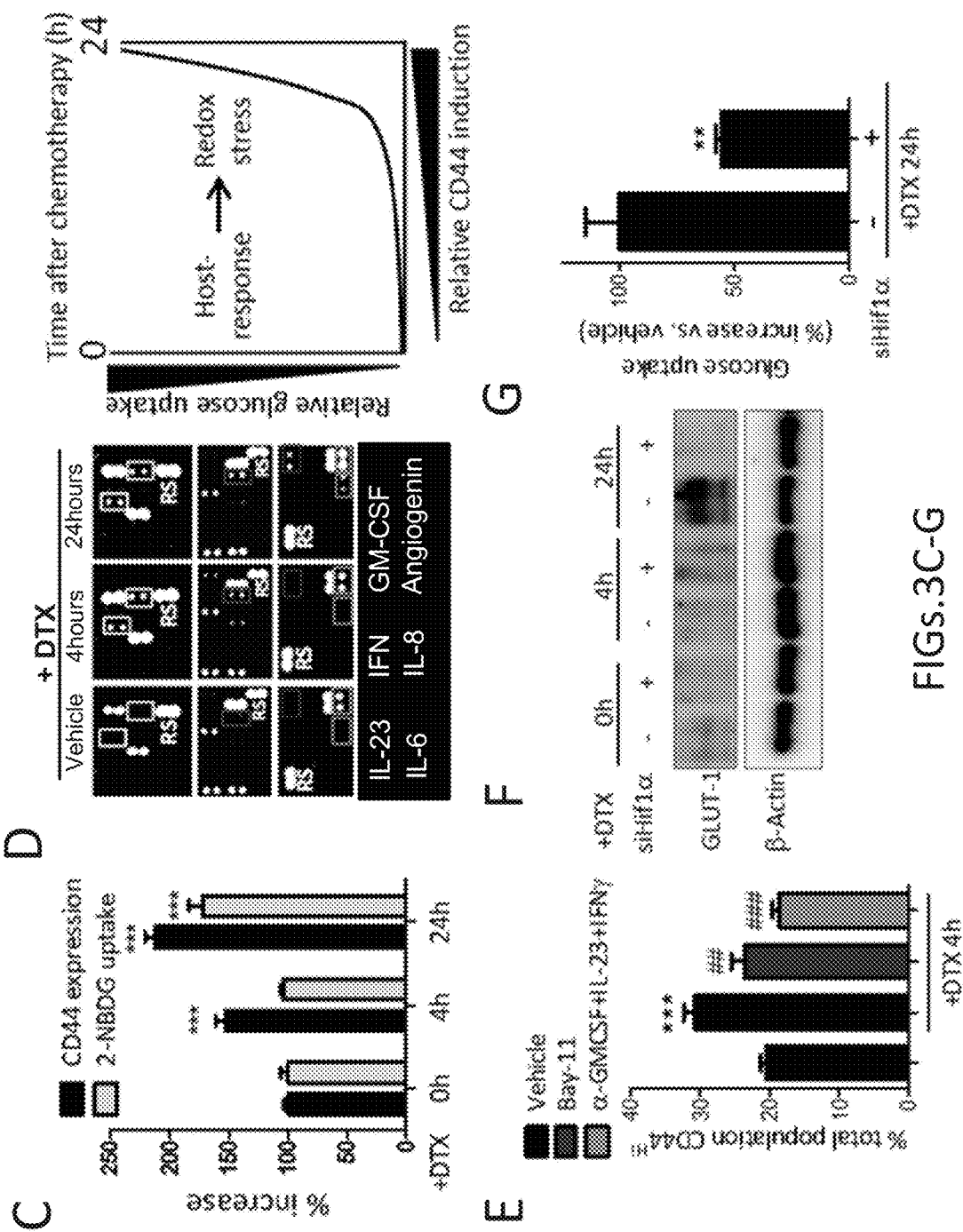
FIGs. 3C-G

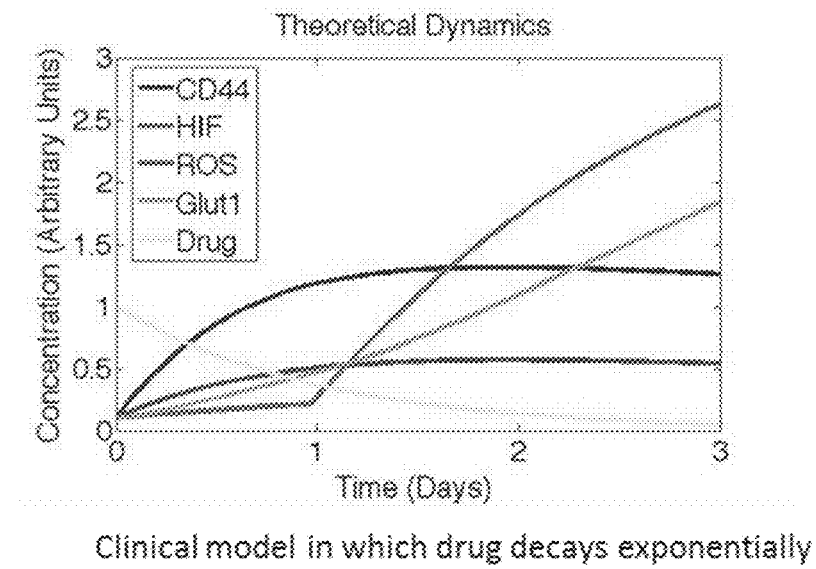
FIG. 3H
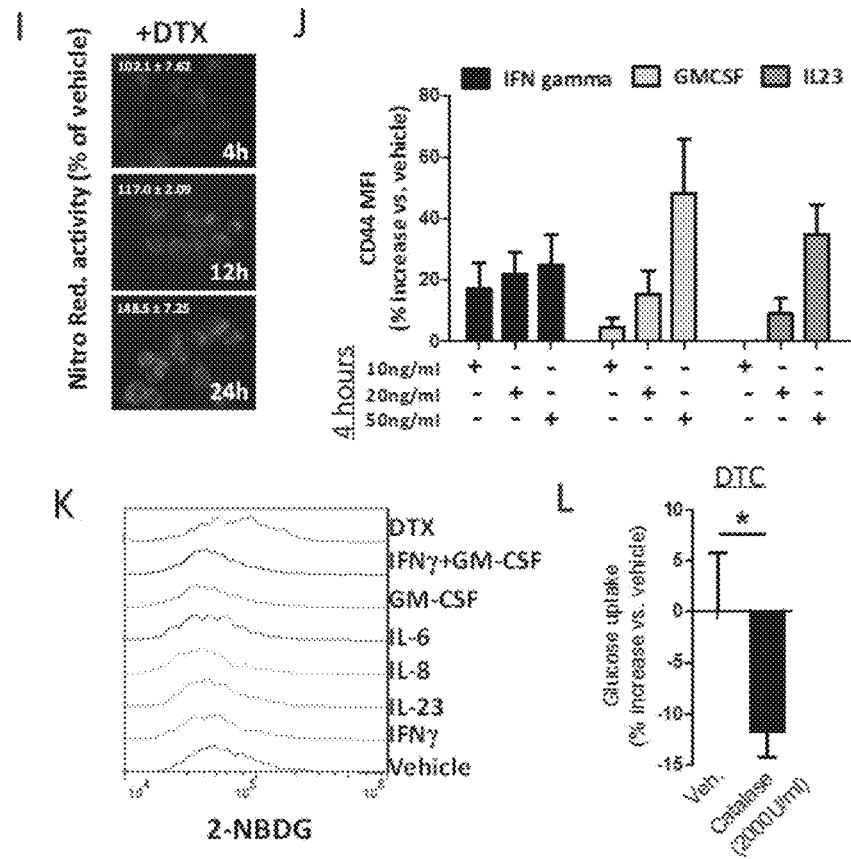
FIGs. 3I-L

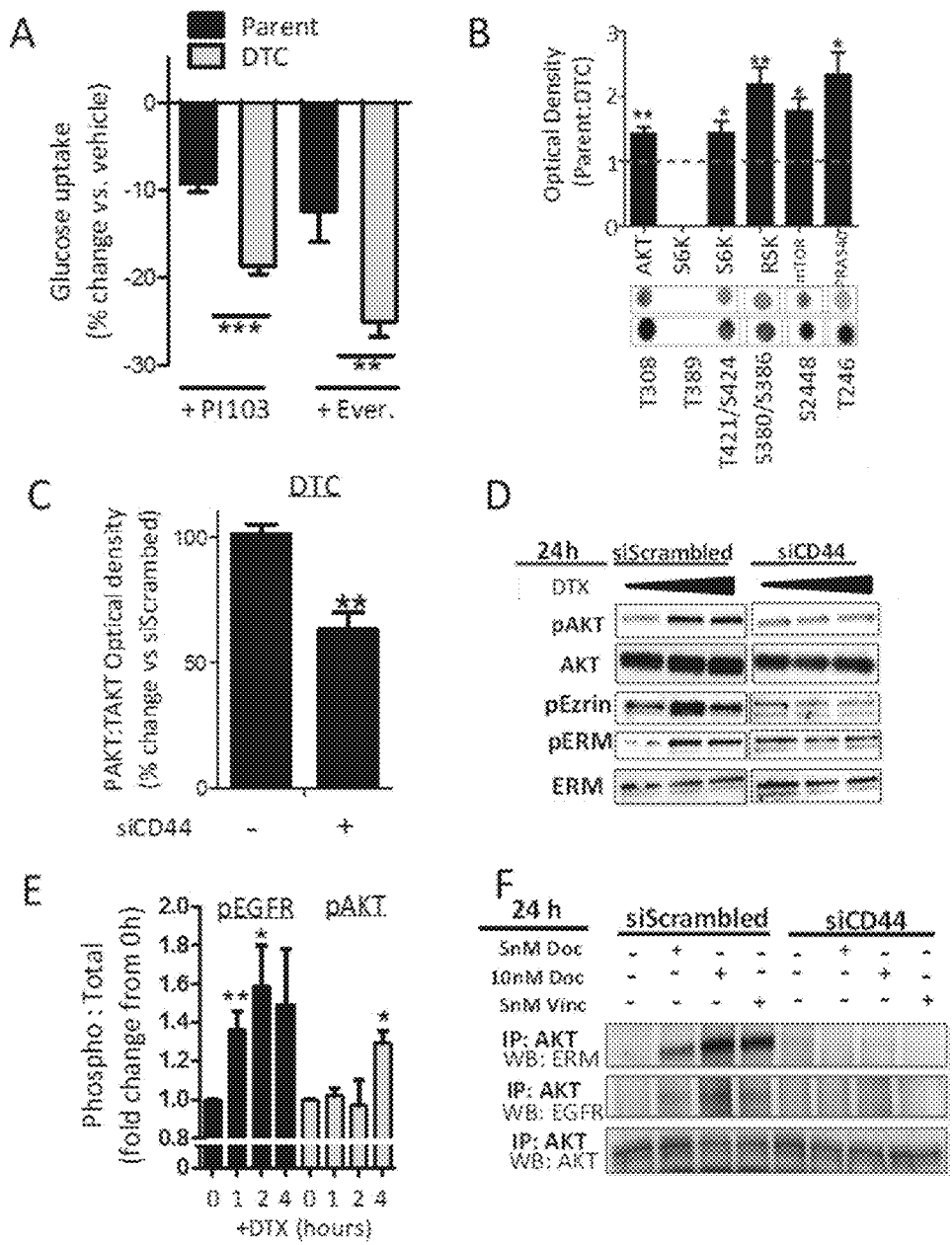
FIGs. 4A-F

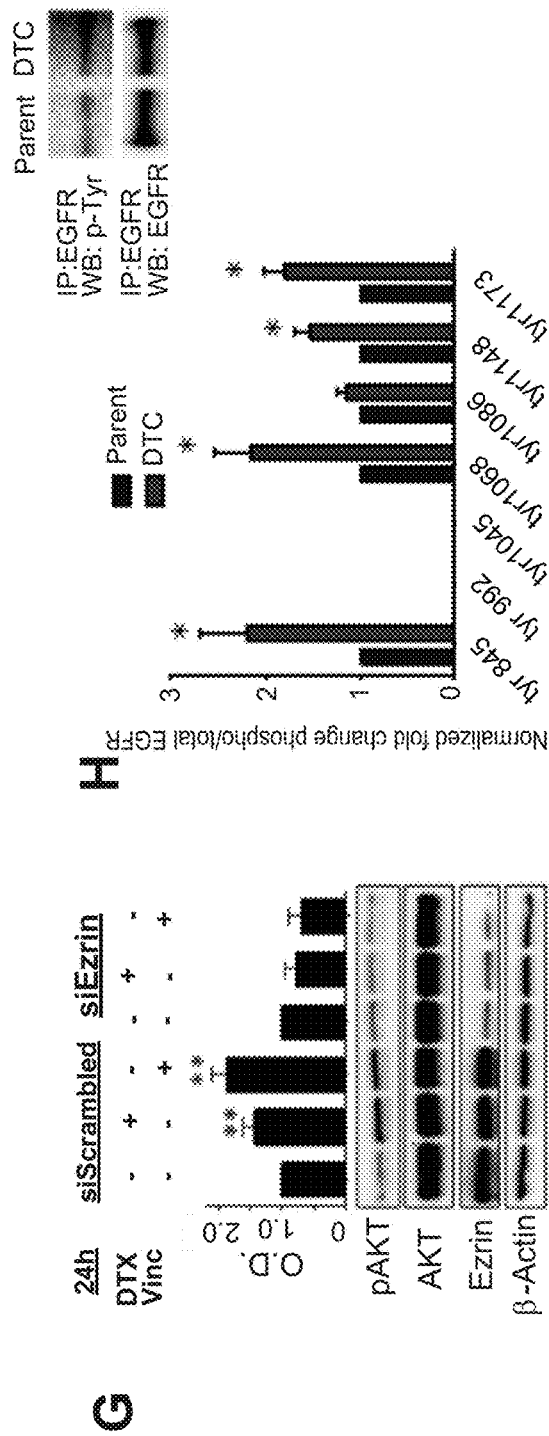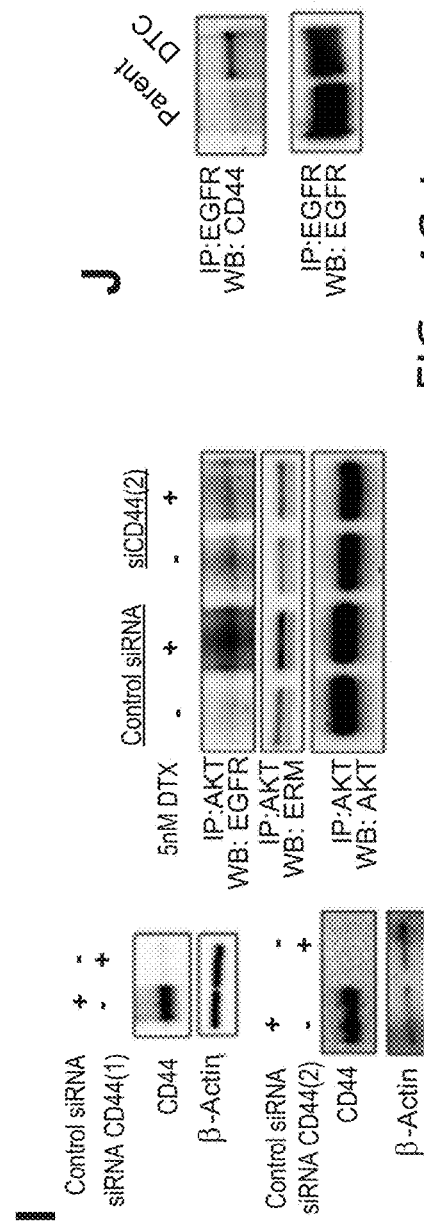
FIGs. 4G-J

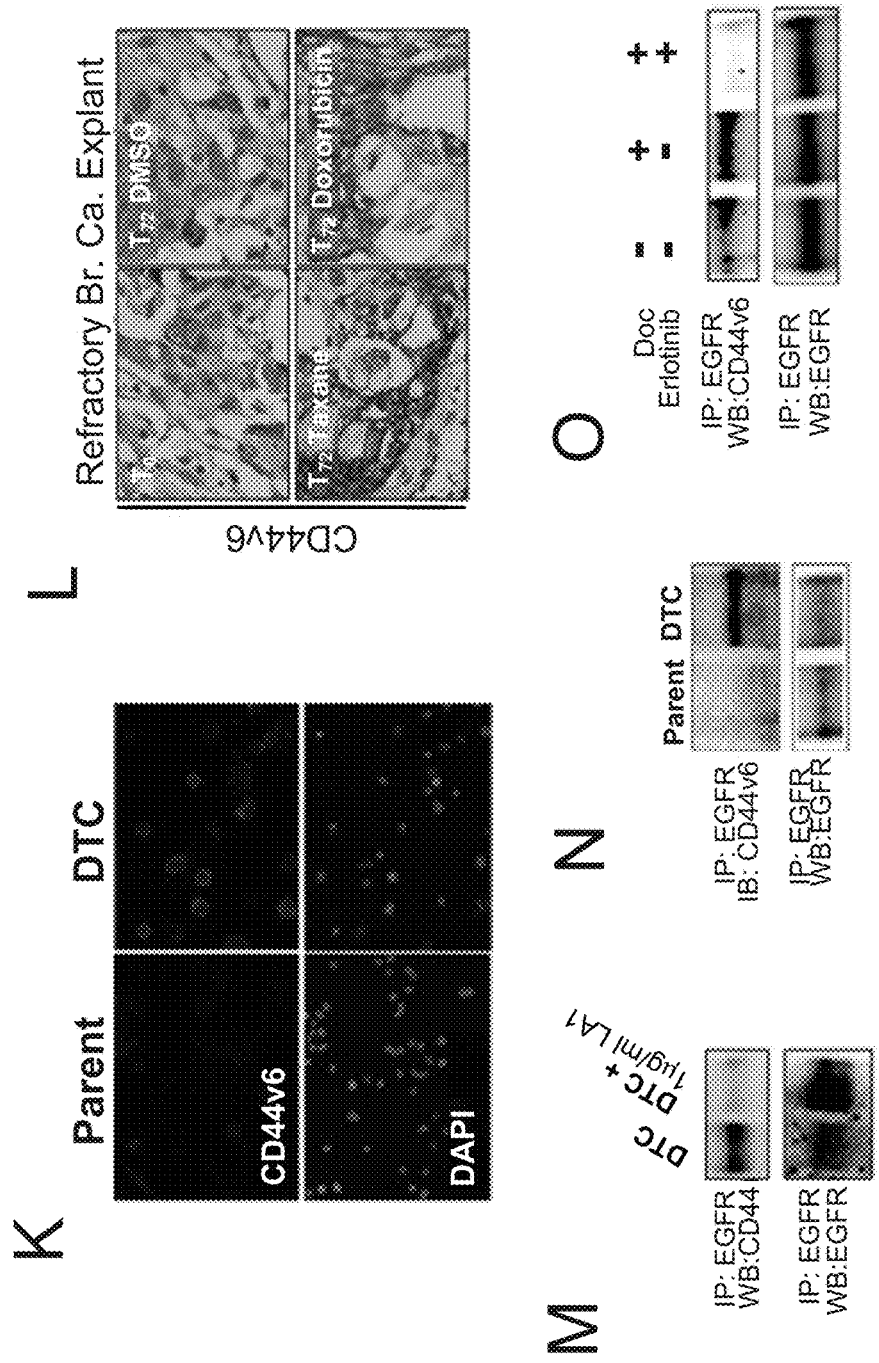
FIGs. 4K-O

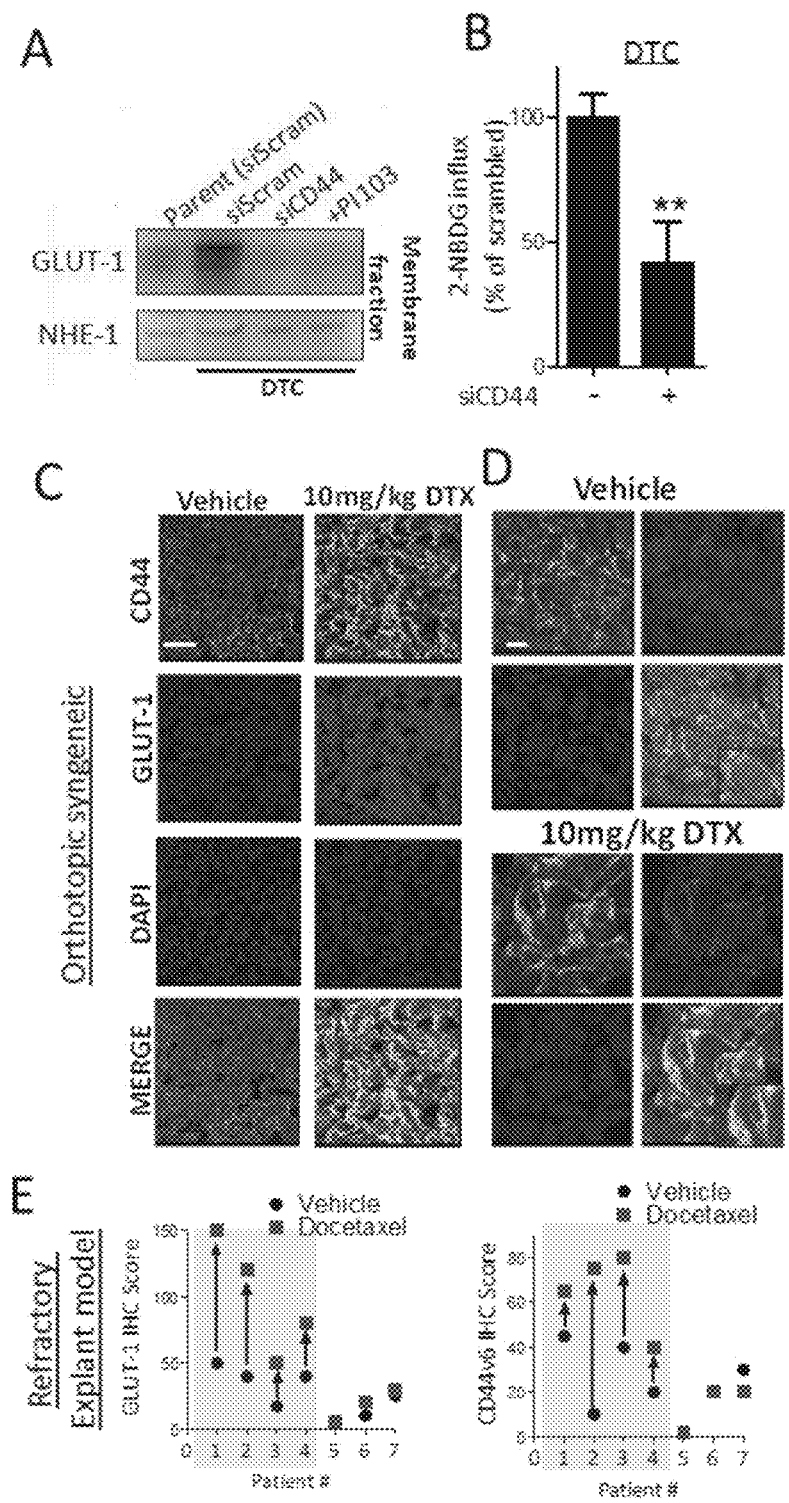
FIGs. 5A-E

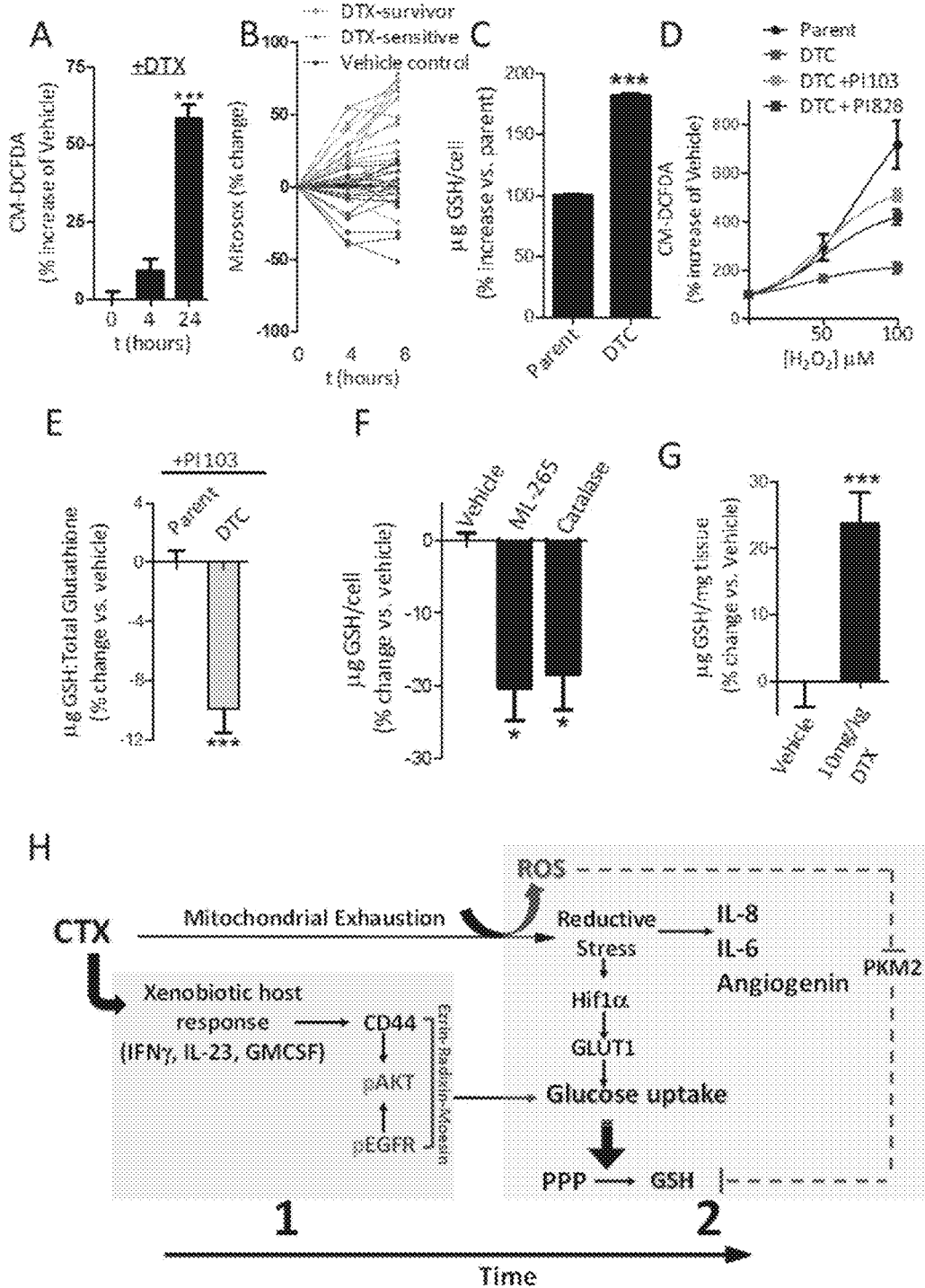
FIGs. 6A-H

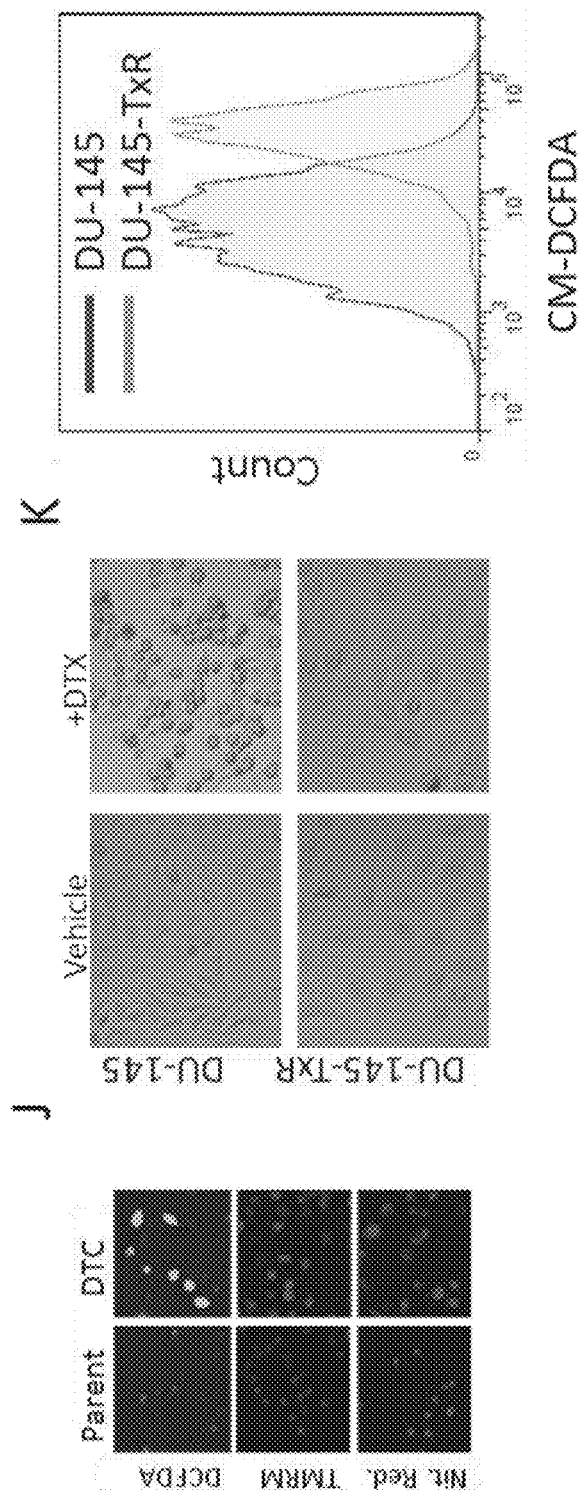
FIGs. 6I-K

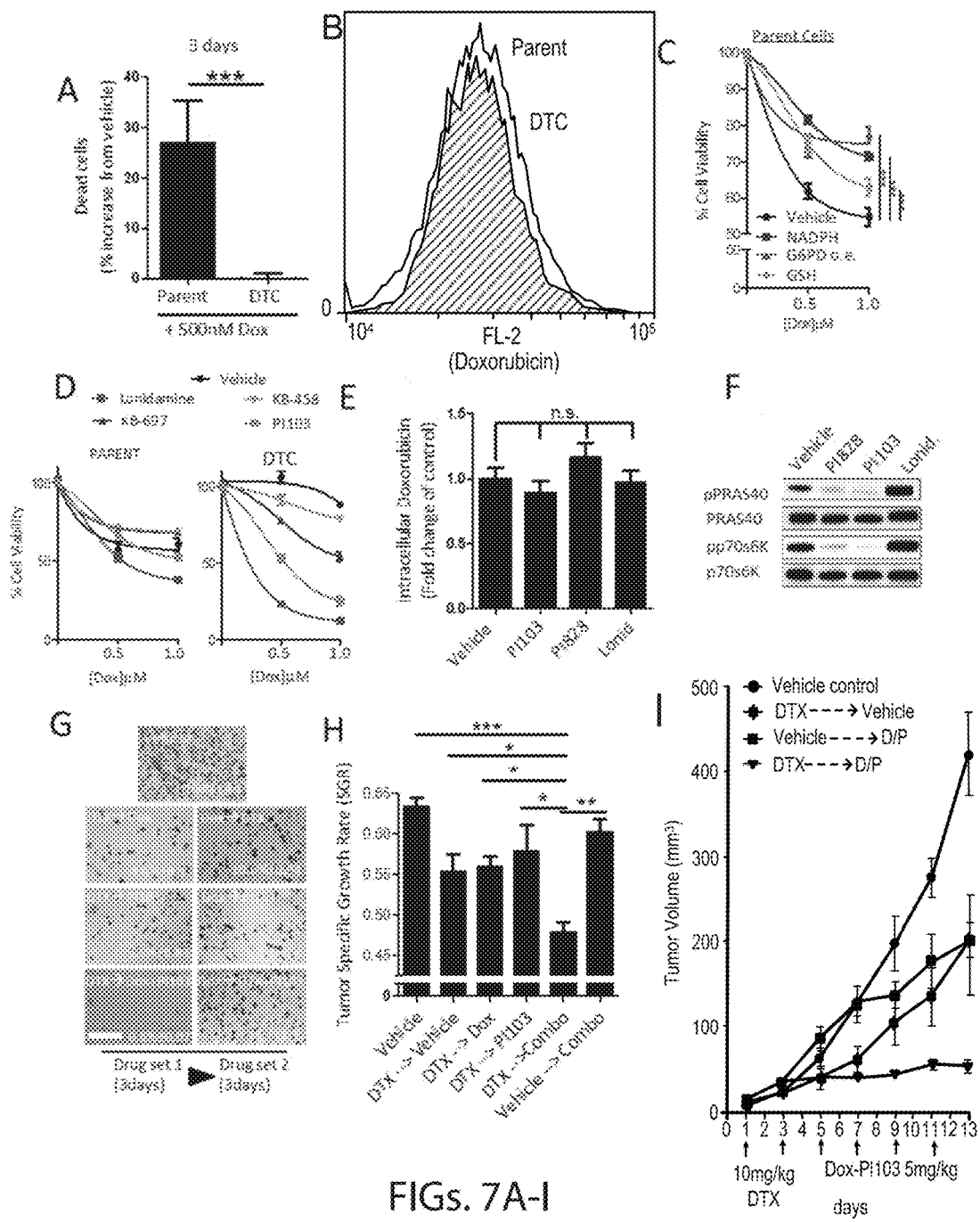
FIGs. 7A-I

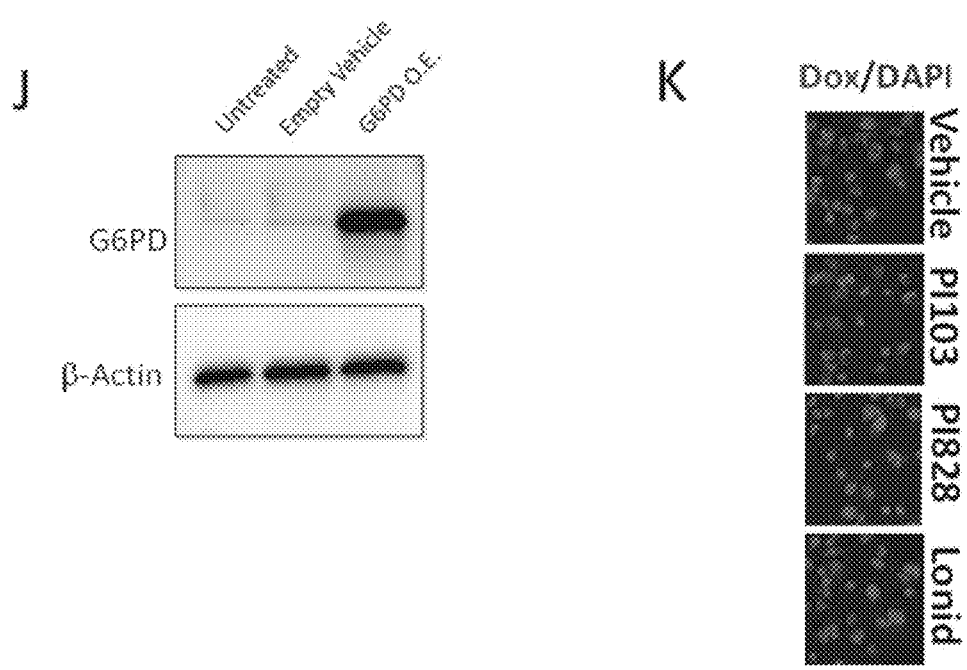
FIGs. 7J-K

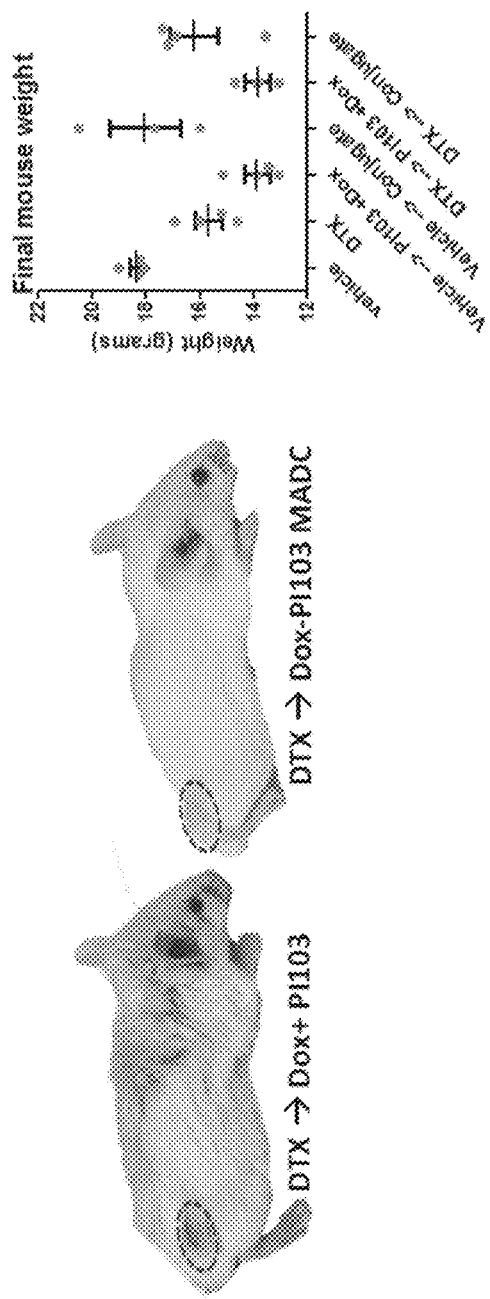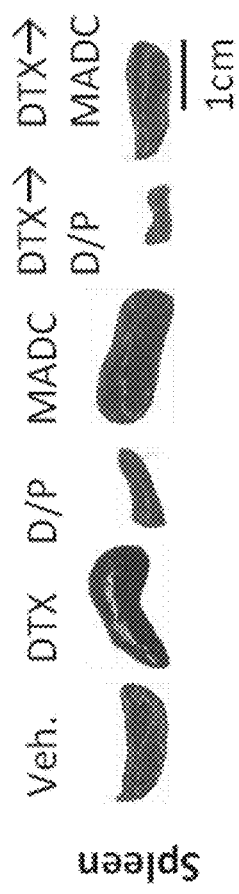
FIG. 8C
FIG. 8D

METABOLICALLY-ACTIVATED DRUG CONJUGATES TO OVERCOME RESISTANCE IN CANCER THERAPY

CLAIM OF PRIORITY

This application is a § 371 National Stage Application of PCT/US2015/023135, filed Mar. 27, 2015, which claims the benefit of U.S. Provisional Application Ser. No. 61/971,249, filed on Mar. 27, 2015. The entire contents of the foregoing are incorporated herein by reference.

FEDERALLY SPONSORED RESEARCH OR DEVELOPMENT

This invention was made with Government support under Grant No. WH0710482 awarded by the Department of Defense and Grant No. CA13524201 awarded by the National Institutes of Health. The Government has certain rights in the invention.

TECHNICAL FIELD

Described are combination therapies and metabolically-activated drug conjugates and their use in treating cancer in subjects.

BACKGROUND

It is increasingly appreciated that subclonal heterogeneity of tumors is the primary origin of therapy resistance and clinical relapse, events which invariably lead to mortality[1-4]. Emerging as a superior clinical strategy to address this challenge, clinicians employ combinations of small molecule pharmaceuticals that target multiple distinct subclonal variants at once[5-6]. For example, established anticancer drugs such as antimitotic microtubule-binding agents (Taxanes) delivered to patients in combination with DNA-intercalating anthracyclines (Doxorubicin) is a mainstay of systemic treatment for breast cancer patients in both the adjuvant and metastatic settings[7], even as first-line for aggressive subtypes such as triple negative breast cancer (TNBC) which is highly refractory to targeted therapies[8]. However, patients have endured variable clinical success with combination regimens despite the overwhelming catalog of anti-cancer drugs, evidence which has pinpointed both adaptive and cross-resistance as persisting therapeutic obstacles[9-10].

SUMMARY

Current strategies in the management of cancer often employ extremely toxic compounds (i.e. docetaxel and doxorubicin) which bring patients nearly to the brink of death in hopes of first destroying the cancer. While this strategy can be effective in some cases, it is an abrasive and caustic measure using antiquated technologies.

In the present study a systems biology approach was used to map the molecular events underlying metabolic plasticity in cancer cells which acquire tolerance to a primary therapy. In doing so, it was unexpectedly discovered that a temporal coordination of molecular events is conferred to mediate cross therapy-resistance which unmasked a target for temporally-sequenced combination therapies. Upon exposure to taxane chemotherapy, activation of an early-established signaling network was observed which was required to mediate a delayed metabolic transposition driving resistance to anthracyclines. The application of chemotherapy unlocks/uncovers vulnerabilities that are intrinsic in the drug tolerant population; pharmacologic ablation of metabolic dysfunction resulted in the exposure of inherent vulnerabilities to anthracyclines.

A major translational goal of the study was to exploit drug resistant features as a target for novel therapies which can accomplish two tasks: 1. harness the intracellular microenvironment induced in drug tolerant cancer cells, and 2. introduce combination regimens which synergize efficacy majorly in residual tumor populations. Thus, a drug-drug conjugate was designed that includes an AKT inhibitor (e.g., PI103) and an anthracycline anticancer compound (e.g., doxorubicin), linked with a metabolically-activated hinge to focus release in a confined region of 'favored environment', e.g., enhanced intratumoral glutathione (GSH). And with the knowledge of event-ordering from the systems modeling, temporally-sequenced combination therapies of established targeted and cytotoxic agents which harnessed the vulnerabilities created by metabolic reprogramming were designed.

Thus, provided herein are metabolically-activated drug conjugates comprising: (i) an inhibitor of glycolysis or an inhibitor of phosphatidylinositol 3-kinase/protein kinase-B/ mammalian target of rapamycin (PI3K/AKT/mTOR) signaling; and (ii) a drug whose activity is suppressed by metabolic intermediates, e.g., an anthracycline or nucleoside analog; wherein (i) and (ii) are linked together via a disulfide linker. In some embodiments, the inhibitor of PI3K/AKT/ mTOR signaling is selected from the group consisting of PI3kinase inhibitors; mTOR inhibitors; and AKT inhibitors.

In some embodiments, the inhibitor of PI3K/AKT/mTOR signaling is PI103.

In some embodiments, the anthracycline is doxorubicin.

In some embodiments, the nucleoside analog is gemcitabine.

In some embodiments, the inhibitor of glycolysis is an inhibitor of Glucose-6-phosphate dehydrogenase (G6PD), hexokinase, 6-phosphofructo-2-kinase/fructose-2,6-biphosphatase 3 (PFKFB3), or a glucose transporter.

In some embodiments, the metabolically-activated drug conjugate has the structure:

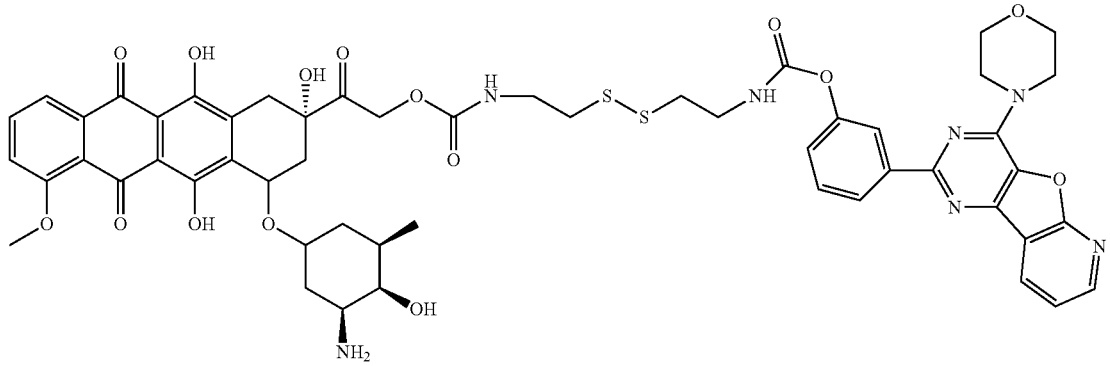 [SMILES: COc1cccc2c1C(=O)c1c(O)c3c(c(O)c1C2=O)C[C@@](O)(C(=O)COC(=O)NCCSSCCNC(=O)Oc1cccc(-c2nc(N4CCOCC4)c4oc5ncccc5c4n2)c1)CC3OC1C[C@@H](C)[C@@H](O)[C@@H](N)C1]

Also provided herein are the metabolically-activated drug conjugates described herein for use in a method of treating cancer in a subject, or for use in the manufacture of a medicament for the treatment of cancer.

In some embodiments, the cancer in the subject is drug resistant, e.g., is resistant to treatment with a cytotoxic drug, e.g., has acquired acutely-induced drug resistance through non-mutational mechanisms, e.g., has demonstrated a plateau in growth after treatment with the drug.

Also provided herein are methods for treating a subject who has drug-resistant cancer, comprising administering to the subject a metabolically-activated drug conjugate described herein. In some embodiments, the cancer is resistant to a cytotoxic agent.

Further provided herein are methods for treating a subject who has cancer that include administering a round of induction therapy, wherein the round of induction therapy comprises administration of an amount of a cytotoxic agent or radiation therapy sufficient to increase glucose uptake or induce drug resistance in the cancer cells; and administering a therapeutically effective amount of a metabolically-activated drug conjugate described herein.

Also provided herein are methods for treating a subject who has drug-resistant cancer comprising administering to the subject a therapeutically effective amount of a combination therapy comprising (i) an inhibitor of glycolysis or an inhibitor of phosphatidylinositol 3-kinase/protein kinase-B/mammalian target of rapamycin (PI3K/AKT/mTOR) signaling and (ii) a cytotoxic agent. In some embodiments, the cancer is resistant to a first cytotoxic agent, and the cytotoxic agent of (ii) is a second cytotoxic agent.

In addition, provided herein are methods for treating a subject who has cancer including administering to the subject a first round of treatment comprising an induction therapy that induces a metabolic change in the cells of the cancer, e.g., increased glucose uptake, e.g., associated with acquisition of non-mutational drug resistance, wherein the induction therapy comprises administration of an amount of a first cytotoxic agent or radiation therapy sufficient to induce drug resistance in the cancer cells; and administering a second round of treatment comprising a metabolic inhibitor and s second cytotoxic agent.

In some embodiments, the metabolic inhibitor is an inhibitor of glycolysis or an inhibitor of phosphatidylinositol 3-kinase/protein kinase-B/mammalian target of rapamycin (PI3K/AKT/mTOR) signaling.

Additionally provided herein are methods for treating a subject who has cancer comprising administering a round of induction therapy, wherein the round of induction therapy comprises administration of an amount of a first cytotoxic agent or radiation therapy, sufficient to induce drug resistance in the cancer cells; and administering a therapeutically effective amount of a combination therapy comprising (i) an inhibitor glycolysis or an inhibitor of phosphatidylinositol 3-kinase/protein kinase-B/mammalian target of rapamycin (PI3K/AKT/mTOR) signaling and (ii) a second cytotoxic agent.

In some embodiments of the methods described herein, the inhibitor of PI3K/AKT/mTOR signaling is selected from the group consisting of PI3kinase inhibitors; glucose-6-phosphate dehydogenase (G6PD) hexokinase inhibitors; mTOR inhibitors; and AKT inhibitors, maybe even glut-transport inhibitors. In some embodiments, the inhibitor of PI3K/AKT/mTOR signaling is PI103.

In some embodiments of the methods described herein, the second cytotoxic agent is not the same as the first cytotoxic agent.

In some embodiments of the methods described herein, the second cytotoxic agent is a drug whose activity is suppressed by metabolic intermediates, e.g., an anthracycline (e.g., doxorubicin) or nucleoside analog (e.g., gemcitabine).

In some embodiments of the methods described herein, the combination therapy or metabolically-activated drug conjugate is administered within about 24-240 hours after a final dose of the round of induction therapy.

In some embodiments of the methods described herein, the drug resistance is acutely-induced non-mutational drug resistance.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 1A-D. Induction of glycolytic features underlies a chemoresistant phenotype in human refractory tissue A) Schematic illustrates human refractory breast cancer explant model.

Figure 3A:
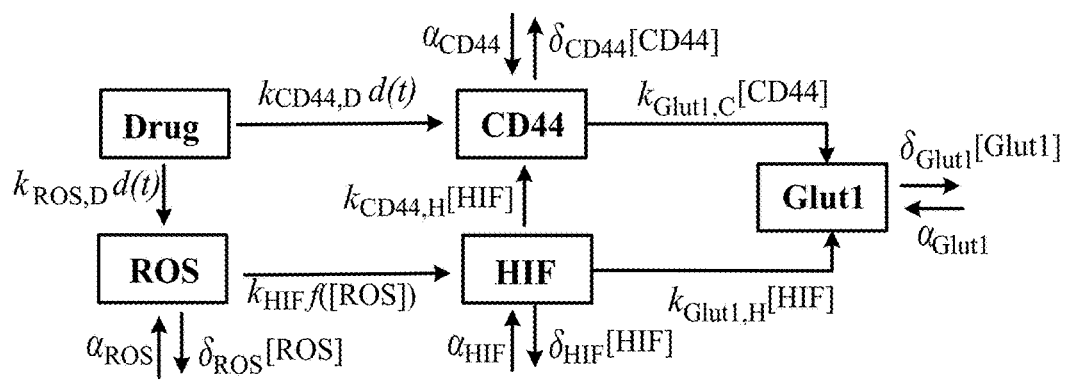

B) Cell viability analyses (left panel) or glucose uptake (right panel) of explant tumor tissue following incubation with vehicle or chemotherapy (72 h). N=3 Error bars indicate SEM.

C) Cell viability analyses (left panel) or glucose uptake (right panel) of explant tumor tissue following incubation with chemotherapy in the presence of hexokinase inhibition (Lonid.) (72 h). N=3 Error bars indicate SEM.

D) IHC of GLUT-1 in explant tumor tissue treated with vehicle or docetaxel, right panel indicates histologic quantification of GLUT-1 staining intensity (IHC score) N=7 ($*p<0.05$).

FIGS. 2A-I. A glycolytic phenotype characterizes chemotherapy tolerant cancer cells A) Representative image from confocal microscopy of tumor sections from a syngeneic mammary carcinoma model (treated Vehicle or docetaxel [DTX]), evaluating uptake of glucose (2NBDG, green signal) with indication of apoptosis (TUNEL positive, red signal).

B) Total glucose levels from brain and tumor tissue homogenate taken from mice treated with vehicle or DTX (10 mg/kg i.t., 7 hours). N=6 per group, error bars indicate SEM, $**p<0.01$.

C) Schematic illustrates the generation of drug tolerant cells from 2-dimensional cell culture. Adherent population was considered the drug tolerant cell subset (DTC).

D) Intracellular ATP of MDA-MB-231 parent cells or DTC, values are expressed as fold change of parent. N>10, error bars indicate SEM, $***p<0.001$ E) Rate of 2-NBDG (glucose) uptake (fluorescence/30 min) evaluated in MDA-MB-231 parent or DTC determined by fluorescence activated cell sorting (FACS). N>5, error bars indicate SEM $*p<0.05$.

F) Representative histogram from FACS analysis indicates rate of protein translation determined by click-reactive methionine in MDA-MB-231 parent or DTC.

G) Single cell quantification of RFP expression and caspase-3 activity determined by fluorescent microscopy. MDA-MB-231 cells transfected with a CMV promoter-driven RFP were incubated with toxic dose of DTX for 24 hours (50 nM) and subsequently fixed and immunostained to detect caspase-3 activity (FITC). Individual cells were analyzed for expression level of RFP or caspase 3 activity. Values shown are % change from the overall mean of each signal.

H) Fluorescent microscopy of GFP from MDA-MB-231 parent or DTC transfected with a CMV promoter-controlled GFP. Scale bar=50 um I) Glucose uptake determined by 2-NBDG fluorescence from FACS analysis. MDA-MB-231 cells were treated with vehicle or DTC were generated using 100 nM vincristine (DTC-Vinc) as described in FIG. 2C.

FIGS. 3A-L. Dynamic phenotypic heterogeneity and glycolytic plasticity occur in temporally and mechanistically-distinct manners A) Systems biology depiction, showing modeled interactions encompassing CD44, GLUT1, HIF1a and reactive oxygen species (ROS)

B) Simulated temporal kinetics of molecular dynamics in the case where drug concentration in the system remains constant over time. FIG. 3H shows clinically-relevant kinetics in which exponential decay of drug is assumed.

C) Quantification of cell surface CD44 expression (black bars) or glucose uptake (grey bars) in MDA-MB-231 exposed to docetaxel (DTX, 25 nM) for 4 h and 24 h determined by FACS N=5, ***$p<0.001$.

D) High-density cytokine/chemokine immunoarray of parent MDA-MB-231 cells treated with DTX (25 nM) for 4 h and 24 h N=4. Right panel schematic summarizes kinetic changes in CD44 expression and glucose uptake as a function of docetaxel exposure. Increasing time of exposure correlates with change from cell host-response to redox-related cytokines.

E) Quantification of surface membrane CD44 expression on MDA-MB-231 cells exposed to DTX (25 nM, 4 h)+/− NFkappaB inhibitor, Bay-11 (10 μM) or neutralizing antibodies (2 μg/ml). N=5, ***$p<0.001$.

F) Representative western blot analysis of GLUT-1 expression in MDA-MB-231 parent cells treated with DTX (25 nM), prior to treatment cells were transfected with siRNA targeting HIF1A or scrambled control.

G) Glucose uptake (2-NBDG) determined by FACS in MDA-MB-231 cells which were exposed to DTX (25 nM, 24 h). Prior to analysis, cells were transfected with siRNA targeting HIF1A or scrambled control. N=5 **$p<0.01$.

H) Theoretical kinetic variations of proteins in a 'clinical scenario' in which drug load is decreased exponentially over time. In-vitro scenario can be found in main FIG. 3B which corresponds similar temporal event-ordering.

I) Fluorescent microscopy of nitroreductase activity in MDA-MB-231 cells treated with sub-lethal dose of docetaxel (25 nM). Real-time assessment of activity was determined at 4 h, 12 h and 24 h. Relative fluorescence was quantified and expressed as % increase from time 0±SEM J) FACS analysis of CD44 cell surface expression on MDA-MB-231 treated with indicated cytokines for 4 hours and expressed as the mean fluorescent intensity % increase from the vehicle control group. Error bars indicate SEM.

K) Histogram shows glucose uptake (2-NBDG) in MDA-MB-231 parent cells following 24 hour incubation with indicated cytokines (50 ng/ml) or docetaxel (DTX) (24 h). Determined by FACS analysis.

L) Glucose uptake (2-NBDG) determined by FACS analysis in MDA-MB-231 DTC following incubation with Catalase for 6 hours or a vehicle control. Error bars indicate SEM *$p<0.05$ FIGS. 4A-O. CD44 cortex-scaffolding drives glucose uptake via PI3K-AKT signaling-axis in chemotherapy tolerant cancer cells A) Glucose uptake (2-NBDG) in MDA-MB-231 parent or DTC following incubation with AKT inhibitor (PI103) or mTORC1 inhibitor (Everolimus) (3 h). Values expressed as % suppression of glucose uptake compared to a vehicle-treated control. N>4, *$p<0.001$ $p<0.01$.

B) Quantification of phosphorylated AKT-family proteins in MDA-MB-231 parent or DTC. Values indicate activated residues determined by optical density (O.D.) from immunoarray and expressed as a ratio of DTC:Parent N=4 *$p<0.05$ **$p<0.01$.

C) Quantification of activated AKT (Ser473) in MDA-MB-231 DTC generated from cells transfected with siRNA targeting CD44 or a scrambled control (N=4). **$p<0.01$ D) Representative western blot of phosphorylated and total AKT, Ezrin and ERM protein levels in MDA-MB-231 cells transfected with siRNA targeting CD44 or scrambled control following exposure to DTX (25 nM, 24 h).

E) Histogram shows quantification of phosphorylated AKT or EGF cell surface receptor 1 (EGFR) in MDA-MB-231 treated with DTX (25 nM) for indicated amount of time. N=4, *$p<0.05$ **$p<0.01$ F) Representative western blot indicates immunocomplexes of AKT in MDA-MB-231 cells following exposure to docetaxel (DTX) or vincristine (vinc.) 24 h. Prior to drug treatment cells were transfected with siRNA targeting CD44 (24 h).

G) Western blot analysis of indicated active and total protein levels induced by sub-lethal DTX (10 nM) and vincristine (5 nM) (24 h) in MDA-MB-231 parent cells transfected with siRNA targeting Ezrin or a scrambled control. Upper panel indicates quantification of the O.D. phospho:total AKT. N=3 **$p<0.01$.

H) Histogram shows quantification from EGFR phosphorylation determined between MDA-MB-468 parent group and DTC. Error bars indicate SEM *$p<0.05$. Western blot inset indicates immunocomplexes of EGFR with total phospho-tyrosine. EGFR as loading control.

I) Confirmation of CD44 knockdown (siRNA #1 and #2) validated by western blot between siRNA and scrambled control group. Representative western blot shows immunocomplex formed between AKT, EGFR and ERM in MDA-MB-231 parent cells treated with docetaxel (24 h). Confirmation of immunocomplexes observed from FIG. 4F.

J) Representative western blot shows immunocomplex formed between EGFR and CD44 in MDA-MB-231 parent cells or a DTC group. Total EGFR as loading control.

K) Fluorescent microscopy of CD44v6 in MDA-MB-231 parent or DTC.

L) Representative IHC of CD44v6 from the human breast cancer explant model (described by schematic in main FIG. 1A) following treatment with docetaxel or doxorubicin.

M) Immunocomplex formed between CD44 and EGFR of MDA-MB-231 DTC is abolished by incubation with anti-EGFR monoclonal neutralizing antibody LA1 (24 h).

N) Immunocomplex formed between CD44v6 and EGFR in MDA-MB-231 parent and DTC confirms the relationship between these proteins in drug tolerant cells.

O) Representative western blot shows immunocomplex between CD44v6 and EGFR in MDA-MB-231 cells is induced by treatment with docetaxel at sublethal dose (10 nM) while addition of EGFR inhibitor erlotinib reverses this interaction.

FIGS. 5A-E. CD44 localizes cell membrane GLUT-1 in chemotherapy tolerant cancer cells and tissue in a PI3K/AKT-dependent manner A) Representative western blot from subcellular fractionation shows membrane localization of GLUT-1 in MDA-MB-231 parent or DTC±PI103 (8 h). Prior to drug treatment cells were transfected with siRNA targeting CD44 or scrambled control as indicated.

B) Glucose uptake (2-NBDG) in MDA-MB-231 DTC generated from a population of parent cells transfected with siRNA targeting CD44 or a scrambled control. N=5, **p<0.01.

C) Representative confocal microscopy shows total CD44 and GLUT-1 expression in tumor tissue isolated from a syngeneic orthotopic mammary carcinoma model (4T-1) 72 hours following i.v. injection with vehicle or DTX (10 mg/kg). Images are representative of the overall increase in signal intensity from confocal microscopy, N=3 per group.

D) Co-localization of CD44 and GLUT-1 was evaluated by confocal microscopy in tumor tissue isolated as described in 5C. Equalizing the fluorescence intensity between immunohistochemical slides from vehicle and DTX-treated tumor sections was achieved using unequal gain parameters from confocal imaging, a detection limit set beyond an isotype control, N=3 per group.

E) Human tumor explant tissue was evaluated for expression of GLUT1 and variant isoform 6 of CD44 (v6). Patient samples in which induction of GLUT1 was observed correlated to induction of CD44v6 (red transparent box).

FIGS. 6A-K. Temporal dynamics underlie an ROS-mediated pentose phosphate pathway (PPP) shunt and augmented antioxidant phenotype in chemotherapy tolerant cancer cells A) CM-DCFDA loaded MDA-MB-231 cells were measured by FACS to detect total cell reactive oxygen species following incubation with DTX (25 nM) at indicated time points. N=5 ***p<0.001 by ANOVA.

B) Real-time single cell tracing of MDA-MB-231 cells pre-loaded with mitosox were tracked following exposure with lethal concentration of DTX (50 nM). Mitosox fluorescence was evaluated in cells which remained viable at 12 h post-chemotherapy (green lines) or undergone cell death (red lines). A population of untreated cells were monitored as a negative control group (blue lines).

C) Histogram quantifies intracellular reduced glutathione (GSH) was quantified in MDA-MB-231 parent or DTC and expressed as μg/cell. N>5, ***p<0.001.

D) Representative traces show total intracellular ROS (CM-DCFDA) in MDA-MB-231 parent or DTC quantified by FACS in the presence of: $H_2O_2$ (30 min), PI103, PI828 (5 μM and 10 μM, respectively, 3 h). Values expressed as % increase from vehicle control of the respective cell line. N>3, error bars indicate SEM.μ

E) Histogram shows ratio of GSH:total glutathione evaluated in parent or DTC incubated with PI103 (5 μM, 3 h). Values expressed as % change from vehicle-treated control group of respective cell line. N=9, ***p<0.001.

F) Histogram shows total intracellular GSH quantified in DTC. Prior to analysis cells were exposed to PKM2 activator (ML-265, 10 μM) or catalase (2000 U/ml) for 3 h. Values expressed as % change from vehicle-treated control groups. N=8, *p<0.05 by ANOVA.

G) Total intratumoral GSH obtained from residual tumor tissue homogenate of a syngeneic mammary carcinoma treated with vehicle or DTX (10 mg/kg i.v.). N=4 groups, ***p<0.001.

H) Systems biology schematic summarizes the above studies to illustrate the temporal coordination and ordering of molecular events initiated by chemotherapy exposure as it drives metabolic conversion in cells which acquire therapy tolerance.

I) Representative fluorescent microscopy of intracellular ROS (DCFDA), mitochondrial membrane potential (Δψm) in which increased fluorescence indicative of hyperpolarization (TMRM) and nitroreductase activity (Nit. Red.) in MDA-MB-231 parent and DTC.

J) Brightfield microscopy of DU-145 prostate cancer and a taxane resistant cell line (DU-145-TxR) following addition of docetaxel (DTX, 100 nM). Rounding of cells and membrane blebbing is indicative of cell death in parent DU-145.

K) Histogram shows FACS analysis of total cell ROS (CM-DCFDA) in DU-145 parent and paclitaxel resistant cell line (TxR) at baseline.

FIGS. 7A-L. Temporal ordering of drug schedules target metabolism-driven cross resistance A) Quantification of dead cells from parent or DTC treated with doxorubicin (72 h) evaluated by trypan blue exclusion. N=5, ***p<0.001.

B) Histogram from FACS shows doxorubicin internalization in MDA-MB-231 parent or DTC.

C) Cell viability analysis of MDA-MB-231 cells treated with doxorubicin in the presence or absence of exogenously added NADPH (25 μM), GSH (1 mM) or ectopic over expression (o.e.) of glucose-6-phosphate dehydrogenase (G6PD). N=6, ***p<0.001 by ANOVA.

D) Cell viability analyses of parent or DTC treated with combination of doxorubicin and PI103 (5 μM), doxorubicin and hexokinase inhibitor lonidamine (10 μM) or the G6PD inhibitors KB-458 and KB-697 (10 μM) (48 h). N=3.

E) Histogram shows doxorubicin internalization determined by relative fluorescence in MDA-MB-231 in the presence or absence of indicated pharmacologics (8 h). error bars indicate SEM, N>100 cells per group from fluorescent microscopy.

F) Representative western blot analysis of phosphorylated AKT-family proteins (PRAS40 and p70s6Kinase) in MDA-MB-231 DTC treated with inhibitors of AKT/mTOR and hexokinase.

G) Brightfield microscopy of culture dish-adhered cancer cells treated with 3×3 days regimen of DTX (100 nM), Dox (250 nM) and PI103 (2 μM) in the sequence and combinations indicated in figure panels. Quantification shows % of residual cells compared to parent±SEM performed in biological replicates.

Figure 7L:
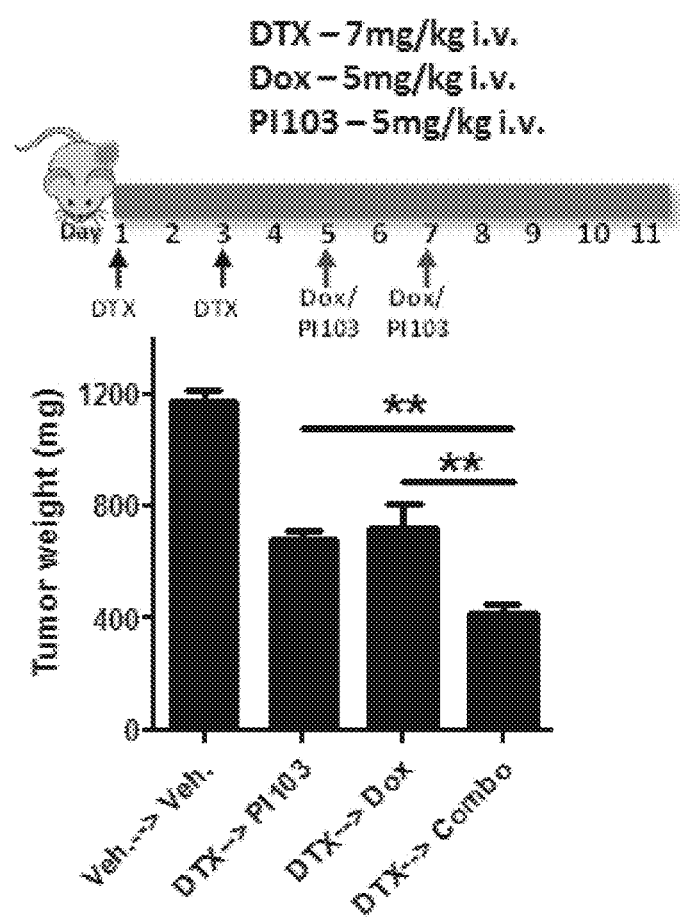

H) Tumor specific growth rate (11 days) derived from a syngeneic mammary carcinoma model (4T-1) treated with indicated temporally-sequenced regimens (supplemental FIG. 7L shows treatment schedule). N=4 per group, *p<0.05 p<0.01 *p<0.001.

I) Tumor volumes from syngeneic mammary carcinoma model (4T-1) treated with temporally-scheduled drug regimens. Note the flat line tumor growth in sequential combination group vs. single regimen cohorts. N=4 per group, **p<0.01 by 2-way ANOVA.

J) Representative western blot analysis of Glucose-6-phosphate in MDA-MB-231 transfected with an over expression plasmid or a vehicle control plasmid. Actin used as loading control K) Fluorescent microscopy of Doxorubicin in MDA-MB-231 DTC treated with PI103 (5 µM), PI828 (10 µM) or Lonidamine (100 µM).

L) Histogram shows tumor weight determined 11 days after initial dose of DTX following treatment regimen as shown in the schematic (above).

FIGS. 8A-H. Metabolically-Activated Drug-drug Conjugates (MADC) exploit adaptive cross-drug resistance and enhance tumor specificity A) Schematic representation of the di-sulfide hinge created between PI103 and doxorubicin creating a metabolically activated drug-drug conjugate (MADC). Cleaving this bond with a reduced glutathione relieves the prodrugs and subsequent intramolecular cyclyzation creates active compounds.

B) Tumor growth curves from syngeneic heterotopic mammary carcinoma model (4T-1). Mice were injected as indicated and tumor volumes were monitored every other day by digital calipers.

C) Mice were imaged following treatments as shown from FIG. 1B. Red circumscription shows heterotopic tumor growth of equivalent size between mice of each group. Note macroscopic toxicities (i.e. hairloss and fragility). Right panel shows quantification of mouse weights (grams).

D) Images of spleens from mice treated as shown in FIG. 1B. Scale bar=1 cm.

E) Histogram shows activated caspase-3 as determined by optical density from western blot analysis.

F) Tumor growth curves from mice treated as indicated. ***p<0.001 compared to DTX→Vehicle group.

G) Images of spleen taken from mice treated in panel A. Scale bar=1 cm.

H) Biodistribution of doxorubicin free drug or doxorubicin from the drug conjugate (MADC). Values were determined as described in the attached methods.

Figure 9A:
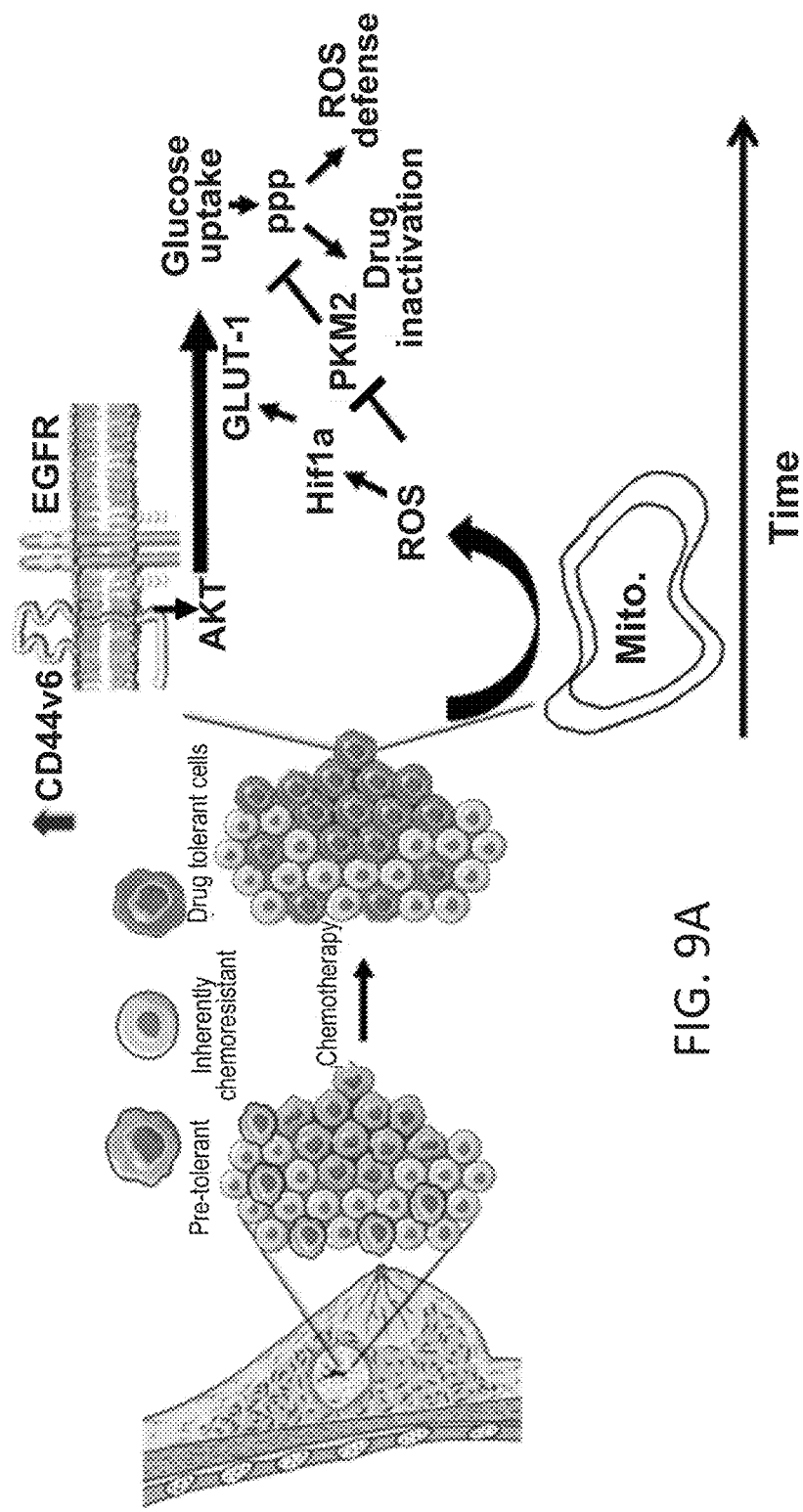
Figure 9B:
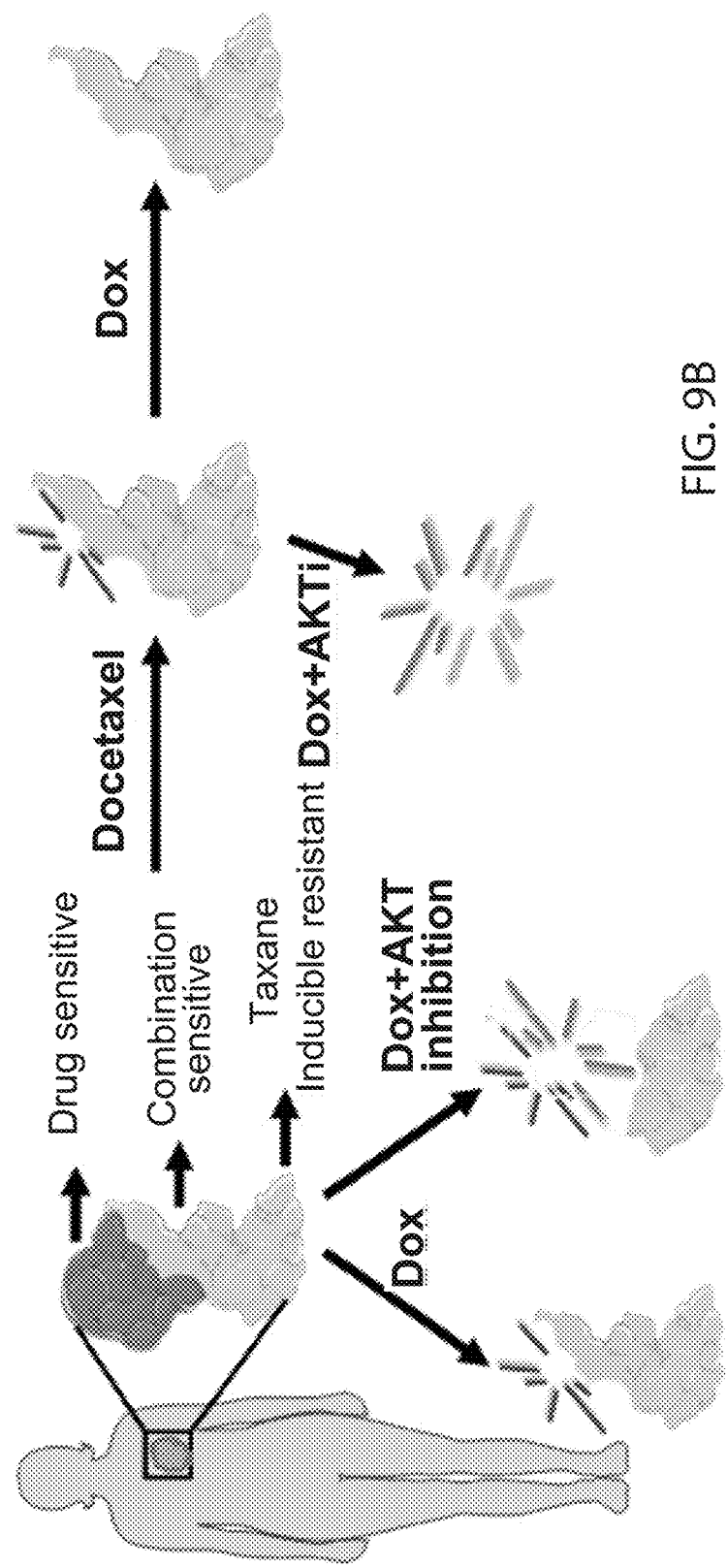

FIGS. 9A-B. Metabolic reprogramming schematics

A) Schematic shows molecular events which drive metabolic transposition in cancer cells which acquire tolerance to a primary cytotoxic chemotherapy. The model assumes inherently resistant as well as 'transitional capable' cells which acquire changes in their metabolic state through phenotypic plasticity. Resulting metabolic plasticity leads to both ROS defense as well as cross-resistance to other cytotoxic drugs.

B) Schematic shows clinical model in which the temporal-ordering of chemotherapy and AKT inhibitors (AKTi) is critical to 1. induce metabolic plasticity in order to 2. target it with rational combinations of metabolically-targeted and cytotoxic agents. The result of appropriate drug scheduling reveals greatest antitumor effects.

DETAILED DESCRIPTION

The conventional model for the development of resistance to chemotherapy is built on a 'somatic mutation theory' owing to the stochastic acquisition of mutations which confer resistance-favored properties[11]. However, this rarely disregarded yet antiquated model of drug resistance fails to incorporate phenotypic plasticity which governs and contributes to the subclonal heterogeneity of tumors[12]. For example, recent molecular characterizations now suggest that dynamic mechanisms may underlie transient induction of acquired, non-genetic chemotherapy resistance defined as a "drug tolerant state"[13]. In fact, adaptive resistance may emerge from a phenotypic transition, unhinging vulnerabilities within cancer cells to potentiate targeted therapy[14]. These emerging models of therapy failure which incorporate phenotypic heterogeneity suggest that a clear understanding for mechanisms and principles of cell plasticity are critical to design and affect treatments for cancer.

One feature of phenotypic heterogeneity which correlates directly to therapy resistance is the metabolic state of cancer cells[15]. Defined decades ago, the "Warburg effect" describes a favored metabolic state in tumors, distinct from normal tissue, in which energy is generated through glycolysis even in the presence of oxygen, while only minor populations thrive on oxidative phosphorylation[16,17]. Recent evidences show that phenotypic heterogeneity can be altered through induction of a metabolic switch involving a glucose uptake program and glycolytic phenotype creating a shunt to the pentose phosphate pathway (PPP)[18]. From a molecular perspective, a glycolytic phenotype in subclonal populations may potentially be maintained by oncogenic cortex kinases such as PI3K/AKT[19] which remains a vital source of glycolytic flux in cancer[20]. Despite these advances, there is an incomplete understanding for metabolism as it contributes to therapy outcome[21].

The present findings establish that intratumoral heterogeneity and cellular metabolism are linked, functionally dynamic under chemotherapy pressure and coordinate within temporal restrictions to elicit acquired cross-therapy resistance. Computational and systems biology were utilized to inspire a mechanistic view of drug tolerance. We identified that xenobiotic exposures (that is, cytotoxic chemotherapies) elicit an immediate intracellular production of cytokines to induce cortex scaffolds while mitochondrial functionality is concordantly exhausted. The inductions of these early events necessarily predisposed a cross-resistant population of cancer cells which enhance their glycolytic state in a redox-dependent fashion. This led to the conclusion that temporal coordination is a causal component of molecular, oncogenic behavior in therapy failure since the early-established network (CD44-driven AKT signaling) is dependent on delayed metabolic reprograms in drug tolerant cells. By harmonizing HIF1α transcriptional control, the cellular trafficking of GLUT-1 and bolstering of the PPP via a ROS-shunt, cells are able to rewire a metabolic state which permits cross-resistance to anthracycline or nucleoside analog chemotherapy. Thus overt restoration of chemosensitivity could be achieved by perturbing the metabolic transposition using targeted inhibitors upstream of the PPP. The identification of this therapeutic vulnerability enabled the successfully testing of drug schedules and combinations in rationally designed temporal sequence which exploit and overcome the mechanisms of cross-resistance. Excitingly, these findings point to a unique role that computational biology can provide for therapeutic interventions by obeying temporal event-ordering, providing clues to specific drug-scheduling. FIGS. 9A and 9B summarize by schematics the molecular events described in this study and clinically relevant strategies to target metabolic reprogramming, respectively.

Metabolically-Activated Drug Conjugates

Thus, described herein are metabolically-activated drug conjugates that comprise (i) an inhibitor of phosphatidylinositol 3-kinase/protein kinase-B/mammalian target of rapamycin (PI3K/AKT/mTOR) signaling or an inhibitor of glycolysis, linked via (ii) a disulfide bridge that is sensitive to the changed metabolism of the cell to (iii) a drug whose activity is suppressed by metabolic intermediates, e.g., an anthracycline or nucleoside analog. Outside the cell, when the conjugate is intact, the drugs are inactive or have low activity. Once inside a tumor or cancer cell, the presence of altered metabolism (e.g., increased levels of glutathione (GSH)) cleaves the linker and releases the active agents.

These conjugates can be made using methods known in the art using conventional techniques and readily available staring materials. In general, the conjugates can be obtained via standard organic chemistry synthesis methods. For example, the conjugates can be prepared using the methods described in Example 12. In some embodiments, both the PI3K/AKT/mTOR inhibitor and the anthracycline or nucleoside analog have a chemically reactive functional group, said function group selected from the group consisting of a primary or secondary amine, hydroxyl, thiol, carboxyl, aldehyde, and a ketone, which is used to chemically attach the linker using known synthetic methods.

PI3K/AKT/mTOR Inhibitors

The PI3K/AKT/mTOR signalling cascade plays crucial roles in a variety of physiologic processes including metabolic processes such as maintaining normal glucose homeostasis; see, e.g., Chia et al., Curr Oncol. 2015 February; 22(1):33-48; Saini et al., Cancer Treat Rev. 2013; 39:935-46. The first part of the conjugate comprises an inhibitor of the PI3K/AKT/mTOR pathway. A number of such inhibitors are known in the art, including PI3kinase inhibitors; mTOR inhibitors; and AKT inhibitors.

PI3kinase inhibitors include, but are not limited to pan-PI3K inhibitors pictilisib (GDC-0941); Buparlisib (BKM120), and pilaralisib (XL147); isoform-specific inhibitors Alpelisib (BYL719; p110α) and taselisib (GDC-0032; p110α).

PI3K/mTOR inhibitors include Voxtalisib (XL765), apitolisib (GDC-0980), gedatolisib (PF-05212384), PI103 (3-(4-(4-Morpholinyl)pyrido[3',2':4,5]furo[3,2-d]pyrimidin-2-yl)phenol), and GSK2126458 (2,4-Difluoro-N-{2-(methyloxy)-5-[4-(4-pyridazinyl)-6-quinolinyl]-3-pyridinyl}benzenesulfonamide).

AKT inhibitors include MK-2206 (8-[4-(1-aminocyclobutyl)phenyl]-9-phenyl-2H-[1,2,4]triazolo[3,4-f][1,6]naphthyridin-3-one; dihydrochloride), uprosertib (GSK2141795), ipatasertib (GDC-0068), and AZD5363.

Examples of mTOR inhibitors include: rapamycin; other rapamycin macrolides, or rapamycin analogues, derivatives or prodrugs; Everolimus (also known as RAD001, Everolimus/RAD001 is an alkylated rapamycin (40-O-(2-hydroxyethyl)-rapamycin), disclosed in U.S. Pat. No. 5,665,772; Novartis); Temsirolimus (also known as CCI-779, Temsirolimus/CCI-779 is an ester of rapamycin (42-ester with 3-hydroxy-2-hydroxymethyl-2-methylpropionic acid), disclosed in U.S. Pat. No. 5,362,718; Wyeth); umirolimus, zotarolimus, deforolimus (MK-8669; Merck, Ariad), wortmannin, TOP-216 (Toptarget A/S), TAFA93 (Isotechnika), CCI-779, ABT578, SAR543, ascomycin, FK506 (tacrolimus; Astellas), INK-128, EX2044, EX3855, EX7518, AZD-8055, AZD-2014, Palomid 529, Pp-242, OSI-027; AP23464, AP23573 or AP23841 (Ariad Pharmaceuticals); ABT-578 (40-epi-(tetrazolyl)-rapamycin; Abbott Laboratories); KU-0063794 or KU-0059475 (Kudus Pharmaceuticals); and TAFA-93 (a rapamycin prodrug; Isotechnika) Examples of rapamycin analogs and derivatives known in the art include those compounds described in U.S. Pat. Nos. 6,329,386; 6,200,985; 6,117,863; 6,015,815; 6,015,809; 6,004,973; 5,985,890; 5,955,457; 5,922,730; 5,912,253; 5,780,462; 5,665,772; 5,637,590; 5,567,709; 5,563,145; 5,559,122; 5,559,120; 5,559,119; 5,559,112; 5,550,133; 5,541,192; 5,541,191; 5,532,355; 5,530,121; 5,530,007; 5,525,610; 5,521,194; 5,519,031; 5,516,780; 5,508,399; 5,508,290; 5,508,286; 5,508,285; 5,504,291; 5,504,204; 5,491,231; 5,489,680; 5,489,595; 5,488,054; 5,486,524; 5,486,523; 5,486,522; 5,484,791; 5,484,790; 5,480,989; 5,480,988; 5,463,048; 5,446,048; 5,434,260; 5,411,967; 5,391,730; 5,389,639; 5,385,910; 5,385,909; 5,385,908; 5,378,836; 5,378,696; 5,373,014; 5,362,718; 5,358,944; 5,346,893; 5,344,833; 5,302,584; 5,262,424; 5,262,423; 5,260,300; 5,260,299; 5,233,036; 5,221,740; 5,221,670; 5,202,332; 5,194,447; 5,177,203; 5,169,851; 5,164,399; 5,162,333; 5,151,413; 5,138,051; 5,130,307; 5,120,842; 5,120,727; 5,120,726; 5,120,725; 5,118,678; 5,118,677; 5,100,883; 5,023,264; 5,023,263; and 5,023,262; 5,258,389; 5,100,883; 5,118,678; 5,151,413; 5,256,790; and 5,120,842; U.S. Patent Publication 2011/0178070; and PCT applications WO 94/09010; WO 92/05179; WO 93/11130; WO 94/02136; WO 94/02485; WO 94/02136; WO 95/16691; WO 99/15530; WO 96/41807; WO 96/41807; WO 98/02441; WO 01/14387; and WO 95/14023 all of which are incorporated herein by reference. Such analogs and derivatives of rapamycin also include 32-deoxorapamycin, 16-pent-2-ynyloxy-32-deoxorapamycin, 16-pent-2-ynyloxy-32 (S or R)-dihydro-rapamycin, 16-pent-2-ynyloxy-32 (S or R)-dihydro-40-O-(2-hydroxyethyl)-rapamycin, 40-O-(2-hydroxyethyl)-rapamycin, 32-deoxorapamycin and 16-pent-2-ynyloxy-32 (S)-dihydro-rapamycin. Rapamycin derivatives may also include the so-called rapalogs, e.g. as disclosed in WO 98/02441 and WO 01/14387 (e.g. AP23573, AP23464, AP23675 or AP23841). Further examples of a rapamycin derivative are those disclosed under the name biolimus-7 or biolimus-9 (BIOLIMUS A9™) (Biosensors International, Singapore). Any of the above rapamycin analogs or derivatives may be readily prepared by procedures as described in the above references. Additional examples of mTOR inhibitors useful in the invention described herein include those disclosed and claimed in U.S. patent application Ser. No. 11/599,663 and in US 20150005265 and US 20150051242. See, e.g., US 20150005265, US 20150051242, US20150071911. In some embodiments, the mTOR inhibitors are mTORC1 inhibitors including sirolimus; ridaforolimus; everolimus; and temsirolimus, or mTORC1/2 inhibitors including AZD2014, AZD8055, INK128 (MLN0128), and CC-223. See, e.g., Busaidy et al., J Clin Oncol. 2012 Aug. 10; 30(23):2919-28; Chia et al., Curr Oncol. 2015 February; 22(1): 33-48; and Polivka and Janku, Pharmacol Ther. 2014 May; 142(2):164-75.

Inhibitors of Glycolysis

In addition to or as an alternative to an PI3K/AKT/mTOR inhibitor, an inhibitor of glycolysis can be used in the methods and compositions described herein. Inhibitors of glycolysis include inhibitors of Glucose-6-phosphate dehydrogenase (G6PD), hexokinase (e.g., HKII), PFKFB3, and glucose transporters (e.g. GLUT1, GLUT 3), e.g., 3-(3-pyridinyl)-1-(4-pyridinyl)-2-propen-1-one (3PO), Phloretin, WZB117, Fasentin, 2-Deoxyglucose, lonidamine, 3-Boromopyruvate, Imatinib, 6-aminonicotinamide, 5-(4-hydroxy-3-trifluoromethylbenzylidene)-3-[4,4,4-trifluoro-2-methyl-2-(2,2,2-trifluoroethyl)butyl]thiazolidine-2,4-dione; and Oxythiamine. See, e.g., Pelicano et al., Oncogene (2006) 25, 4633-4646; Xu et al., Cancer Res. 2005 Jan. 15; 65(2):613-21; Ganapathy-Kanniappan and Geschwind, Molecular Cancer 2013, 12:152; Scatena et al., Expert Opinion on Investigational Drugs, October 2008, 17(10): 1533-1545; Clem et al., Mol Cancer Ther 2008, 7(1):110-120; Wang et al., J Med Chem. 2012 Apr. 26; 55(8):3827-36.

Linkers

The conjugates described herein include a linkers comprising a disulfide bridge. The linkers can comprise functional or reactive moieties capable of covalently binding to an inhibitor of phosphatidylinositol 3-kinase/protein kinase- B/mammalian target of rapamycin (PI3K/AKT/mTOR) signaling and an anthracycline or nucleoside analog. Exemplary functional groups include hydroxyl, amine, thiol, carboxyl, aldehyde, glyoxal, dione, alkenyl, alkynyl, alkedienyl, azide, acrylamide, vinyl sulfone, hydrazide, aminoxy, maleimide, dithiopyridine, and iodoacetamide moieties. The linkers can further include a $C_{1-20}$ alkyl on either side of the disulfide bridge. The alkyl chain can be linear or branched, saturated or unsaturated, unsubstituted or substituted. For example, the linkers can have a general formula:

$X_1$-$L_1$-S—S-$L_2$-$X_2$ wherein:
$X_1$ and $X_2$ are each independently a functional or reactive moiety as described above (e.g., hydroxyl, amine, thiol, carboxyl, aldehyde, glyoxal, dione, alkenyl, alkynyl, alkedienyl, azide, acrylamide, vinyl sulfone, hydrazide, aminoxy, maleimide, dithiopyridine, and iodoacetamide moieties);
$L_1$ and $L_2$ are each independently a $C_{1-20}$ alkyl; and
S—S is a disulfide bridge.

A variety of other disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene)-, SPDB and SMPT (See, e.g., Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987. See also U.S. Pat. No. 4,880,935). See, e.g., US 20060024317; US 20100092496; US 20150079114; and WO 2009143412, all of which are incorporated herein in their entirety.

Although disulfide linkers are preferred in some embodiments, other linkers can be used, e.g., a pH-sensitive linker that is sensitive to hydrolysis at certain pH values. For example, an acid-labile linker that is hydrolyzable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661) could be used. Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929). In some embodiments, the linker is a malonate linker (Johnson et al., 1995, Anticancer Res. 15:1387-93), a maleimidobenzoyl linker (Lau et al., 1995, Bioorg-Med-Chem. 3(10): 1299-1304), a maleimidocaproyl ("mc") linker (Doronina et al., 2006, Bioconjug Chem. 17:114-24), or a 3'-N-amide analog (Lau et al., 1995, Bioorg-Med-Chem. 3(10):1305-12). Peptide and hydrazine linkers can also be used. See, e.g., US 20060024317; US 20100092496; US 20150079114; and WO 2009143412.

Anthracyclines

A number of antrhacylcines are known in the art. In some embodiments, the anthracycline is selected from the group consisting of daunorubicin, doxorubicin, epirubicin, idarubicin, pirarubicin, aclarubicin, caminomycin, valrubicin and mitoxantrone. In some embodiments, the anthracycline is doxorubicin. In some embodiments, the anthracycline is a compound of the formula I or II:

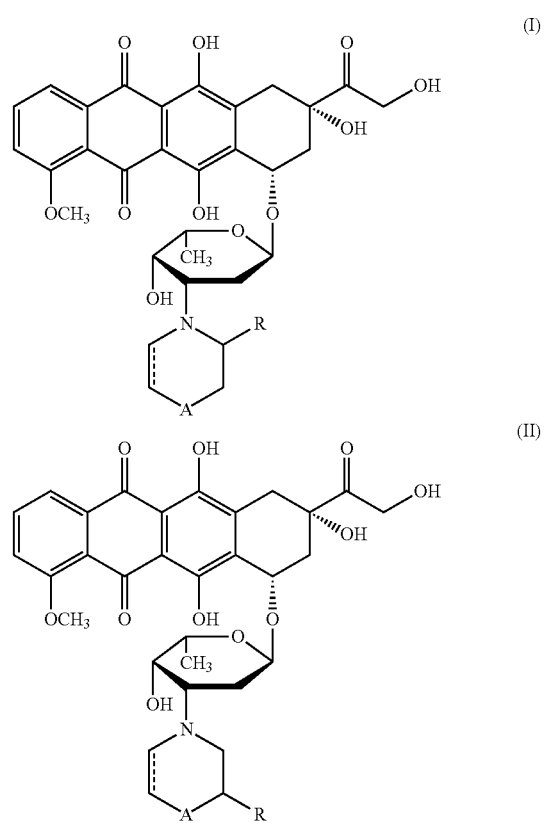

wherein A is nothing or it may be selected from the group consisting of NH, N-alkyl,
N-cycloalkyl, O, S, and $CH_2$; the dotted line denotes a single or a double bond; and R is H or CN; and a linker binding the targeting moiety via a sulfide group and the anthracycline chemotherapeutic drug via an intracellularly cleavable moiety. When A is "nothing," the carbon atoms adjacent to A, on each side, are connected by a single bond, thus giving a five-membered ring.

As used herein, "alkyl" refers to a saturated aliphatic hydrocarbon radical including straight chain and branched chain groups of 1 to 20 carbon atoms (whenever a numerical range; e.g. "1-20", is stated herein, it means that the group, in this case the alkyl group, may contain 1 carbon atom, 2 carbon atoms, 3 carbon atoms, etc. up to and including 20 carbon atoms). Alkyl groups containing from 1 to 4 carbon atoms are referred to as lower alkyl groups. More preferably, an alkyl group is a medium size alkyl having 1 to 10 carbon atoms e.g., methyl, ethyl, propyl, 2-propyl, n-butyl, iso-butyl, tert-butyl, pentyl, and the like. Most preferably, it is a lower alkyl having 1 to 4 carbon atoms e.g., methyl, ethyl, propyl, 2-propyl, n-butyl, iso-butyl, or tert-butyl, and the like.

As used herein "cycloalkyl" refers to a 3 to 8 member all-carbon monocyclic ring, an all-carbon 5-member/6-member or 6-member/6-member fused bicyclic ring or a multicyclic fused ring (a "fused" ring system means that each ring in the system shares an adjacent pair of carbon atoms with each other ring in the system) group wherein one or more of the rings may contain one or more double bonds but none of the rings has a completely conjugated pi-electron system. Examples, without limitation, of cycloalkyl groups are cyclopropane, cyclobutane, cyclopentane, cyclopentene, cyclohexane, cyclohexadiene, adamantane, cycloheptane, cycloheptatriene, and the like. A cycloalkyl group may be substituted or unsubstituted.

See, e.g., US 20140154273, US 20140148587, which are incorporated by reference herein.

Nucleoside Analogs

Nucleoside analogs (such as gemcitabine) have active sites that are susceptible to reductive metabolism. In addition, nucleoside analogs are metabolized by deaminases which may be downstream by-products of nucleoside biosynthesis from pentose phosphate pathway activity. A number of nucleoside analogs are known in the art. In some embodiments, the nucleoside analogs is selected from the group consisting of deoxyadenosine analogues, e.g., clofarabine, vidarabine; deoxycytidine analogues, e.g., cytarabine, gemcitabine and LY2334737 (an orally administered derivative of gemcitabine); guanosine and deoxyguanosine analogues, e.g., Nelarabine (a prodrug of the guanosine analog, 9-β-D-arabinofuranosyl guanine (ara-G)); 5-fluorouracil (5FU); nucleobases; cladribine; fludarabine; sapacitabine, mericitabine; NUC-1031; GS-7340; pronucleotides e.g., sofosbuvir and stampidine); CP-4055, SGI-110 and FV-100 are conjugates. See, e.g., Jordheim et al., Nature Reviews Drug Discovery 12:447-464 (2013); Lee et al., Radiation Oncology 8:223 (2013).

Pharmaceutical Compositions and Methods of Administration

The methods described herein include the use of pharmaceutical compositions comprising the MADC described herein as an active ingredient.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral, e.g., intravenous, intradermal, intratumoral, intrathecal, subcutaneous, oral (e.g., inhalation), transdermal (topical), transmucosal, and rectal administration.

Methods of formulating suitable pharmaceutical compositions are known in the art, see, e.g., *Remington: The Science and Practice of Pharmacy*, 21st ed., 2005; and the books in the series *Drugs and the Pharmaceutical Sciences: a Series of Textbooks and Monographs* (Dekker, N.Y.). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The pharmaceutical compositions can also be prepared in the form of suppositories (e.g., with conventional suppository bases such as cocoa butter and other glycerides) or retention enemas for rectal delivery.

In one embodiment, the therapeutic compositions are prepared with (comprise) carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

Methods of Treatment

The methods described herein can be used to treat subjects with cancer, e.g., subjects who have cancer that demonstrates or develops drug resistance.

As used in this context, to "treat" means to ameliorate at least one clinical parameter of the cancer. In some embodiments, the parameter is tumor size, tumor growth rate, recurrence, or metastasis, and an improvement would be a reduction in tumor size or no change in a normally fast growing tumor; a reduction or cessation of tumor growth; a reduction in, delayed, or no recurrence, or a reduction in, delayed, or no metastasis. Administration of a therapeutically effective amount of a compound described herein for the treatment of a cancer would result in one or more of a reduction in tumor size or no change in a normally fast growing tumor; a reduction or cessation of tumor growth; or a reduction in, delayed, or no metastasis. In some embodiments, e.g., a treatment designed to prevent recurrence of cancer, the treatment would be given occur after a localized tumor has been removed, e.g., surgically, or treated with radiation therapy or with targeted therapy with or without chemotherapy. Without wishing to be bound by theory, such a treatment may work by keeping micrometastases dormant, e.g., by preventing them from being released from dormancy.

As used herein, the term "hyperproliferative" refer to cells having the capacity for autonomous growth, i.e., an abnormal state or condition characterized by rapidly proliferating cell growth. Hyperproliferative disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. A "tumor" is an abnormal growth of hyperproliferative cells. "Cancer" refers to pathologic disease states, e.g., characterized by malignant tumor growth. The methods described herein can be used to treat cancer, e.g., solid tumors of epithelial origin, e.g., as defined by the ICD-O (International Classification of Diseases—Oncology) code (revision 3), section (8010-8790), e.g., early stage cancer, is associated with the presence of a massive levels of satellite due to increase in transcription and processing of satellite repeats in epithelial cancer cells. Thus the methods can include the interference of satellite repeats in a sample comprising cells known or suspected of being tumor cells, e.g., cells from solid tumors of epithelial origin, e.g., pancreatic, lung, breast, prostate, renal, ovarian or colon/colorectal cancer cells.

Cancers of epithelial origin can include pancreatic cancer (e.g., pancreatic adenocarcinoma), lung cancer (e.g., non-small cell lung carcinoma or small cell lung carcinoma), prostate cancer, breast cancer, renal cancer, ovarian cancer, or colon cancer. The methods can also be used to treat early preneoplastic cancers as a means to prevent the development of invasive cancer.

The methods include administering a first treatment that induces a metabolic change in the cells, i.e., an increase in glucose uptake; this first treatment is also referred to herein as the "induction treatment". This metabolic change is typically manifested by the presence of drug tolerance. The induction of drug tolerance is often concordant with a plateau of tumor growth; a clinician can monitor tumor growth by volume and size, and the development of a plateau in growth is a good indicator for development of resistance. Following chemotherapy, a halt in growth of the tumor without substantial regression can also indicate a drug tolerant phenotype.

Additionally, serum levels of tumor-related proteins (e.g., PSA for prostate cancer) can indicate tumor behavior and a loss of proliferative signals can indicate a plateau of growth and therefore acquisition of resistant phenotype. FDG-PET scan to indicate glucose uptake which should be performed days after chemotherapy.

The acquisition of resistance observed appears as a phenotypic phenomenon in the absence of mutation; i.e., it is induced by the administered cytotoxic, transiently.

The presence of drug resistance can be determined after the last dose of the round of induction therapy, e.g., 1-5 or 1-7 or 1-10 or 1-21 days after the last dose of a cytotoxic treatment, to assess the effect of the therapy. Standard imaging methods can be used to determine tumor size. In addition, a clinician could use PET scans or serum levels of tumor-derived proteins to determine the effect of treatment or change in tumor behavior pattern. Again the presence of a plateau in growth indicates the presence of resistance and successful induction of the metabolic change described herein.

In some embodiments, the first or induction treatment is administration of one or more rounds of a cytotoxic agent, e.g., a taxane, alkylating agent, anthracycline, *vinca* alkaloid, nucleoside analogue or nucleobase, or radiation therapy, or a combination thereof.

Cytotoxic agents include alkylating agents such as bendamustine, busulfan, carmustine, chlorambucil, cyclophosphamide, dacarbazine, ifosfamide, melphalan, procarbazine, streptozocin, and temozolomide; anti-metabolites such as asparaginase, capecitabine, cytarabine, 5-fluoro uracil, fludarabine, gemcitabine, methotrexate, pemetrexed, and raltitrexed; anti-tumour antibiotics such as actinomycin d/dactinomycin, bleomycin, daunorubicin, doxorubicin, doxorubicin (pegylated liposomal), epirubicin, idarubicin, mitomycin, and mitoxantrone; plant alkaloids/microtubule inhibitors such as etoposide, docetaxel, irinotecan, paclitaxel, topotecan, vinblastine, vincristine, and vinorelbine; and DNA linking agents such as carboplatin, cisplatin, and oxaliplatin.

Taxanes include any known taxane compound, or known taxane derivatives, or salts thereof. Two classic taxane compounds are paclitaxel and docetaxel. See, e.g., U.S. Pat. Nos. 5,912,263, 6,136,808, 6,939,978, 5,693,666, 6,538, 020, 6,509,370, 7,060,724, 6,569,459, 6,680,877, 6,541,508, 6,649,777, 5,998,656, 6,028,005, 5,994,576, 6,147,234, and US 20150080578.

Alkylating agents also include mustard derivatives, nitrosourea derivatives, platinum compounds, and imidazole carboxamide compounds. Examples of alkylating agents are bendamustine, lomustine, carmustine, streptozocin, mechlorethamine, melphalan, uracil nitrogen mustard, chlorambucil, cyclosphamide, iphosphamide, cisplatin, carboplatin, oxaliplatin, mitomycin, thiotepa, dacarbazin, procarbazine, hexamethyl melamine, triethylene melamine, busulfan, pipobroman, mitotane and other platine derivatives.

Anthracyclines are described above.

*Vinca* alkaloids are antimitotic chemotherapeutic drugs that were originally isolated from the periwinkle plant (*Vinca rosea*) and includes without limitation, vinblastine, vincristine, vindesine and vinorelbine and derivatives thereof, see, e.g., US 20120202840 and US 20150073008.

Pharmaceutically acceptable salts of the agents described herein can also be used.

Radiation therapy generally uses high doses of radiation, such as X-rays, to destroy cancer cells. Radiation is typically delivered in one of two ways: external-beam radiation therapy and branchytherapy. External radiation therapy includes conformal radiotherapy (3D-CRT), intensity-modulation radiation therapy (IMRT) and proton therapy. Brachytherapy, or internal radiation therapy, uses implanted radioactive materials. Radiation therapy can also include combinations of external radiation therapy and brachytherapy.

In some embodiments, the induction therapy is chemoradiotherapy (CRT), in which a combination of radiation therapy and chemotherapy, e.g., with a cytotoxic agent, e.g., taxane, alkylating agent, anthracycline, or *vinca* alkaloid, is administered.

In some embodiments, the methods can include administering a round of a combination of a PI3K/AKT/mTOR (PAM) inhibitor (or glycolysis inhibitor) as described herein with an anthracycline or nucleoside analog; this combination can be used as an alternative to (or in addition to) the MADC described herein, in a subject who has been treated with one or more rounds of an induction therapy and has developed resistance. This combination is referred to herein as combination or PAMA therapy. In preferred embodiments the agents in the combination are administered at least on the same day or within 12 hours, 6 hours, 4 hours, or 2 hours of each other, or preferably substantially simultaneously, e.g., 1 hour of each other. In some embodiments, the metabolic inhibitor (PI3K/AKT/mTOR (PAM) inhibitor or glycolysis inhibitor) is administered before (e.g., immediately before) the anthracycline or nucleoside analog.

In some embodiments, the combination therapy or MADC is used in combination with another treatment, e.g., after a round (administration of one or more doses) of a first or induction treatment. In some embodiments, the methods described herein include the administration of a combination therapy or MADC are used in subjects who have been treated with a first or induction treatment.

In some embodiments, the PAMA combination therapy or MADC is administered within 1-21 or 1-14 days of the last dose of a round of induction therapy, or within about 21 days, 14 days, 10 days, 7 days, 5 days, 3 days, 2 days, or 1 day of the last dose of induction therapy. In some embodiments, the PAMA combination therapy or MADS is administered at least about 1, 2, 3, 4, 5, 6, 12, 18, or 24 hours, or 2, 3, 5, 7, 10, or 14 days after the last dose of induction therapy. Ranges including each of these time points are also described, e.g., within about 24-240 hours, 12-240 hours, 1-3 days, 1-5 days, or 12 hours to 3 days of the last dose of induction therapy, and so on. In this context, "about" refers to a variability of up to 60 minutes.

In some embodiments of the methods described herein a cycle of treatment comprises a round of an induction treatment, followed by a round of the combination therapy or MADC described herein; optionally, the cycle is repeated one or more times. In these embodiments, the methods can include administering a first round of an induction therapy (while it is referred to as a "first" round, the subject may have been treated with that therapy previously), followed (e.g., within 24-240 hours of the last dose of the first round) by a first round of the combination therapy or MADC described herein (again, while it is referred to as a "first" round, the subject may have been treated with that therapy— or components thereof—previously), optionally followed (e.g., within 24-240 hours of the last dose of the first round of the combination therapy or MADC) by a second round of the induction therapy, optionally followed by a second round of the combination therapy or MADC; optionally with 1-21 days in between each round.

EXAMPLES

The invention is further described in the following examples, which do not limit the scope of the invention described in the claims.

Methods

The following materials and methods were used in Examples below.

Chemicals and Reagents

Unless noted otherwise, all reagents, small molecule inhibitors and chemotherapies were of the highest grade purchased from Sigma-Aldrich (St. Louis, Mo.). Vincristine and Lonidamine were purchased from Tocris biosciences (Minneapolis, Minn.). Everolimus and PI103 were purchased from SelleckChem (Houston, Tex.). Doxorubicin, PI828 and Erlotinib were purchased from LC Labs (Woburn, Mass.). KB-697 (ID#6138697) and KB-458 (ID#6049458) were purchased from ChemBridge (San Diego, Calif.). All chemotherapeutics and small molecule inhibitors were dissolved in DMSO to a stock concentration of 10 mM and kept frozen with the exception of compounds used for animal studies which were prepared at the indicated concentrations fresh. Recombinant IL-23, IFN-g, GM-CSF, IL-6 and IL-8 were purchased from Biolegend (San Diego, Calif.).

Cell Culture and Gene Knockdown with siRNA

MDA-MB-231 (ATCC), MDA-MB-468 and 4T-1 mammary carcinoma cells (ATCC) were cultured in DMEM containing 10% Fetal Bovine Serum (FBS) at 37 C and 5% $CO_2$. DU145 and DU145-TxR were provided by A. Mizokami[63] and cultured in DMEM containing 10% FBS, resistant line included 100 nM paclitaxel in the culture media. During treatments with chemotherapeutics, cells were grown to semi-confluence and treated with indicated concentrations of chemotherapy in serum-containing medium for indicated time points. When small molecule inhibitors were included in treatments, they were added simultaneously with chemotherapy. For siRNA gene knockdown, cells were transfected with silencer-select siRNA plasmids (Ambion, Invitrogen, Grand Island, N.Y.) pan-CD44(1) (s2682) panCD44(2) (s2681), siHIF1A (s6539) using lipofectamine 2000 (Invitrogen, Carlsbad Calif.) following manufacturer protocol and cultured for 72 hours prior to treatment. Scrambled siRNA was used as a control. For chemotherapy treatment experiments: Cancer cells were plated at a density of $0.5$-$1 \times 10^5$ cells/ml and allowed to adhere for 24-48 hr. When cells reached ~70% confluency they were treated with cytotoxics at indicated concentrations for 24-48 hours and utilized for subsequent assays. For experiments in which a shorter incubation was used (i.e. 15 min-4 hours) fresh media was added 24 hours prior to addition of chemotherapy suspended to stock concentration in PBS. For generation of DTC: Cells were treated for 48 hours with chemotherapy. Following washes with PBS, adherent cells were trypsinized and re-plated at a density of $1.5$-$2 \times 10^5$ cells/ml and cultured in serum-containing medium. After 24 hours incubation, floating cells were removed and remaining cells were washed with 1× PBS and considered as chemotherapy-tolerant cells. A population of drug naïve parent cells were always cultured alongside DTC and fresh media was added at every interval that experimental population (DTC) received fresh media.

In-Vitro Metabolic and Reductive Stress Experiments

In vitro detection of glucose uptake was performed using 2-(N-7-Nitrobenz-2-oxa-1,3-diazol-4-yl)Amino)-2-Deoxyglucose (2-NBDG) (Invitrogen, Carlsbad Calif.), dissolved in DMSO to 50 mM. Cells were pre-treated with kinase inhibitors or vehicle for 3 hours in glucose- and phenol red-free media before addition of 50 µM 2-NBDG and subsequently read by FACS ex/em 488/535 nm. ROS was determined by pre-loading cells with CM-DCFDA (1 µM), washed 2 times with PBS and subsequently treated with $H_2O_2$ or vehicle; when kinase inhibitors were included in treatment, cells were first incubated with inhibitor for 3 hours prior to CM-DCFDA loading. Fluorescence was then determined by FACS ex/em 488/535 nm. For the following assays, cells were trypsinized and counted by Nexcelom cell counter (Lawrence, Mass.) prior to being subjected to analysis in order to achieve a quantitative value per cell: Reduced glutathione was determined using a colorimetric glutathione recycling system by DTNB following manufacturer protocol (Biovision, Milpitas Calif.). ATP analysis was performed using the ATP colorimetric analysis kit (Biovision) according to manufacturer protocol. Reductive stress was detected using the Enzo nitroreductase hypoxia kit (Enzo Life Sciences, Ann Arbor Mich.) following manufacturer protocol and visualized by fluorescent microscopy; a set of non-docetaxel-treated control cells loaded with fluorescent probe were compared against docetaxel-treated cells to derive a % redox stress increase which was calculated as fluorescence intensity of nitroreductase probe per cell and expressed as increase from vehicle. Protein synthesis was measured by two means 1. L-azidohomoalanine amino acid analog of methionine containing an azide moiety was added to cultured cells (parent or DTC) for 3 hours which is incorporated into proteins during active protein synthesis. Fluorescent detection of the incorporated amino acid is performed by chemoselective ligation (click reaction) between the azido-modified protein and an Alexa Fluor® 488 alkyne (Click-iT® AHA, Life technologies, Carlsbad Calif.). Fluorescence was detected by FACS as described below. 2. CMV promoter-driven Green fluorescent protein (CMV-GFP) was virally transfected into cells (GenTarget San Diego, Calif.). GFP protein translation was determined by fluorescent microscopy. For studies in which cell death was evaluated with GFP expression, cells were treated for 48 hours with 25 nM docetaxel, fixed in 4% formaldehyde, permeabilized with 0.05% saponin and blocked with 10% goat serum before incubation with antibody detecting cleaved caspase-3 (Fluor594) for 24 hours at 4 C. Individual cells were evaluated for fluorescent intensity of caspase-3 activity (red signal intensity) and green fluorescent protein intensity. Quantitative values were then averaged to provide a mean fluorescence of each signal. Final values were plotted as individual cell intensity deviation from the mean for both GFP and Cleaved caspase-3 to provide GFP signal as a function of cell death.

In Vivo Experiments 1 million 4T-1 mouse mammary carcinoma cells suspended in 100 µL PBS were injected per left flank of 5-6 week old Balb/C (heterotopic) or mammary fat pad (orthotopic). Docetaxel (DTX) was dissolved in pure Ethanol at a concentration of 50 mg/ml mixed 1:1 with Polysorbate 80 (Tween 80) and brought to a final working concentration with PBS. Tumor volumes were assessed by the following formula: (Width×Width×length)/2 and values were utilized to calculate tumor specific growth rate (SGR) by the algorhythm (ln $[V_2/V_1]/[t_2-t_1)]$ where V=volume and t=time in days[64]. For in vivo analysis of 2-NBDG uptake, mice were treated as indicated (i.e. Docetaxel intratumoral or intravenously) and monitored until tumors reached ~300 mm³. Subsequently, mice were administered a 10 mg/kg i.v. injection of 2-NBDG 2 hours prior to sacrificing and harvesting tumors for confocal microscopic analysis by frozen section (described below). TUNEL staining was performed to visualize regions of apoptosis using the TUNEL assay kit and performed on frozen section slides as directed by manufacturer (Roche). Glucose quantitation (mg/dL) was measured using the onetouch lifescan glucose monitor (Life Scan, Inc. Militipas, Calif.) by calculating mg of glucose per volume of tissue homogenate (in PBS) and normalized as a ratio of mg/dL of glucose to mg of tissue homogenized. Typically, >250 mg of tissue was homogenized in 50 µL of PBS to achieve a readable output.

Human Explant Studies

Anonymous human breast cancer tissues (N=7) from patients refractory to taxane-containing regimens and varying stages of disease were obtained from Mitra Biotech collected under IRB approval from HCG Bangalore Institute of Oncology with due consent. Fresh tumor tissues were collected from breast cancer patients immediately after surgical resection at HCG cancer hospital, Bangalore, India. The tumor samples were transported to the laboratory at 4° C., in appropriate transport buffer within 60 minutes post-resection, for ex-vivo studies and molecular and pathological evaluation. Tissues were cut into thin sections and cultured in 96 well plate using optimized conditions [BISWANATH REF]. Tumors were treated with a taxane, or doxorubicin at Cmax for 72 h. DMSO was used as a vehicle control. After treatment, tumor cell viability was measured. Immunohistochemistry (IHC) was performed as described in methods. Glucose uptake was evaluated 72 h post culture.

Immunohistochemical Analysis:

Changes in GLUT1 and CD44v6 and Caspase3 (cleaved) prior to and after drug treatment were evaluated by IHC using specific antibodies. Initial antigen retrieval of FFPE sections was done in Antigen Unmasking Solution (Citrate based, Vector Laboratories) by exposure to microwave heating for 30 min. Quenching of endogenous peroxidase was done by 3% $H_2O_2$ for 15 min. Protein blocking was carried out at room temperature (RT) for 1 h with 10% goat serum. FFPE sections were incubated with primary antibodies at RT for 1 h. Rabbit polyclonal GLUT1 antibody (Abcam) was used at a 1:200 dilution, mouse monoclonal anti CD44v6 antibody (clone VFF-18, Abcam) was used at a dilution of 1:500. Induction of apoptosis was detected by staining for cleaved caspase-3 using polyclonal anti-cleaved caspase-3 (Asp175) antibody (rabbit polyclonal, Cell Signaling Technology) at 1:600 dilution for 1 hour at RT—all followed by incubation with HRP-conjugated secondary antibody (SignalStain® Boost IHC Detection Reagent; Cell Signaling Technology) for 1 h at RT. Chromogenic development of signal was done using 3,3'-diaminobenzidine (DAB Peroxidase Substrate Kit; Vector Laboratories). Tissues were counterstained with Hematoxylin (Papanicolaous solution 1a). Scoring and calculation of drug induced inhibition of individual tumor explants were performed as described previously[22].

Viability Assay:

Tumor cell viability was assessed by Cell Counting Kit-8 (CCK-8) (Dojindo). CCK-8 solution was added to each well of the plate and incubated at 37° C. for 3 h in a 5% CO2 incubator under humidified condition. The absorbance was measured at 450 nm using a multimode microplate reader (Enspire, Perkin Elmer). Baseline samples (T0) were used to normalize inter-sample variation. The results were expressed as a percentage of viability or inhibition relative to untreated controls.

Glucose Uptake Assay:

Glucose uptake assay was carried 72 hours post culture. Two micro liter of culture supernatant was added to 200 µl of Glucose reagent (Liquixx Glucose Reagent, Erbaa). All readings along with glucose standard (100 mg/dL) were run in triplicate. The plate was incubated at room temperature for 5 minutes on a plate shaker at medium speed and the absorbance was measured at 505 nm using multimode plate reader (Perkin Elmer).

In-Vitro Cytotoxicity and Cell Viability Assays

Following drug incubation, cells were washed and suspended in phenol red-free RPMI or DMEM and subsequently treated with MTS reagent using manufacturer protocol (Promega, Madison, Wis.). Trypan blue exclusion was used to validate experiments and evaluate % of dead cells performed by bright field microscopy.

FACS Analyses

Cells were cultured as indicated, removed from culture dishes with accutase stem-pro dissociation reagent (Invitrogen, Carlsbad Calif.) and fixed with 4% paraformaldehyde in PBS for 30 min at RT, washed twice with PBS and blocked in 10% goat serum (v/v). Whenever necessary, cells were permeabilized with 0.05% saponin in PBS. Cells were incubated with CD44-APC (BD biosciences, San Jose, Calif.) overnight at 4 C and analyzed by FACS (C6 Accuri cyomteters Inc Ann Arbor, Mich.), data analysis using FlowJo software (Tree Star Inc., Ashland Oreg.) and Accuri cFlow plus software to obtain and confirm mean fluorescent intensity (GNU.org).

High-Density Immunoarrays

The Proteome Profiler™ or cytokine array panels (R&D systems, Minneapolis Minn.) were used to identify phosphorylated residues correlating to AKT-associated proteins or total chemokines/cytokines within cell populations, respectively. Following the Bradford protein analysis assay to normalize total protein content, cell lysate was applied to the membranes following manufacturer protocol. Western blot of total protein (i.e. AKT and mTOR) were performed to confirm equal loading of lysate. EGFR phosphorylation high-density immunoarray was performed following manufacturer protocol to detect changes between phospho and total EGFR in parent or DTC (Raybiotech, Norcross Ga.). Membranes were visualized by chemiluminescence (Syngene, Cambridge UK). Optical densities were determined by Image J software (NIH.gov) and Adobe CS5. Reference spots were used to normalize between array membranes.

Quantification of Growth Factors

EGF ELISA was performed from lysate following manufacturer protocol (Peprotech, Rockyhill N.J.) after cells were treated as indicated, trypsinized and counted to normalize similar number of cells between treatments and replicates.

Confocal Microscopy and Immunofluorescence

Parent cells or DTC were generated as described above and plated in 4 chamber glass slides (BD Biosciences, San Jose Calif.) or into plastic-bottom cell culture dishes at a concentration of 10,000 cells/ml. Following treatments, cells were washed in PBS and fixed in 4% Paraformaldehyde for 30 minutes. Permeabilization, when necessary, was achieved with 10% (v/v) Goat serum (Vector Laboratories, Burlingame Calif.) and 0.05% Saponin (w/v) in PBS for 90 minutes. Blocking was performed in 10% (v/v) Goat serum in PBS. The cells were labeled with the indicated primary antibodies CD44 (Clone IM7 from eBioScience) conjugated to Fluor594 (AnaSpec, Freemont Calif.) at 1:100 for 24 h at 4 C and masked with DAPI-containing hard-set mounting medium (Vector Laboratories, Burlingame Calif.). Bright field and fluorescent images were obtained using three channels on a NIKON Eclipse TI-U microscope with a 20× ELDW, 10× or 40× Plan-Apo objective lens (Nikon, Melville N.Y.). NIS Elements Viewer version 3.22 (Nikon, Melville N.Y.) software was used to capture the images to file. Confocal microscopy of IHC from frozen sections of tumor tissue was performed with an inverted Nikon Confocal microscope (TE2000) with Auto DeBlur deconvolution software and fitted with 3 laser detection (Nikon, Melville N.Y.). Gains were set manually based on negative control stains (secondary antibody only) and were left unaltered between treatment groups of similar experiments. TUNEL staining was performed to visualize regions of apoptosis using the TUNEL assay kit and performed as indicated by provider (Roche, Basel Switzerland). When representative images are shown in figures, these are derived from experiments performed in at least biological triplicate on independent occasions. In general, images were obtained from more than 100 cells per conditions and chosen to represent the overall alterations in each experimental group. When unequal gains were set during confocal microscopy to compare localization of proteins, those instances have been indicated in the figure legends.

Immunoprecipitation, Subcellular Fractionation and Immunoblotting

Laemli sample buffer was prepared as a 5× solution containing □-mercaptoethanol as a reducing agent. Immunoprecipitaion was performed using both classic and direct IP kits purchased from Pierce following manufacturer protocols (Thermo Fisher inc. Rockford, Ill.). Briefly, cell lysates were prepared using IP/Lysis Buffer (Thermo Fisher inc. Rockford, Ill.) in the presence of 2× HALT protease/phosphatase inhibitor cocktail (Thermo Fisher inc. Rockford, Ill.). For classic Immunoprecipitation, lysates were combined with indicated antibodies for 48 hours at 4 C and combined with protein A/G agarose beads for 4 hours prior to elution with 2× Laemli Buffer at 100 C. Direct immunoprecipitation was performed following manufacturer protocol. Briefly, antibodies were covalently attached to agarose beads, lysate was combined with antibody-agarose bead conjugates for 24 hours prior to washes and elution with provided Elution Buffer. Protein samples were resolved by SDS-PAGE and transferred to PVDF membranes prior to incubation at 4 C with indicated primary antibodies; NHE-1, GLUT-1 and cytoplasmic domain-targeting EGFR were purchased from Santa Cruz Biotech (Santa Cruz, Calif.). p70S6K and pp70S6K, mTOR and pMTOR, pERM and ERM, Ezrin and pEzrin, pAKT and AKT, pPRAS40 and PRAS40, EGFR and pEGFR antibodies cleaved caspase-3 and β-Actin were purchased from cell signaling technology (Cambridge, Mass.). EGFR and CD44v6 neutralizing antibodies were purchased from R&D (Minneapolis, Minn.). PVDF membranes with primary antibody were incubated at room temperature with HRP conjugated secondary antibodies (BD Ann Arbor, Mich.) and resolved by chemiluminescence using the G-Box and Syngene software (Syngene Cambridge, UK). When possible, blots were stripped (Thermo Fischer, Rockford Ill.) and re-probed with a second primary antibody. Optical densities of western blots were measured using ImageJ open source software (National Institutes of Health) and validated using Adobe CS5. Nuclear and cytoplasmic isolation was performed using the subcellular fraction kit following manufacturer protocol (Thermo Fisher inc. Rockford, Ill.). Western blotting images chosen as representative depictions in the figures demonstrate equivalent results taken from biological replicates (N>3).

Computational Modeling

We simulated the biological system with the parameter values found in Tables 1 and 2, below, and with the system of equations presented below. These values were derived from the following literature sources, and a graphical model summary is presented in FIG. 3A:

1. Alexandre et al: In this work, the dependence of ROS (hydrogen peroxide) on paclitaxel is studied, and a dose-dependent effect is shown. The data shows an approximate 3-5× increase from basal ROS levels at 10-20 uM of paclitaxel. This informed the choice of the parameter value for $k_{ROS}$, such that it is 3× the basal rate of production.[65]

2. Chen et al: In this work, a roughly 3× increase is shown in Glut-1 concentrations following hypoxic exposure. We use this in modeling the parameter $k_{Glut1,H}$ such that it is 2× the basal rate of production.[66]

3. Kim et al: In this work, an experimental basis for a ROS threshold in stimulating HIF production is discussed.[67]

4. Krishnamachary, et al. In this work it is shown that after hypoxic exposure, the amount of CD44 is increased by approximately 1.5×. We use this information in modeling the parameter $k_{CD44,H}$ as 0.5× the basal rate of production.[68]

5. Tamada et al. This work experimentally supports the concept that the concentration of CD44 is correlated positively with the concentration of Glut-1, via knockdown studies.[69]

Initial conditions were supposed to be relatively low concentrations of all molecules. With regards to dynamics, we have assumed that the parameters governing the basal levels of each of the molecules are similar, such that the concentrations as depicted graphically appear as similar values. These results indicate, fundamentally, that the concentration of effectively acting Glut 1 in the cell cannot increase at early timescales, until the level of HIF increases, which can only occur when the ROS concentration surpasses a given threshold. Therefore, we observe that there is a theoretically predicted temporally delayed synergistic effect between the HIF and Glut 1 molecules that is requisite for the cell to be able to switch primary metabolic pathways. We emphasize that the magnitude of this effect is certainly dependent upon parameter values, but the qualitative phenomenon proposed by these results is stable, and represents a biological phenomena that may be observed directly.

Since the effect of the chemotherapeutic agent on CD44 was not available through existing data, we simulate the two cases wherein CD44 is not affected at all by the drug concentration (low effect case), and the case wherein CD44 is increased significantly by the presence of drug (high effect case). In simulations, the dotted lines for CD44 and Glut 1 represent the high effect cases, and we note that the value of the parameter does not significantly alter the observed synergistic effect between Glut 1 and HIF, and that the presence of HIF is still necessary for the increase in Glut 1.

In order to assay the differing effects that may be observed in vivo as compared to in vitro, two cases of drug concentration-time functions were simulated. In vivo systems tend to display an exponentially decaying concentration of active drug, whereas in vitro cellular systems tend to display a constant active drug concentration. We have shown definitively that theoretically the synergistic effect of HIF and Glut-1 is preserved in either case, regardless of the effect of the drug on the CD44 concentration, suggesting that biological observation of such an effect in one case may validate the presence of the effect in the other case.

The differential equations used to develop the model were as follows (parameters and values described in Tables 1 and 2, below):

$$\frac{d}{dt}[CD44] = \alpha_{CD44} + k_{CD44,D}d(t) + k_{CD44,H}[HIF] - \delta_{CD44}[CD44]$$

$$\frac{d}{dt}[HIF] = \alpha_{HIF} + k_{HIF}f([ROS]) - \delta_{HIF}[HIF]$$

$$\frac{d}{dt}[ROS] = \alpha_{ROS} + k_{ROS}d(t) - \delta_{ROS}[ROS]$$

$$\frac{d}{dt}[Glut1] = \alpha_{Glut1} + k_{Glut1,C}[CD44] + k_{Glut1,H}[HIF] - \delta_{Glut1}[Glut1]$$

$$f([ROS]) = \begin{cases} 0, & [ROS] < L \\ 1, & [ROS] \geq L \end{cases}$$

TABLE 1

Explanation and description of parameters used for equations to derive computational systems model

| Parameter | Description |
|---|---|
| $\alpha_X$ | Basal rate of production of molecule X. X may be one of CD44, HIF, ROS, or Glut 1 |
| $\delta_X$ | Basal rate of first-order degradation of molecule X. X may be one of CD44, HIF, ROS, or Glut 1 |
| $k_{CD44,D}$ | Constant of proportionality for change in production rate of CD44 molecules per unit change in drug concentration |
| $k_{CD44,H}$ | Constant of proportionality for change in production rate of CD44 molecules per unit change in HIF concentration |

TABLE 1-continued

Explanation and description of parameters used for
equations to derive computational systems model

| Parameter | Description |
|---|---|
| $k_{HIF}$ | Increase in rate of production of HIF when ROS surpasses a given threshold |
| $k_{ROS}$ | Constant of proportionality for change in production rate of ROS molecules per unit change in drug concentration |
| $k_{Glut1, C}$ | Constant of proportionality for increase in effective production rate of Glut 1 molecules per unit change in CD44 concentration |
| $k_{Glut1, H}$ | Constant of proportionality for change in production rate of Glut 1 molecules per unit change in HIF concentration |
| L | Concentration of ROS above which HIF production is enhanced |

TABLE 2

Numeric values applied to computational modeling (main
FIG. 3A, B) in order to create quantitative relationships
between proteins following xenobiotic stimuli. Approximations
were determined from literature sources as described in
detail in methods for computational modeling.

| Parameter | Numeric value |
|---|---|
| $\alpha_X$ | 0.2 µMol/day; X may be one of CD44, HIF, ROS, or Glut 1 |
| $\delta_X$ | 0.5 µMol/day; X may be one of CD44, HIF, ROS, or Glut 1 |
| $k_{CD44, D}$ | 0.2/day |
| $k_{CD44, H}$ | 0.1/day |
| $k_{HIF}$ | 1.8 µMol/day |
| $k_{ROS}$ | 0.6/day |
| $k_{Glut1, C}$ | 0.3/day |
| $k_{Glut1, H}$ | 0.4/day |
| L | 0.5 µMol |

Single Cell, Real-Time Assessment of Mitochondrial Reactive Oxygen Species (ROS)

Single cell analysis was performed as follows: Mitosox Red (Invitrogen, Carlsbad Calif.) was incubated with live parent cells for 30 minutes (5 µM), washed and recovered in phenol red-free DMEM with 2% FBS and treated with docetaxel (50 nM). Equivalent exposure times of immunofluorescent microscopy were used at each interval which was originally set at time 0 against an unstained control cell population. Images were captured by a NIKON Eclipse TI-U microscope with a 20× ELDW or 10× or 40× Plan-Apo objective lens (Nikon, Melville N.Y.) and NIS Elements Viewer version 3.22 (Nikon, Melville N.Y.) imaging software. A negative control (non-transfected) cell subset was used to normalize background and autofluorescence following docetaxel treatment. Individual cells were tracked over time and indications of cell death were noted using a 2 TdT-Fluor In Situ apoptosis detection kit (Trevigen Gaithersburg Md.). Cells were plotted as a function of apoptosis induction (or loss of adherence to culture dish indicating cell death) and changes in Mitosox fluorescence over time as shown in main figures.

Statistics

Statistical analysis was performed using Prism software (Graphpad, La Jolla Calif.) determined by ANOVA analysis followed by a Newman-Keuls post hoc test when values were represented between multiple groups and student's T-Test used to identify statistical significance between individual groups. 2-way ANOVA was employed to track significance between groups from in-vivo tumor volume assessments. The data are expressed as a mean±SEM.

Example 1. Acute Metabolic State-Transitioning is Associated with Acquired Tolerance and Clinical Resistance to Cytotoxic Chemotherapy Do human tumors which display clinical refractoriness adapt their metabolism under therapy pressure? To address this question, we used a human cancer explant model which closely represents clinical response and resistance to therapy by isolating fresh tissue from taxane-refractory breast cancer patients and re-treating these explants with cytotoxic chemotherapies at the respective clinically-observed maximal tumor concentration ($C_{max}$) in matrix-matched and autologous patient serum culture conditions[22] (FIG. 1A). As evidenced by unaltered cell viability following chemotherapy pressure, drug resistant tumor tissues showed increased glucose uptake determined by direct colorimetric measurement of culture serum (FIG. 1B). The addition of Lonidamine, an inhibitor of the rate-limiting enzyme of glycolysis, hexokinase[23,24], revealed residual populations with a diminished capacity for glucose uptake (FIG. 1C). Using immunohistochemistry from explant studies, we analyzed expression patterns of the glucose transporter 1 (GLUT-1), an isoform known to correlate significantly to aggressive forms of breast cancer[25]. Histological grading indicated a significant overall induction of GLUT-1 in the refractory tumor tissues following chemotherapy exposure (FIG. 1D, E). These preliminary studies suggested therapy augmented the glycolytic state in cancer tissue and cells from patients who display poor response in the clinic, a putative adaptation indicated by the pharmacologic sensitivities. To test these findings in-vivo, we evaluated uptake of the fluorescent glucose analog, 2-(N-7-Nitrobenz-2-oxa-1,3-diazol-4-yl)Amino)-2-Deoxyglucose (2-NBDG)[26] in residual tumor acutely (72 h) following sequential addition of docetaxel at maximum tolerated dose (MTD). In order to evaluate tumor cells which survived chemotherapy we utilized 2-NBDG fluorescence in-tandem with indication of apoptosis (TUNEL positivity), concentrating our observations on viable tissue immediately proximal to chemotherapy-ablated regions which may designate a survival benefit of those cells (TUNEL negative). Using confocal microscopy, we determined that viable tumor immediately adjacent to chemotherapy-ablated tissue took up glucose to a greater degree than viable tissue from vehicle control (FIG. 2A), a finding which reflects clinical evidence that acute reduction of glucose uptake acutely following chemotherapy correlates to enhanced cell death[27]. In order to dissect the role of tumor cells as independent drivers of therapy-induced glucose uptake, rather than a secondary effect of chemotherapy treatment, we injected docetaxel intratumorally (i.t.) and monitored whole tissue glucose levels using direct measurement from tissue homogenate. Following i.t.

injection, glucose levels were significantly higher within 12 hours post-administration. These data suggested a tumor-independent, rather than systemically-altered effect, which was validated by unaltered glucose levels in control neuronal tissue (FIG. 2B). Finally, to test whether a modified metabolic state is enhanced in chemotherapy-tolerant cancer cells, we utilized an in-vitro model in which breast cancer cells were treated with a transient (48 h), high dose of docetaxel chemotherapy and subsequently selected for viability (FIG. 2C); defined hereafter as drug tolerant cells (DTC). DTC demonstrated an enhanced glycolytic phenotype characterized by augmented intracellular ATP and ability to uptake 2-NBDG (FIG. 2D, E). Using a click-reactive methionine incorporation as well as CMV-promoter controlled GFP, we also determined an enhanced rate of protein synthesis which is augmented in therapy tolerant cells (FIGS. 2F-H). This glycolytic behavior was consistent in DTCs generated from a distinct class of *vinca*-alkaloid chemo-agents (FIG. 2I). Together, these data demonstrated that a glycolytic and nalyze etics behavior is induced by therapy, associates globally in cancer cells which survive treatment, and collectively implicate a metabolic role for cell plasticity during transiently-induced adaptive resistance.

Figure 3B:
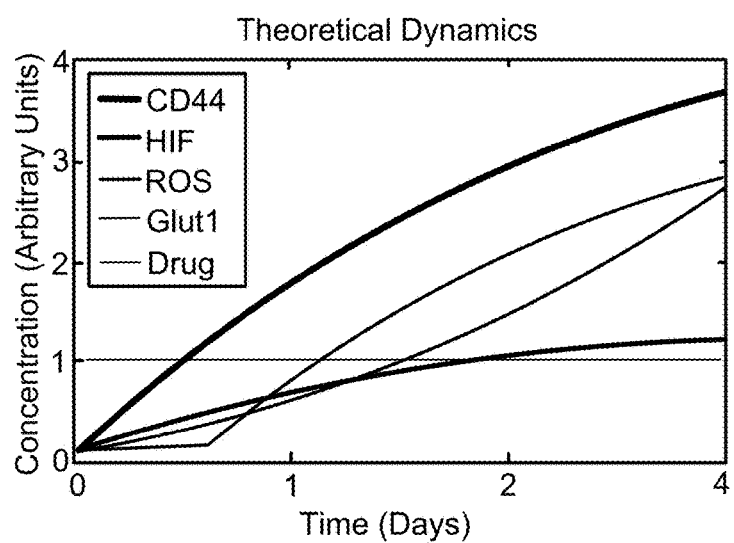

Example 2. Computational Biology Predicts Temporally-Distinct Cell Plasticities are Induced During Acquisition of Drug Tolerance Our evidence from human explant and in-vivo studies above, suggested that a metabolic switch was occurring in cells which acquire tolerance to a primary therapy. In an effort to elucidate a molecular mechanism underlying this dynamic system, we used a computational and mathematical approach interconnecting key cellular features from tumor heterogeneity which associated to drug resistance. While building the model, we focused on critical proteins which we have previously associated with induction of drug tolerance such as cell surface CD44 glycoprotein[14]. Using this starting point, we then connected our evidence that induction of GLUT-1 correlates to therapy refractory human tumors. Drawing from published literature derived from various scientific disciplines we were able to make broad connections and relationships between these proteins of interest and cytotoxic xenobiotics which revealed a potential role for both reactive oxygen species (ROS) and the hypoxia-inducible factor 1 alpha (HIF1A). Doing this enabled a predictive systems biology connecting theoretical interactions with quantitative dynamical activities, as shown in FIG. 3A (mathematical parameters are described in greater detail in methods, above). Based on this map, we then derived kinetic variations and predictions in cell plasticity using loosely-associated evidence in order to enable a qualitative understanding of the intracellular molecular dynamics. As shown in FIG. 3B, the model predicted that induction of CD44 shifts concomitantly with augmentation of ROS in response to cytotoxic stimuli. However, the model also described a temporally-constrained activation of redox-induced signaling leading to GLUT-1 expression, suggesting temporal event-ordering in glycolytic and phenotypic behavior is conferred, providing clues to the potential connections existing in these relationships. While this model depicted predictive activities in cell culture (constant drug exposure), a clinically-relevant model showed similar kinetic behavior (FIG. 8). Indeed, temporality of cell dynamics may provide critical insight into biological behaviors.

Example 3. Early-Ordered, Drug-Induced Cytokines Drive CD44 Expression while Redox Stress Drives Delayed, HIF1A-Mediated Glucose Uptake We sought to test the predictions generated by the computational model by analyzing temporal dynamics of drug-induced CD44 expression and glucose uptake, in vitro. Following sub-lethal doses of docetaxel at short (4 h) or long (24 h) incubation times we employed FACS analysis to detect cell surface CD44 expression or glucose uptake (2-NBDG). The data revealed an induction of CD44 is conferred within 4 hours of drug exposure, yet augmented glucose uptake was not observed until a later time point at the same drug load (24 h) (FIG. 3C). Based on these data and the computational model, we reasoned that cell stress-response to chemotherapy operates under temporally discordant dynamics which associate discrete cellular plasticity (CD44 induction and glucose uptake). To test this hypothesis, we used a high-density immunoarray to evaluate levels of intracellular chemokines and cytokines elicited immediately following exposure to chemotherapy (4 h) or at a delayed time-point (24 h). The data consistently showed that a defined set of cytokines associated with cell host-response are evoked by cancer cells within 4 hours exposure to docetaxel (IFN-γ[29], GM-CSF[30] and IL-23[29]) while induction of redox stress-related proteins (IL-8[31], IL-6[31] and angiogenin[32]) were conferred in a more delayed manner (24 h) (FIG. 3D left panel). Summarizing these dynamics, FIG. 3D schematic characterizes the temporal kinetics of early-induced cell host-response and delayed induction of redox stress-related cytokines as they correlate to CD44 expression and glucose uptake (FIG. 3D right panel). Our observations that a delay of redox stress-induced changes was validated using real-time imaging of a nitroreductase-sensitive fluorogenic probe in docetaxel-treated cells (FIG. 3I).

Based on these preliminary studies, we sought to test whether the release of cytokines contribute to early-induced CD44 expression. We first added exogenous IFN-γ, GM-CSF and IL-23 to cell culture. Using FACS analysis we confirmed that each cytokine was able to independently drive CD44 expression in a dose-dependent manner within 4 hours (FIG. 3J). Consistent with this observation, the addition of Bay-11 (a specific inhibitor of cytokine-dependent Nfkappab signaling[33]) or neutralizing antibodies targeting IFN-γ, GM-CSF and IL-23 modulated chemotherapy early-induced CD44 expression (FIG. 3E). Despite reports that some cytokines mediate glucose uptake in a cell autonomous fashion, we didn't observe any alterations in 2-NBDG uptake following incubation with exogenously-added early-induced cytokines (IFN-γ, GM-CSF, IL-23), nor those related to delayed redox imbalance (IL-8 and IL-6), even after 24 hours incubation (FIG. 3K). These results suggested to us that the mechanism underlying early-induced CD44 is not independently linked to the changes of glucose regulation in DTC. Therefore, we tested the prediction from the computational model that redox-associated elements arising in a temporally delayed manner, like HIF1A☐ and GLUT-1☐ are connected to the temporally-altered glucose uptake induced by chemotherapy. Using siRNA gene knockdown of☐ HIF1A☐ or a scrambled control, we confirmed by immunoblotting that GLUT-1 expression was increased by a HIF1A redox-sensitive pathway 24 hours following chemotherapy exposure but not at an earlier time point (4 h) (FIG. 3F). Consistent with this finding, knockdown of HIF1A led to a decrease of chemotherapy-induced glucose consumption as evidenced by 2NBDG uptake (FIG. 3G). As a final confirmation, we incubated DTC with catalase (an endogenous modulator of redox stress) and identified a reduced potential for glucose consumption as evidenced by 2NBDG uptake (FIG. 3L). Together, these results suggested that disparate temporal dynamics of cell surface protein expression patterns and glycolytic plasticity are conferred in cell-acquired chemotherapy tolerance.

Example 4. Early-Established CD44(v6)-AKT-EGFR Kinase-Scaffold Interactions Support a Delayed Glucose-Uptake Program Since our earlier report suggested that induction of CD44 contributes a functional role in therapy tolerance by scaffolding survival pathways[14], we reasoned that a functional relationship may also exist for CD44 to drive signaling events in metabolic transitioning. Indeed, CD44 has been reported to display functional control of phosphoinositide 3-kinase (PI3K)/AKT-family[35] which is known to mediate ubiquitous control of glucose and metabolic homeostasis. We first wanted to explore whether AKT was implicated in the augmented glucose uptake of DTC by incubating cells with an inhibitor of PI3K/AKT (PI103) or downstream mTORC1 inhibitor (Everolimus). 2-NBDG uptake evaluated by FACS revealed a greater suppression of glucose consumption in the DTC subset compared to drug naïve parent cells (FIG. 4A). Additional analysis of active AKT-family proteins using an immune-complexed array, we determined there is an enhanced ratio of phosphorylated AKT-family proteins in the DTC as compared to drug naïve parent cells (FIG. 4B). In an effort to test whether CD44 expression and AKT signaling were interconnected we used gene silencing by siRNA transfections. Western blot analysis showed that enhanced phosphorylation of AKT in DTC is reduced by silencing CD44 expression (FIG. 4C). These provided putative evidence for a relationship existing between the augmented AKT protein activities and CD44 induction. To test the hypothesis that chemotherapy-induced CD44, AKT and glucose uptake were causally connected, we treated siCD44-transfected parent cells with an acute, low-cytotoxic dose of docetaxel (24 h) and compared the activation of cortex signaling proteins against a similarly-dosed scrambled control. Consistent with reports that CD44 localizes a cortex-complex with the AKT scaffold Ezrin/Radixin/Moesin (ERM)[37], knockdown of CD44 prevented activation of Ezrin, ERM and AKT which was induced by chemotherapy in the siRNA control group (FIG. 4D). Indeed, gene knockdown of Ezrin confirmed the ERM cortex-complex was predisposing AKT activity in response to chemotherapy (FIG. 4G). We sought to examine upstream proteins of AKT to enable to clear picture of top-to-bottom kinase signaling pathways. We focused on the epidermal growth factor receptor (EGFR) which is well known to control the PI3K/AKT family in breast malignancies. We used western blot analysis to analyze and quantify kinetic changes in the activation (phosphorylation) of EGFR and AKT following chemotherapy pressure. We determined EGFR activity occurred early (within 1 hour) which preceded activation of AKT implicating a direct relationship between these activities (FIGS. 4E and 4H). In effort to validate that a cortex complex and scaffold-kinase interaction was induced between CD44-EGFR-AKT, we nalyz-precipitated AKT from chemotherapy-treated cells which revealed a physical scaffold is initiated with EGFR and ERM, an effect abolished by knockdown of the ultimate scaffolding-element, CD44 (FIGS. 4F and 4F). Further confirmation analyses of nalyz-complexes showed an enhanced scaffold-kinase interaction between EGFR and CD44 in DTC, validating the full composite of cortex signaling evoked in response to chemotherapeutic pressure (EGFR-CD44-ERM-AKT) (FIG. 4J). Lastly, we took additional steps to confirm a specific isoform of CD44 mediating this cortex scaffold, identifying from a series of in-vitro and human explant analyses to be derived from the CD44 variant isoform 6 (CD44v6) (FIGS. 6A-E).

Example 5. AKT-Dependent GLUT-1 Membrane Localization Predisposes Glucose Uptake in Drug Tolerant Tumors and Cells We next sought to construct a relationship which might exist between CD44 and GLUT-1 in the metabolic transitioning of DTC. In view of reported links between AKT activity and glucose transporter localization (GLUTs)[39], we asked whether the mechanism described above (CD44-clustered AKT activation) was supporting cellular trafficking of the delayed induction of GLUT-1 and thus leading to the temporally-evolved glycolytic phenotype in DTC. We observed, through subcellular fractionation and subsequent western blot analysis, that GLUT-1 was augmented in the membrane portion of DTC compared to parent, an effect which could be abolished by knockdown of the CD44-driven AKT signaling axis (FIG. 5A). These conclusions were supported by positive control via inhibition of the AKT pathway using the small molecule inhibitor, PI103 (FIG. 5A). Validating the role of this pathway-activation for glucose uptake, we observed that gene knockdown of CD44 significantly attenuated 2-NBDG uptake in DTC (FIG. 5B). Based on these data, we sought to translate our findings to in-vivo studies by analyzing residual tumors from an orthotopic, syngeneic mammary carcinoma model 72 hours after groups were treated with either docetaxel at MTD or vehicle. Confocal microscopy revealed enhanced expression of both CD44 and GLUT1 in residual tumors from docetaxel-treated mice, the intensity of fluorescence-detection of these proteins were greater than any region from vehicle control confirming an induction of expression rather than selection phenomena (FIG. 5C). By equalizing these signal intensities in confocal microscopy by modulating the gain control at high resolution, we confirmed that co-localization of CD44 and GLUT-1 was markedly enhanced in residual tumor volume following chemotherapy treatment (FIG. 5D). Indeed, by co-evaluating and quantifying GLUT-1 expression and CD44(v6) expression by IHC in explant tumor biopsies, we identified an co-induction pattern existed between these two markers following docetaxel treatment (FIG. 5E). Taken together, these data detail a complex arrangement of cortex and cell membrane signaling proteins are hosted through dynamic phenotypic heterogeneity to coordinate glycolytic transitioning in drug tolerant cancer cells.

Example 6. Chemotherapy-Induced Mitochondrial Exhaustion Associates Reductive Stress in Drug Tolerant Cells Since the computational model suggested a functional link existed between ROS and treatment with xenobiotics, we wanted to nalyze the temporal kinetics of ROS in response to docetaxel. By detecting changes in total intracellular ROS (CM-DCFDA) by FACS, we determined a temporal accumulation is induced as a consequence of therapy pressure (FIG. 6A). As a major source of cellular ROS, we investigated whether an early role for mitochondria provided an ROS burst which is known to initiate a feedback of universal oxidant stress[40]. Therefore, we monitored superoxide ($O_2^-$) production at the single cell level using a mitochondrial-localized fluorogenic probe (Mito-Sox). In order to determine whether temporal changes in $O_2^-$ production correlated with tolerance to chemotherapy, we multi-plexed real-time imaging of mitosox activity with low incidence of cell death following treatment of a toxic dose of chemotherapy (50 nM). The results indicated that cells which survive docetaxel will initiate a burst of ROS occurring early (4-8 h) (FIG. 6B). This is in contrast to a subset of vehicle control cells or cells which displayed sensitivity to docetaxel (since mitosox is not dynamically-sensitive to $O_2^-$, our observation for a loss of fluorescence seen in the chemotherapy-sensitive fraction may be a result of cell death-induced permeabilization and leaking of dye). These results are consistent with earlier evidence that a role for mitochondria is associated with chemoresistance[41]. Consistent with the hypothesis that mitochondrial ROS-burst may initiate reductive stress mechanisms, fluorescent microscopy of trimethylrhodamine (TMRM), a fluorescent indicator of mitochondrial membrane polarization, along with indication of reductive stress (nitro reductase) determined that once a drug tolerant state is established there is exhausted oxidative potential, a feature which is also correlative to apoptosis resistance[42] (FIG. 7A). In a separate positive control, we evaluated ROS in baseline levels of prostate cancer cells in which resistance to taxanes was generated by dose escalation over months of exposure (FIGS. 6J, 6K). Together, these data implicate an early role for mitochondria to drive the augmented reductive stress in drug tolerant populations, the initiating mechanism of redox-stress-related alterations in the acquisition of tolerance.

Example 7. Reductive Stress Mediates a Shunt to the PPP in Drug Tolerant Cells

Since our data suggested that redox imbalance exists in drug tolerant cancer cells, we wanted to elucidate whether the pentose phosphate pathway (PPP), a key modulator of reductive stress, was invoked to maintain a recalibrated homeostasis. To test this, we evaluated the function of the PPP in drug tolerant cancer cells by measuring an end-product for oxidant defense, reduced glutathione (GSH). We observed globally enhanced GSH in DTC compared to drug naïve parent cells (FIG. 6C). We sought to validate a connection between AKT-driven glucose uptake and PPP activity by examining the ability of DTC to modulate exogenous ROS. Therefore, we challenged drug naïve parent cells or DTC with transient exposures of hydrogen peroxide ($H_2O_2$). Following CM-DCFDA labeling, FACS analysis revealed an exquisite capacity of the DTCs to suppress exogenous oxidant stress, compared to parent, from their respective baseline levels (FIG. 6D). We hypothesized that the overactivation of AKT which drives the influx of glucose is therefore necessary for enhanced PPP. Consistent with this prediction we found that pharmacologic suppression of AKT led to reduced levels of total cell GSH (FIG. 6E). Interestingly, a recent report by Anastasiou and colleagues demonstrated that ROS shunts glucose to the PPP through inhibition of the pyruvate kinase M2 (PKM2) which enhances antioxidant machiner[43]. Based on our data above, we reasoned that this metabolic shunt may be relevant in DTC to mediate a redox homeostasis. To test this we evaluated total cell GSH levels in DTC following acute (3 hours) exposure to either ML-265, a PKM2 activator, or suppression of cellular ROS with catalase. We determined that both ML-265 and catalase led to diminished total levels of reduced glutathione in DTC, evidence which confirmed that ROS-mediated PKM2 inhibition contributes a metabolic shunt (FIG. 6F). Finally, quantification of whole cell GSH in residual tumor of docetaxel-treated mice revealed a significant global increase in contrast to vehicle control cohorts, confirming an in-vivo role for this drug tolerant metabolic phenotype (FIG. 6G).

Example 8. Systems Mapping of Metabolic Plasticity in Acquired Drug Tolerance Reveals a Temporal Coordination of Molecular Events Conclusively, the single cell analyses in-tandem with functional assays performed above allowed us to construct complete and comprehensive systems biology of metabolic behavior during the acquisition of therapy tolerance. By succinctly drawing connections between the molecular events instructed by chemotherapy, we uncovered a temporal event-ordering of molecular signals which is induced during the acquisition of chemotherapy tolerance. These pinpointed a dependence of early-driven phenotypic plasticity to support a temporally-dependent metabolic transition in drug tolerant cells. Depicted in FIG. 6H, the schematic describes how early chemokine- and cytokine-driven protein expression facilitate kinase-scaffolding, events which are concordant to mitochondrial activity. Subsequently, exhaustion of the mitochondria lead to a redox imbalance and oxidant stress, penultimate events which force conversion to an augmented glycolytic state reinforcing the PPP. Intriguingly, the temporal coordination appears critical in populations of cancer cells surviving chemotherapy treatment since loss of the early-established network suppresses this metabolic switch. Most notably, the experimentally-derived system validated both the temporal and proteomic relationships predicted by the computational modeling which was obtained from loosely-associated relationships connected by scientific literature. These data provide evidence that systems mapping and computational modeling of molecular behavior can be a useful tool to build and understand relationships in temporal capacities which might exist in the generation of chemotherapy tolerance leading to therapy failure.

Example 9. Metabolic Dysfunction and PPP Intermediates Drive Cross-Resistance to Anthracyclines in Drug Tolerant Cells Considering reports that transiently-acquired tolerance to anticancer therapeutics often confers cross-resistance[44], and anthracylcine-resistance or reduced cytotoxicity can arise via metabolic dehydrogenases, PPP intermediates or downstream products[45-49], we wanted to investigate whether DTC respond differently than drug naïve parent cells to the cell cycle-independent anthracycline, doxorubicin (dox). Indeed, dox is commonly combined with taxanes for treatment of TNBC[50]. Using trypan blue exclusion assays, we confirmed that DTC developed resistance to dox (FIG. 7A). Drug internalization studies indicated that drug efflux was not implicated in this cross-resistance (FIG. 7B). To test the hypothesis that enhanced PPP contributes anthracycline resistance, we co-treated drug naïve parent cells with dox and exogenous NADPH, GSH or ectopic G6PD expression and observed a reduction of doxorubicin-mediated toxicity (FIGS. 7C, 7J). Based on these results, we asked whether shutting down glycolysis and glucose-6-phosphate dehydrogenase (G6PD) could restore dox-induced cytotoxicity. Therefore, we co-incubated dox with inhibitors of PI3K/

AKT (PI103) or hexokinase (HK; lonidamine) as well as novel G6PD inhibitors (KB-458 and KB-697) in the DTC and parental fractions. While drug naïve parent cells exerted little synergism or a reversion of synergy with these combinations, DTC were exquisitely responsive, overtly driven to cell death by dox in combination (FIG. 7D). Immunoblots and drug internalization studies determined that pharmacologic inhibition of the targeted metabolic components were not modulating doxorubicin load in DTC, but rather the restored sensitivity was arising through glycolysis-driven intermediates downstream of AKT and HK (FIGS. 7E, 7F and 7K). These data were consistent with the hypothesis that the acquisition of drug tolerance relies on transcriptional and translational programs validated by our earlier evidences (FIG. 2F), machinery which are targeted by anthracyclines through DNA adduct formation and suppression of topoisomerase activity. Restoring activity of anthracyclines in DTC should therefore potentiate robust cell death, as evidenced by rational combinations with pharmacologic inhibitors of glycolysis.

Example 10. Temporally-Sequenced Therapeutic Intervention Exploits and Targets Metabolic Reprogramming to Enhance Antitumor Outcome Based on the above evidences that DTC are exquisitely sensitive to doxorubicin when combined with glycolysis inhibitors, we reasoned that sequence-dependence of cytotoxic chemotherapy (docetaxel) and AKT inhibition+anthracyclines (PI103+dox) can harness dysregulated metabolism to overcome cross-resistance. Our hypothesis was that treatment of a primary therapy (docetaxel) would reorganize the metabolic state of tolerant cancer cells, creating vulnerability in the cross-resistant populations to doxorubicin combination treatment. Therefore, we designed a 6-day (3×3) drug-schedule in-vitro using various combinations of docetaxel, doxorubicin and PI103 in discrete sequence. The results demonstrated that the best sequence and combination of treatment, defined by the number of residual cells adherent to the culture dish, was docetaxel followed by doxorubicin+PI103, nearly ablating the population of cancer cells in contrast to all other sequence and schedules (FIG. 7G). These data were consistent with the hypothesis that the first drug, docetaxel, will ablate a proportion of drug sensitive cells leaving a remaining population of 'DTC' with a re-programmed metabolic state. As elucidated from functional and viability assays, perturbing this metabolic re-programming with the addition of PI3K/AKT inhibitors restores and overtly sensitizes drug tolerant cells to anthracyclines creating an optimal, temporally-generated target for sequentially-administered combination drugs. Indeed, translating this same drug-schedule and sequence in-vivo demonstrated a similar synergistic effect on both tumor growth rate (FIG. 7G) as well as tumor volume (FIG. 7L). As evidenced by tumor growth curves from syngeneic mammary carcinoma models, the application of this drug schedule in specific sequence prevents the re-emergence of tumor growth following cessation of treatment (FIG. 7H).

Taken together, these detail a comprehensive mapping of metabolic behavior in drug tolerant cancer cells by describing a temporally-coordinated plasticity to drive cross-therapy resistance. This dysregulated pathway serves as a target for rationally designed drug schedules, introducing effective use of an old pair of chemotherapeutic agents.

Example 11. Metabolically-Activated Drug-Drug Conjugates (MADC) Exploit Adaptive Cross-Drug Resistance and Enhance Tumor Specificity As shown above, combination dox and PI103 work exquisitely to ablate drug-tolerant cells (see Examples above); however, there are clinical toxicities associated with all formulations of doxorubicin (Tacar et al., Journal of pharmacy and pharmacology 65, 157-170 (2013)). In an attempt to improve treatment, a single drug was conjugated with multiple payloads, providing a spatial advantage by linking doxorubicin and PI103. Furthermore, it was reasoned that the metabolic phenotype and glutathione-rich microenvironment of residual drug tolerant cells (an effect which we observed is created acutely by application of docetaxel) could serve as an 'activator' of the drug conjugate to release PI103 (PPP inhibition via AKT) and doxorubicin, concentrating activated drugs in chemo-tolerant tumor tissue. A number of reports have successfully utilized thiol-chemistry to exploit GSH as a mechanism to drive prodrug activation (Xu et al., Chemistry, an Asian journal 9, 199-205 (2014)) as well as release conjugates from nanoparticle-assembled drug-loaded vehicles (Ko and Oh, 15(8):3180-9 (2014)). A drug-drug conjugate was created by linking a disulfide moiety between the sterically unhindered hydroxyl group of doxorubicin and the phenolic hydroxyl of PI103. Indeed, conjugation of some moieties to the C14 hydroxyl position of doxorubicin have been shown to reduce activity, therefore rendering an inactive prodrug (Meyer-Losic et al., Journal of medicinal chemistry 49, 6908-6916 (2006)).

Figure 8A:
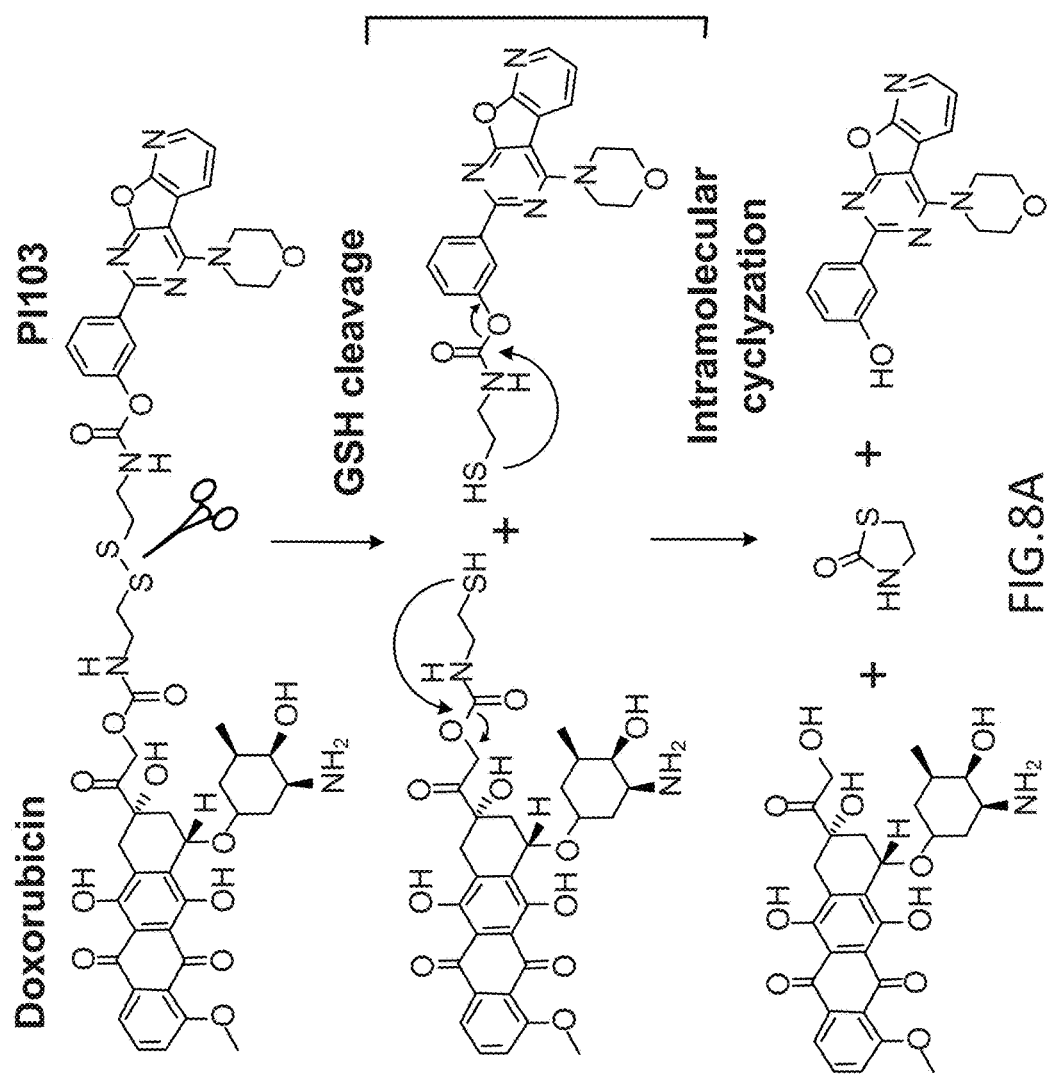
Figure 8B:
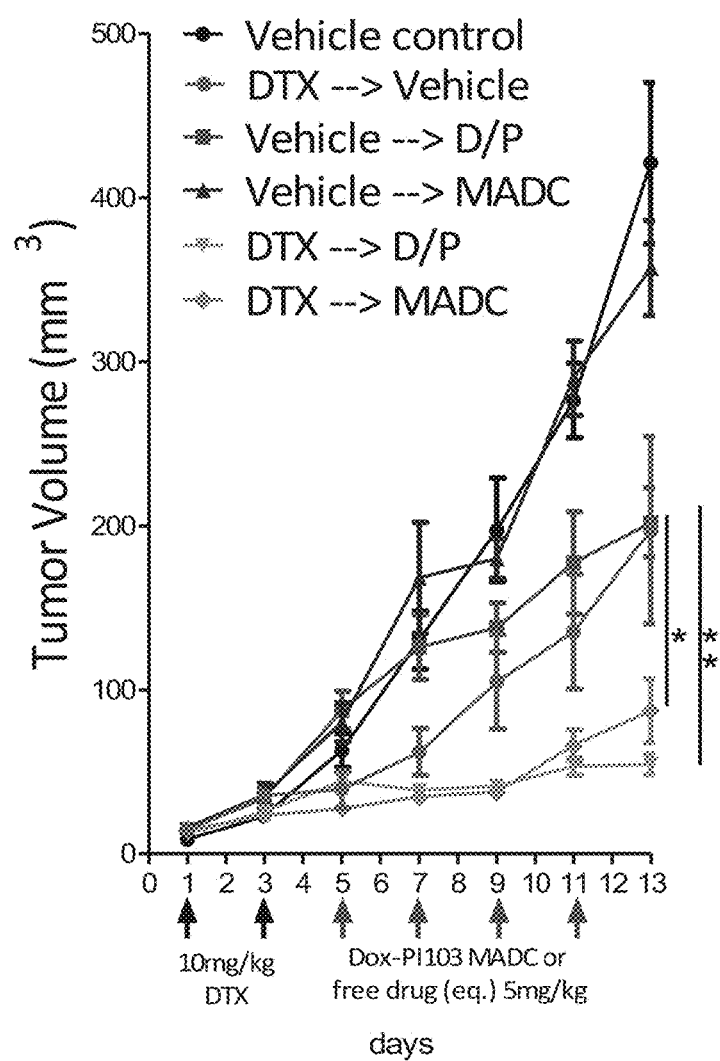
Figure 8E:
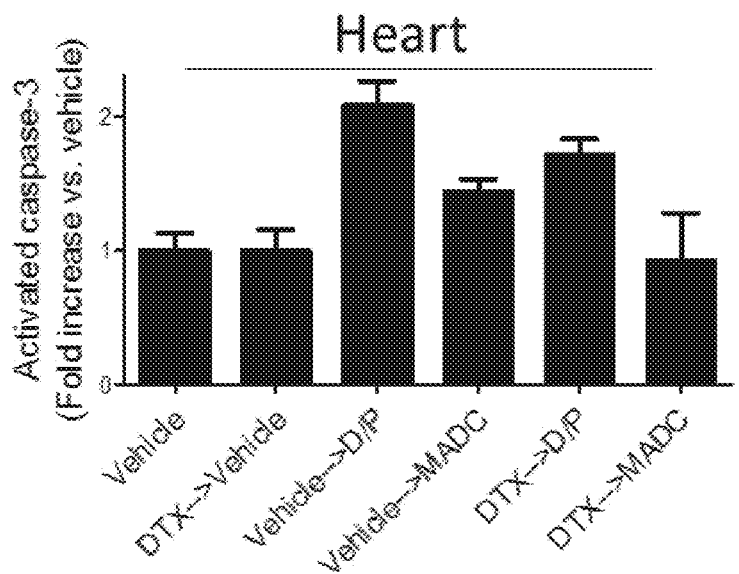
Figure 8F:
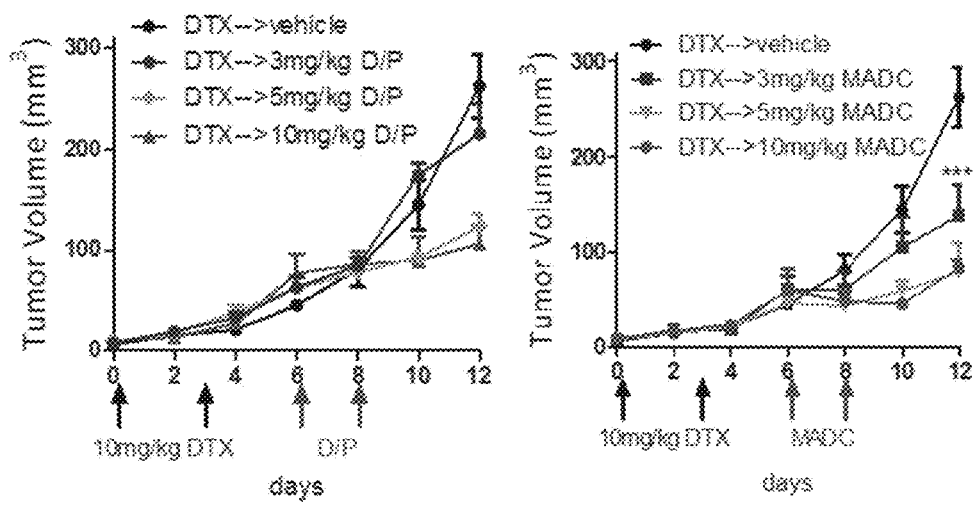
Figure 8G:
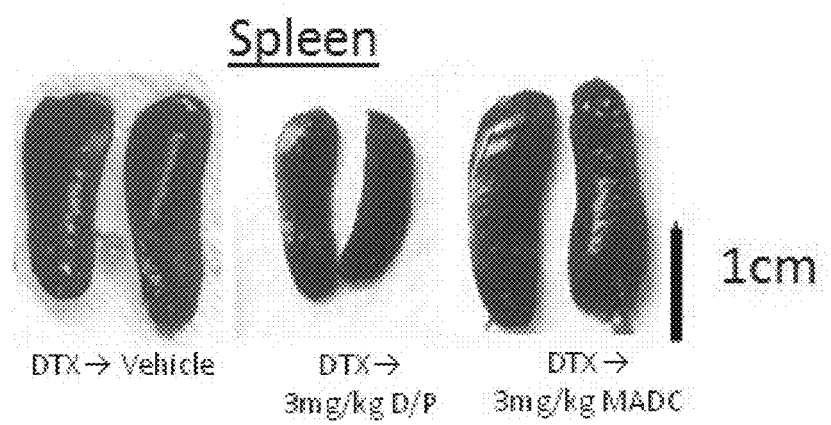
Figure 8H:
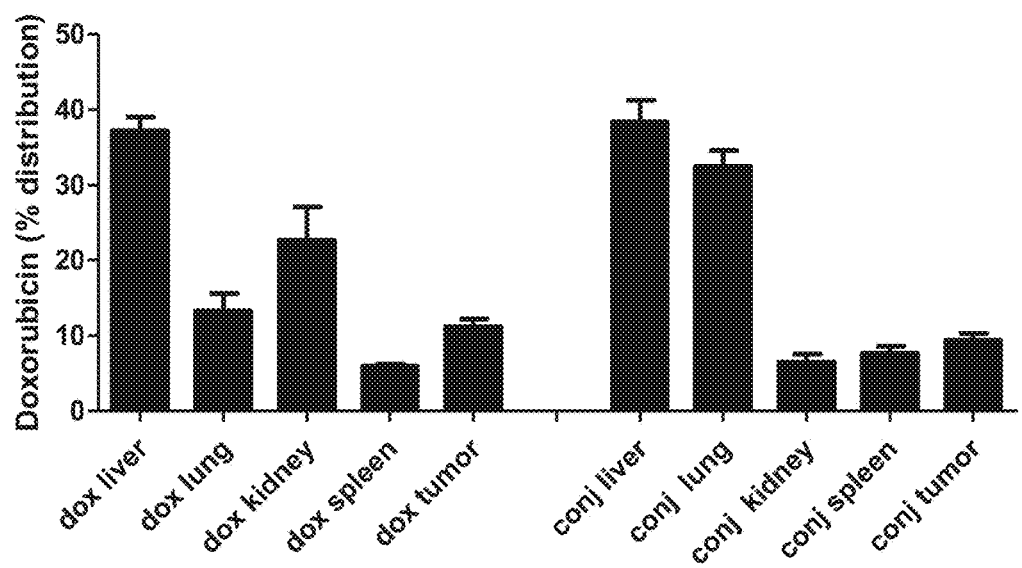

It was reasoned that the enriched pool of reduced glutathione, augmented acutely in residual tumors following docetaxel chemotherapy, might serve as an effective substrate to split the dithiol bond and create two active compounds (Dox and PI103) via intramolecular cyclization (FIG. 8A and Example 12). It was hypothesized that this Metabolically-Activated Drug-drug Conjugate (MADC) would function at maximal efficacy and with greatest specificity in chemotherapy tolerant cancer cells created after treatment with docetaxel (rich with reduced glutathione pools) and thus modulate systemic toxicities. An in-vivo study was designed creating drug-schedules following successive doses of docetaxel at MTD or vehicle control in distinct groups. Tumor volumes measured over time indicated that MADC operated poorly to suppress tumor growth in sequence with vehicle, a contrast to the effect of free drugs (Dox+PI103) (FIG. 8B). However, MADC in sequence with docetaxel elicited suppression of tumor growth, largely comparable to the combination of free drugs in similar sequence (FIG. 8B). These data highlight the requisite induction of metabolic re-programming within the tumor to promote dissociation of MADC to active compounds. More importantly, systemic toxicity was evaluated, and significant reduction of toxic burden was seen in the animals treated with MADC vs. free drug combination groups. Most notably, macroscopic indications of toxicity including hair and weight loss (FIG. 8C) as well as meylosuppression indicated by splenic miniaturization (Bally et al., Cancer Chemother Pharmacol 27, 13-19 (1990)) (FIG. 8D), were significantly attenuated in MADC-treated cohorts. Quantification of protein density from immunoblots of whole heart lysate demonstrated a lower indication of cardiotoxicity in MADC groups (FIG. 8E). Finally, in effort to dissect the dosing-response of MADC vs. free drugs, a dose-titration of doxorubicin+PI103 or MADC in sequence with docetaxel was performed. The results showed that 5 mg/kg and 10 mg/kg were saturating concentrations in-vivo in both free drug and MADC groups (FIG. 8F). However, at the lower concentration (3 mg/kg), MADC was shown to have a greater effect than free drug combination (FIG. 8F), an observation potentially supported by the spatial advantage between drugs of MADC as well as the sequestration of the phenolic hydroxyl of PI103 which renders the drug more bioactive. Similar to the previous results of toxicity, splenic miniaturization was negligible in MADC-treated mice, a stark contrast to the free drug combination which exerted no tumor suppressive effect at a similar concentration (FIG. 8G). Finally, a preliminary bio distribution study of the free doxorubicin or conjugate was performed on heterotopically-implanted 4T-1 syngeneic mammary carcninoma model. Mice were treated with 20 mg/kg equivalent of MADC or Doxorubicin or a vehicle control group (N=3 per group). After 24 hours, tumor, liver, kidney, spleen and lung were harvested, weighed and immediately homogenized in 10× lysis buffer containing DNAse (Bio-rad, Hercules Calif.) and incubated under agitation for 24 h at 4° C. Organ lysate was then centrifuged at 15,000 g and supernatant was filtered through a 0.2 mm filter syringe before aliquoted into quadruplicate wells of a 96-well plate. All samples were then read by fluorescence (488 ex/570 em). Autofluorescence determined from vehicle-treated control groups was subtracted from experimental groups and final fluorescence was determined as % arbitrary fluorescence units (AFU)/mg tissue as % increase from vehicle treated control values. The results, shown in FIG. 8H, show a greater concentration of the conjugate in the lung compared to the free drug administration in which greater accumulation was noted in the kidney, at the same time point (24 h).

Taken together, these provide the first evidence that a metabolic re-program in drug tolerant cancer cells can potentially serve as a target for rationally engineered drug-drug conjugates, overcoming toxicity associated with a pair of old chemotherapeutic agents.

Example 12. Synthesis of Doxorubicine-PI103 Conjugate

Step 1: Doxorubicine-BOC Protection

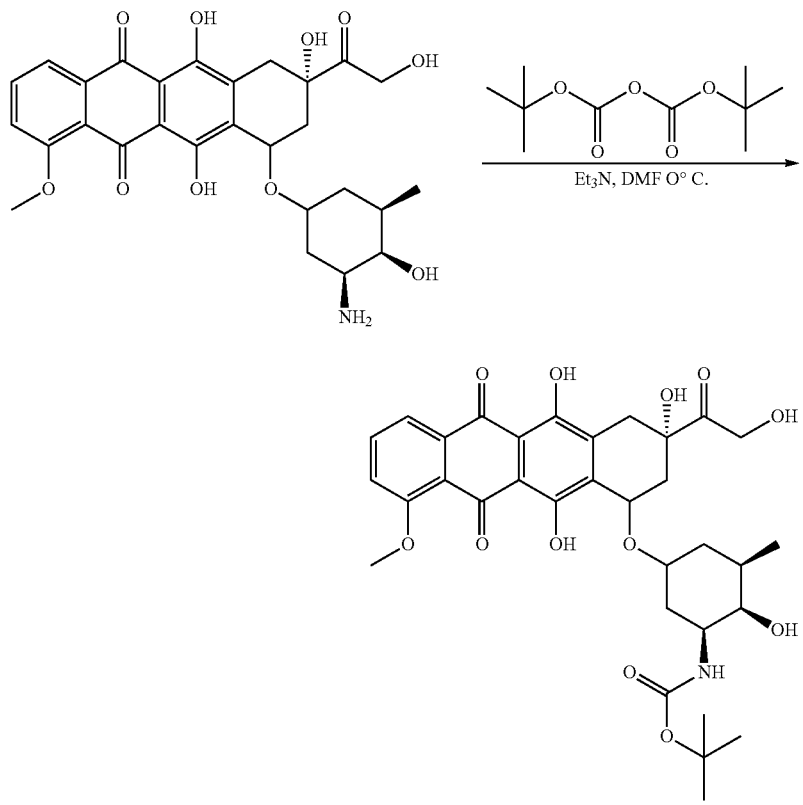 [SMILES: COc1cccc2c1C(=O)c1c(O)c3c(c(O)c1C2=O)C[C@@](O)(C(=O)CO)CC3OC1C[C@@H](C)[C@@H](O)[C@@H](N)C1 ; CC(C)(C)OC(=O)OC(=O)OC(C)(C)C ; COc1cccc2c1C(=O)c1c(O)c3c(c(O)c1C2=O)C[C@@](O)(C(=O)CO)CC3OC1C[C@@H](C)[C@@H](O)[C@@H](NC(=O)OC(C)(C)C)C1]

Procedure:

10.8 mg of Doxorubicine (1S,3S)-3-Glycoloyl-3,5,12-trihydroxy-10-methoxy-6,11-dioxo-1,2,3,4,6,11-hexahydro-1-tetracenyl 3-amino-2,3,6-trideoxy-α-L-lyxo-hexopyranoside) was dissolved in 2 mL DMF (Dimethyl formamide) in 5 mL vial with sure seal cap with magnetic pallet and under nitrogen. To this solution was added 3 microliter Triethylamine slowly at 0° C. To this resulting solution was added 4.4 microliter BOC-anhydride (Di-tert-butyl dicarbonate). The reaction mixture is stirred overnight and the organic solvents were evaporated under vacuum.

The red solid is further suspended in Dichoromethane and washed with water and brine and then dried over anhydrous MgSO4.

The total yield was 10.2 mg.

Step 2: PI103-Linker

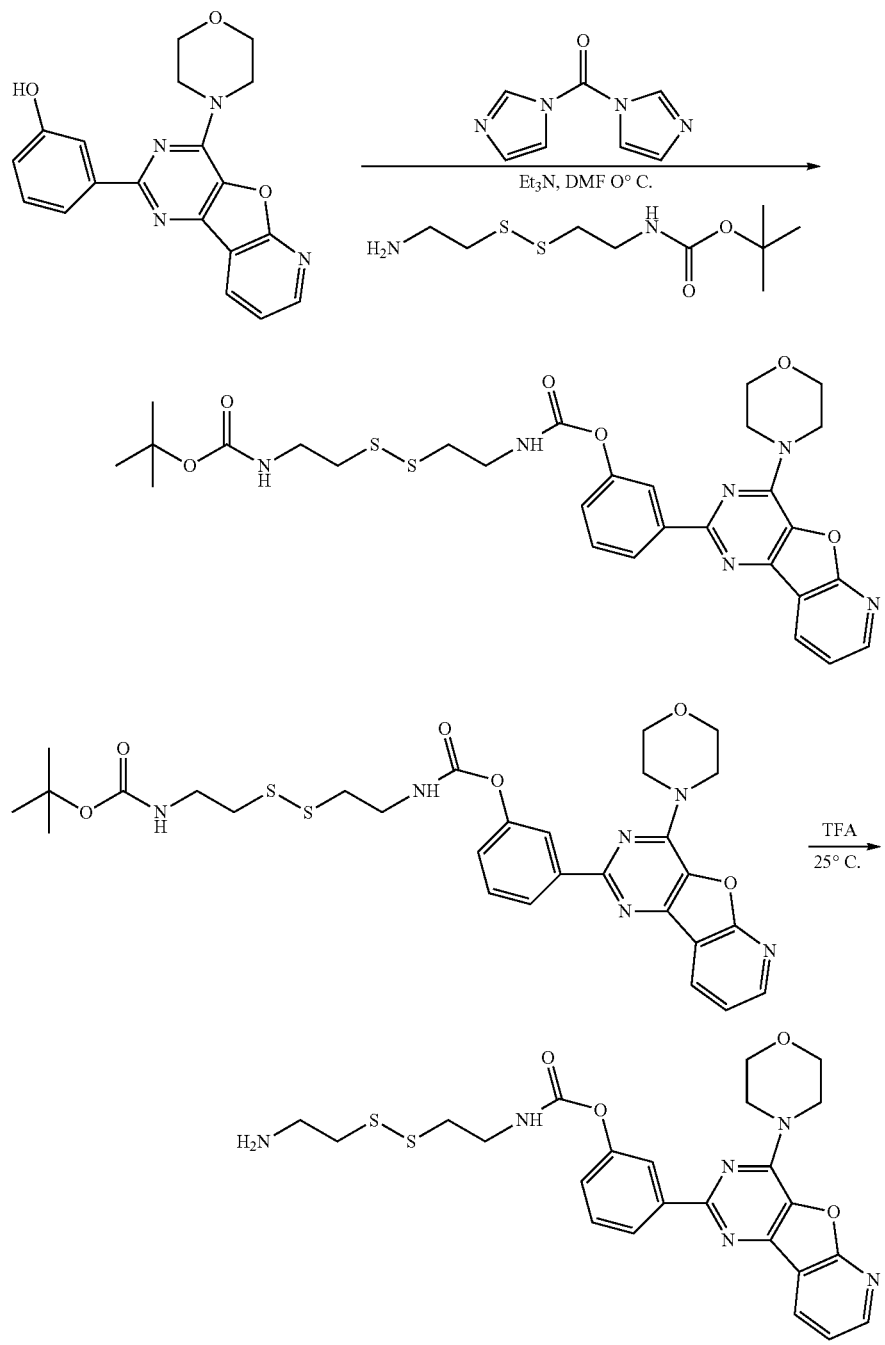

Scheme 2

Procedure:

7 mg of PI103 (3-[4-(4-Morpholinyl)pyrido[3',2':4,5]furo[3,2-d]pyrimidin-2-yl]phenol) was dissolved in 1.5 mL DMF (Dimethyl formamide) in 5 mL vial with sure seal cap with magnetic pallet and under nitrogen. To this solution was added 5 microliter Triethylamine slowly at 0° C. 3.5 mg of Carbonyldiimidazole is added to the above solution and reaction is stirred for another 3 hours. To this resulting solution was added 5 mg Mono-BOC-Cystamine (2-Methyl-2-propanyl {2-[(2-aminoethyl)disulfanyl]ethyl}carbamate).

The reaction mixture is stirred overnight and the organic solvents were evaporated under vacuum.

To this white solid was added a drop of TFA (Trifluroacetic acid)

The white solid is further suspended in Dichoromethane and was added a drop of TFA (Trifluroacetic acid). The resulting solution is stirred for an hour.

Organic layer was washed with water and brine and then dried over anhydrous MgSO4.

The total yield of light brown solid was 6.8 mg.

Step 3: Linking Doxorubicine to PI103 via Linker
Scheme 3
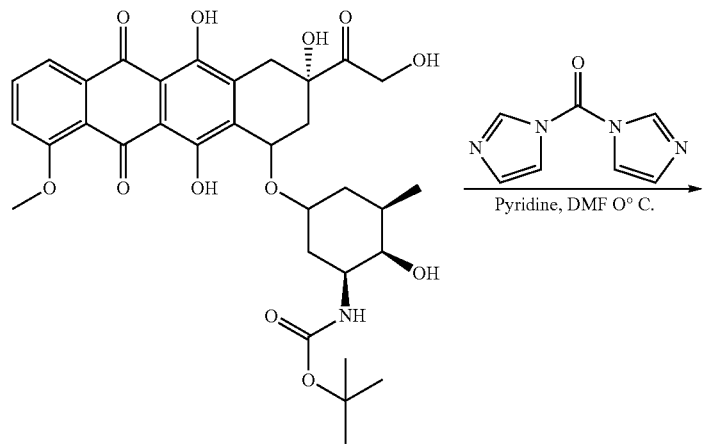
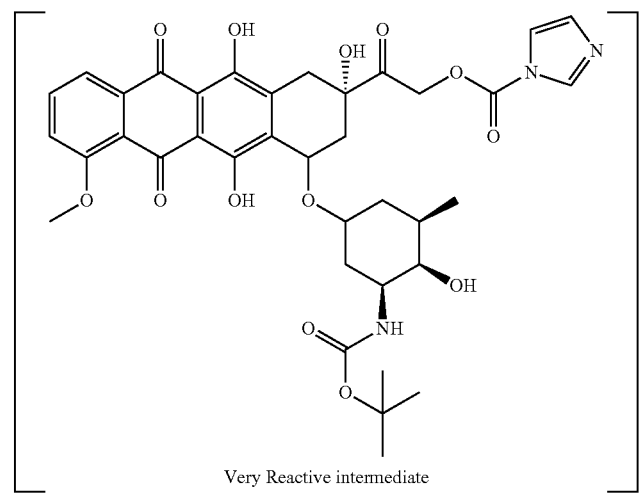
Very Reactive intermediate
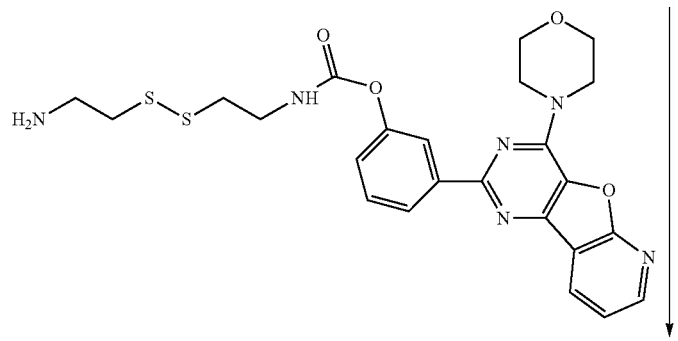

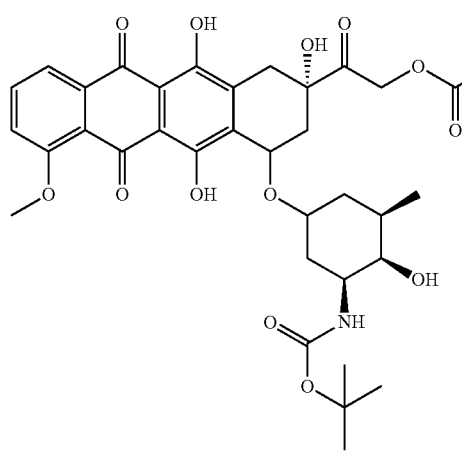
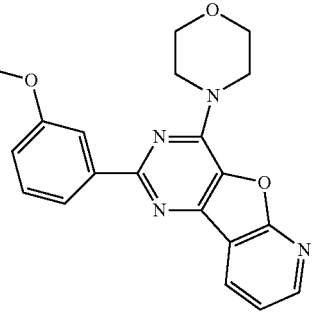

DCM,
TFA, 25° C.

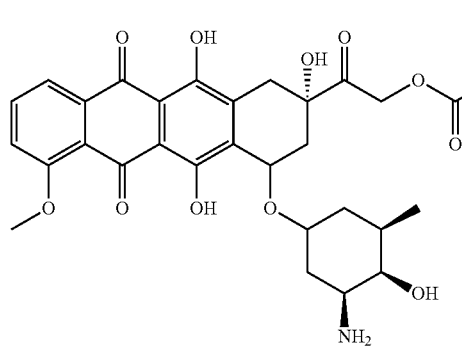
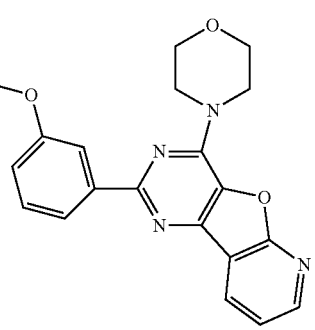

Procedure:

6 mg of Doxorubicine from step 1 was dissolved in excess 10 mL dry DMF (Dimethyl formamide) in 20 mL vial with sure seal cap with magnetic pallet and under nitrogen. To this solution was added 20 microliter pyridine at 0° C. 1.7 mg of Carbonyldiimidazole is added to the above solution and reaction is stirred for another 15 minutes. To this resulting solution was added 3 mg of PI103-Cystamine linker from step 2. The reaction mixture is stirred overnight and the organic solvents were evaporated under vacuum.

The red solid is further suspended in Dichoromethane and was added a drop of TFA (Trifluroacetic acid). The resulting solution is stirred for one hour.

Organic layer was washed with water and brine and then dried over anhydrous $MgSO_4$.

The total yield of light brown solid was 2.1 mg.

REFERENCES

1 Brock, A., Chang, H. & Huang, S. Non-genetic heterogeneity—a mutation-independent driving force for the somatic evolution of tumours. Nature reviews. Genetics 10, 336-342, doi:10.1038/nrg2556 (2009).
2 Almendro, V., Marusyk, A. & Polyak, K. Cellular heterogeneity and molecular evolution in cancer. Annual review of pathology 8, 277-302, doi:10.1146/annurev-pathol-020712-163923 (2013).
3 Marusyk, A., Almendro, V. & Polyak, K. Intra-tumour heterogeneity: a looking glass for cancer? Nat Rev Cancer 12, 323-334, doi:10.1038/nrc3261 (2012).
4 Gerlinger, M. & Swanton, C. How Darwinian models inform therapeutic failure initiated by clonal heterogeneity in cancer medicine. Br J Cancer 103, 1139-1143, doi:10.1038/sj.bjc.6605912 (2010).
5 Decker, S. & Sausville, E. A. Preclinical modeling of combination treatments: fantasy or requirement? Ann N Y Acad Sci 1059, 61-69, doi:10.1196/annals.1339.024 (2005).
6 Kirk, R. Targeted therapies: the maths behind combination therapy. Nat Rev Clin Oncol 10, 488, doi:10.1038/nrclinonc.2013.131 (2013).
7 Valero, V. & Hortobagyi, G. N. Are anthracycline-taxane regimens the new standard of care in the treatment of metastatic breast cancer? J Clin Oncol 21, 959-962 (2003).
8 Isakoff, S. J. Triple-negative breast cancer: role of specific chemotherapy agents. Cancer J 16, 53-61, doi:10.1097/PPO.0b013e3181d24ff7 (2010).
9 Guo, B. et al. Cross-resistance studies of isogenic drug-resistant breast tumor cell lines support recent clinical evidence suggesting that sensitivity to paclitaxel may be strongly compromised by prior doxorubicin exposure. Breast Cancer Res Treat 85, 31-51, doi:10.1023/B:BREA.0000021046.29834.12 (2004).
10 Chandarlapaty, S. Negative feedback and adaptive resistance to the targeted therapy of cancer. Cancer discovery 2, 311-319, doi:10.1158/2159-8290. CD-12-0018 (2012).
11 Cairns, J. Mutation selection and the natural history of cancer. Nature 255, 197-200 (1975).

12 Meacham, C. E. & Morrison, S. J. Tumour heterogeneity and cancer cell plasticity. *Nature* 501, 328-337, doi:10.1038/nature12624 (2013).

13 Kreso, A. et al. Variable clonal repopulation dynamics influence chemotherapy response in colorectal cancer. *Science* 339, 543-548, doi:10.1126/science.1227670 (2013).

14 Goldman, A. et al. Temporally sequenced anticancer drugs overcome adaptive resistance by targeting a vulnerable chemotherapy-induced phenotypic transition. *Nature communications* 6, 6139, doi:10.1038/ncomms7139 (2015).

15 Zhao, Y., Butler, E. B. & Tan, M. Targeting cellular metabolism to improve cancer therapeutics. *Cell death & disease* 4, e532, doi:10.1038/cddis.2013.60 (2013).

16 Warburg, O. On the origin of cancer cells. *Science* 123, 309-314 (1956).

17 Cairns, R. A., Harris, I. S. & Mak, T. W. Regulation of cancer cell metabolism. *Nat Rev Cancer* 11, 85-95, doi:10.1038/nrc2981 (2011).

18 Dong, C. et al. Loss of FBP1 by Snail-mediated repression provides metabolic advantages in basal-like breast cancer. *Cancer Cell* 23, 316-331, doi:10.1016/j.ccr.2013.01.022 (2013).

19 Liu, P. P. et al. Metabolic regulation of cancer cell side population by glucose through activation of the Akt pathway. *Cell death and differentiation* 21, 124-135, doi:10.1038/cdd.2013.131 (2014).

20 Elstrom, R. L. et al. Akt stimulates aerobic glycolysis in cancer cells. *Cancer Res* 64, 3892-3899, doi:10.1158/0008-5472.CAN-03-2904 (2004).

21 Cantor, J. R. & Sabatini, D. M. Cancer cell metabolism: one hallmark, many faces. *Cancer discovery* 2, 881-898, doi:10.1158/2159-8290.CD-12-0345 (2012).

22 Majumder, B. et al. Predicting clinical response to anticancer drugs using an ex vivo platform that captures tumour heterogeneity. *Nature communications* 6, 6169, doi:10.1038/ncomms7169 (2015).

23 Chambers, J. W., Fowler, M. L., Morris, M. T. & Morris, J. C. The anti-trypanosomal agent lonidamine inhibits *Trypanosoma brucei* hexokinase 1. *Molecular and biochemical parasitology* 158, 202-207, doi:10.1016/j.molbiopara.2007.12.013 (2008).

24 Paggi, M. G. et al. The role of mitochondrial hexokinase in neoplastic phenotype and its sensitivity to lonidamine. *Ann N Y Acad Sci* 551, 358-360 (1988).

25 Hussein, Y. R. et al. Glut-1 Expression Correlates with Basal-like Breast Cancer. *Translational oncology* 4, 321-327 (2011).

26 Zou, C., Wang, Y. & Shen, Z. 2-NBDG as a fluorescent indicator for direct glucose uptake measurement. *Journal of biochemical and biophysical methods* 64, 207-215, doi:10.1016/j.jbbm.2005.08.001 (2005).

27 Takei, T. et al. Enhanced apoptotic reaction correlates with suppressed tumor glucose utilization after cytotoxic chemotherapy: use of 99mTc-Annexin V, 18F-FDG, and histologic evaluation. *Journal of nuclear medicine: official publication, Society of Nuclear Medicine* 46, 794-799 (2005).

28 Miyawaki, A. Visualization of the spatial and temporal dynamics of intracellular signaling. *Dev Cell* 4, 295-305 (2003).

29 Jouanguy, E. et al. IL-12 and IFN-gamma in host defense against mycobacteria and salmonella in mice and men. *Current opinion in immunology* 11, 346-351 (1999).

30 Chen, G. H. et al. Role of granulocyte macrophage colony-stimulating factor in host defense against pulmonary *Cryptococcus neoformans* infection during murine allergic bronchopulmonary mycosis. *Am J Pathol* 170, 1028-1040, doi:10.2353/ajpath.2007.060595 (2007).

31 Tamm, M. et al. Hypoxia-induced interleukin-6 and interleukin-8 production is mediated by platelet-activating factor and platelet-derived growth factor in primary human lung cells. *Am J Respir Cell Mol Biol* 19, 653-661, doi:10.1165/ajrcmb.19.4.3058 (1998).

32 Hartmann, A. et al. Hypoxia-induced up-regulation of angiogenin in human malignant melanoma. *Cancer Res* 59, 1578-1583 (1999).

33 Scaife, C. L. et al. Nuclear factor kappaB inhibitors induce adhesion-dependent colon cancer apoptosis: implications for metastasis. *Cancer Res* 62, 6870-6878 (2002).

34 Wieman, H. L., Wofford, J. A. & Rathmell, J. C. Cytokine stimulation promotes glucose uptake via phosphatidylinositol-3 kinase/Akt regulation of Glut1 activity and trafficking. *Mol Biol Cell* 18, 1437-1446, doi:10.1091/mbc.E06-07-0593 (2007).

35 Martin, T. A., Harrison, G., Mansel, R. E. & Jiang, W. G. The role of the CD44/ezrin complex in cancer metastasis. *Critical reviews in oncology/hematology* 46, 165-186 (2003).

36 Gonzalez, E. & McGraw, T. E. The Akt kinases: isoform specificity in metabolism and cancer. *Cell Cycle* 8, 2502-2508 (2009).

37 Mori, T. et al. Structural basis for CD44 recognition by ERM proteins. *J Biol Chem* 283, 29602-29612, doi:M803606200 [pii] 10.1074/jbc.M803606200 (2008).

38 Davis, N. M. et al. Deregulation of the EGFR/PI3K/PTEN/Akt/mTORC1 pathway in breast cancer: possibilities for therapeutic intervention. *Oncotarget* 5, 4603-4650 (2014).

39 Kohn, A. D., Summers, S. A., Birnbaum, M. J. & Roth, R. A. Expression of a constitutively active Akt Ser/Thr kinase in 3T3-L1 adipocytes stimulates glucose uptake and glucose transporter 4 translocation. *J Biol Chem* 271, 31372-31378 (1996).

40 Dikalov, S. Cross talk between mitochondria and NADPH oxidases. *Free Radic Biol Med* 51, 1289-1301, doi:10.1016/j.freeradbiomed.2011.06.033 (2011).

41 Su, W. P. et al. Mitochondrial uncoupling protein 2 regulates the effects of paclitaxel on Stat3 activation and cellular survival in lung cancer cells. *Carcinogenesis* 33, 2065-2075, doi:10.1093/carcin/bgs253 (2012).

42 Bonnet, S. et al. A mitochondria-K+ channel axis is suppressed in cancer and its normalization promotes apoptosis and inhibits cancer growth. *Cancer Cell* 11, 37-51, doi:10.1016/j.ccr.2006.10.020 (2007).

43 Anastasiou, D. et al. Inhibition of pyruvate kinase M2 by reactive oxygen species contributes to cellular antioxidant responses. *Science* 334, 1278-1283, doi:10.1126/science.1211485 (2011).

44 Sharma, S. V. et al. A chromatin-mediated reversible drug-tolerant state in cancer cell subpopulations. *Cell* 141, 69-80, doi:S0092-8674(10)00180-7 [pii] 10.1016/j.cell.2010.02.027 (2010).

45 Riganti, C., Gazzano, E., Polimeni, M., Aldieri, E. & Ghigo, D. The pentose phosphate pathway: an antioxidant defense and a crossroad in tumor cell fate. *Free Radic Biol Med* 53, 421-436, doi:10.1016/j.freeradbiomed.2012.05.006 (2012).

46 Phan, L. M., Yeung, S. C. & Lee, M. H. Cancer metabolic reprogramming: importance, main features, and potentials for precise targeted anti-cancer therapies. *Cancer biology & medicine* 11, 1-19, doi:10.7497/j.issn.2095-3941.2014.01.001 (2014).

47 Polimeni, M. et al. Modulation of doxorubicin resistance by the glucose-6-phosphate dehydrogenase activity. *Biochem J* 439, 141-149, doi:10.1042/BJ20102016 (2011).

48 Villani, F. et al. Prevention of doxorubicin-induced cardiomyopathy by reduced glutathione. *Cancer Chemother Pharmacol* 28, 365-369 (1991).

49 Westman, E. L. et al. Bacterial inactivation of the anticancer drug doxorubicin. *Chemistry & biology* 19, 1255-1264, doi:10.1016/j.chembiol.2012.08.011 (2012).

50 Yagata, H., Kajiura, Y. & Yamauchi, H. Current strategy for triple-negative breast cancer: appropriate combination of surgery, radiation, and chemotherapy. *Breast Cancer* 18, 165-173, doi:10.1007/s12282-011-0254-9 (2011).

51 Preuss, J. et al. Identification and characterization of novel human glucose-6-phosphate dehydrogenase inhibitors. *Journal of biomolecular screening* 18, 286-297, doi:10.1177/1087057112462131 (2013).

52 Leder, K. et al. Mathematical modeling of PDGF-driven glioblastoma reveals optimized radiation dosing schedules. *Cell* 156, 603-616, doi: 10.1016/j.cell.2013.12.029 (2014).

53 Lee, J. V. et al. Akt-Dependent Metabolic Reprogramming Regulates Tumor Cell Histone Acetylation. *Cell metabolism*, doi:10.1016/j.cmet.2014.06.004 (2014).

54 Kreso, A. et al. Self-renewal as a therapeutic target in human colorectal cancer. *Nature medicine* 20, 29-36, doi:10.1038/nm.3418 (2014).

55 Seguin, L. et al. An integrin beta3-KRAS-RalB complex drives tumour stemness and resistance to EGFR inhibition. *Nat Cell Biol* 16, 457-468, doi:10.1038/ncb2953 (2014).

56 Gupta, P. B. et al. Stochastic state transitions give rise to phenotypic equilibrium in populations of cancer cells. *Cell* 146, 633-644, doi:10.1016/j.cell.2011.07.026 (2011).

57 Bernardini, N. et al. Comparative activity of doxorubicin and its major metabolite, doxorubicinol, on V79/AP4 fibroblasts: a morphofunctional study. *Experimental and molecular pathology* 55, 238-250 (1991).

58 Heibein, A. D., Guo, B., Sprowl, J. A., Maclean, D. A. & Parissenti, A. M. Role of aldo-keto reductases and other doxorubicin pharmacokinetic genes in doxorubicin resistance, DNA binding, and subcellular localization. *BMC Cancer* 12, 381, doi:10.1186/1471-2407-12-381 (2012).

59 Bains, O. S. et al. A correlation between cytotoxicity and reductase-mediated metabolism in cell lines treated with doxorubicin and daunorubicin. *The Journal of pharmacology and experimental therapeutics* 347, 375-387, doi: 10.1124/jpet.113.206805 (2013).

60 Kostrzewa-Nowak, D. et al. Bioreductive activation of mitoxantrone by NADPH cytochrome P450 reductase. Implications for increasing its ability to inhibit the growth of sensitive and multidrug resistant leukaemia HL60 cells. *Cancer Lett* 245, 252-262, doi:10.1016/j.canlet.2006.01.012 (2007).

61 Don, J. R. et al. Synthetic lethal metabolic targeting of cellular senescence in cancer therapy. *Nature* 501, 421-425, doi:10.1038/nature12437 (2013).

62 Kortylewski, M. et al. Regulation of the IL-23 and IL-12 balance by Stat3 signaling in the tumor microenvironment. *Cancer Cell* 15, 114-123, doi:10.1016/j.ccr.2008.12.018 (2009).

63 Takeda, M. et al. The establishment of two paclitaxel-resistant prostate cancer cell lines and the mechanisms of paclitaxel resistance with two cell lines. *The Prostate* 67, 955-967, doi:10.1002/pros.20581 (2007).

64 Mehrara, E., Forssell-Aronsson, E., Ahlman, H. & Bernhardt, P. Specific growth rate versus doubling time for quantitative characterization of tumor growth rate. *Cancer Res* 67, 3970-3975, doi:10.1158/0008-5472. CAN-06-3822 (2007).

65 Alexandre, J. et al. Accumulation of hydrogen peroxide is an early and crucial step for paclitaxel-induced cancer cell death both in vitro and in vivo. *Int J Cancer* 119, 41-48, doi:10.1002/ijc.21685 (2006).

66 Chen, C., Pore, N., Behrooz, A., Ismail-Beigi, F. & Maity, A. Regulation of glut1 mRNA by hypoxia-inducible factor-1. Interaction between H-ras and hypoxia. *J Biol Chem* 276, 9519-9525, doi:10.1074/jbc.M010144200 (2001).

67 Kim, H. S., Oh, J. M., Jin, D. H., Yang, K. H. & Moon, E. Y. Paclitaxel induces vascular endothelial growth factor expression through reactive oxygen species production. *Pharmacology* 81, 317-324, doi:10.1159/000119756 (2008).

68 Krishnamachary, B. et al. Hypoxia regulates CD44 and its variant isoforms through HIF-1alpha in triple negative breast cancer. *PLoS One* 7, e44078, doi:10.1371/journal.pone.0044078 (2012).

69 Tamada, M. et al. Modulation of glucose metabolism by CD44 contributes to antioxidant status and drug resistance in cancer cells. *Cancer Res* 72, 1438-1448, doi:10.1158/0008-5472. CAN-11-3024 (2012).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A metabolically-activated drug conjugate having the structure:

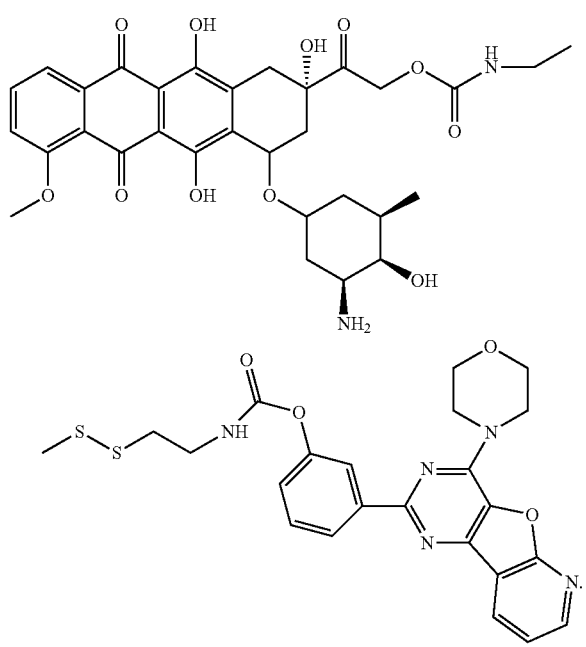

2. A method of treating a subject who has drug-resistant cancer, the method comprising administering to the subject the metabolically-activated drug conjugate of claim 1.

3. The method of claim 2, wherein the cancer is resistant to a cytotoxic agent.

4. A method of treating a subject who has cancer, the method comprising:

administering a round of induction therapy, wherein the round of induction therapy comprises administration of an amount of a cytotoxic agent or radiation therapy sufficient to increase glucose uptake or induce drug resistance in the cancer cells; and administering a therapeutically effective amount of the metabolically-activated drug conjugate of claim 1.

5. The method of claim 4, wherein the metabolically-activated drug conjugate is administered within about 24-240 hours after a final dose of the round of induction therapy.

* * * * *